(12) United States Patent
Schuetz et al.

(10) Patent No.: US 6,759,238 B1
(45) Date of Patent: Jul. 6, 2004

(54) MULTIDRUG RESISTANCE ASSOCIATED PROTEINS AND USES THEREOF

(75) Inventors: John Schuetz, Memphis, TN (US); Arnold Fridland, Memphis, TN (US)

(73) Assignee: St. Jude Children's Research Hospital, Memphis, TN (US)

(*) Notice: Subject to any disclaimer, the term of this patent is extended or adjusted under 35 U.S.C. 154(b) by 0 days.

(21) Appl. No.: 09/281,646

(22) Filed: Mar. 31, 1999

(51) Int. Cl.[7] .................... C12N 5/00; C12Q 1/68; C12P 21/06; C07K 16/00; C07H 21/04

(52) U.S. Cl. .................... 435/325; 435/6; 435/69.1; 530/389.1; 536/23.1

(58) Field of Search .................... 435/6, 69.1, 325; 530/389.1; 536/23.1

(56) References Cited

FOREIGN PATENT DOCUMENTS

| WO | WO 97/31111 | 8/1997 |
|----|-------------|--------|
| WO | WO 99/49735 | 10/1999 |
| WO | WO 00/26245 | 5/2000 |

OTHER PUBLICATIONS

Hillier, L. et al., Homo sapiens cDNA clone similar to MRP_human P33527 multidrug resistance–associated, EMBL Online, Accession No. R35797, XP002153229, 1995.

Hillier, L. et al., Homo sapiens cDNA clone similar to SP:MRP P33527 multidrug, EMBL Online, Accession No.R35798, XP002153230, 1995.

Kool, M. et al., Analysis of Expression of cMOAT(MRP2), MRP3, MRP4, and MRP5, Homologues of the Multidrug Resistance–associated Protein Gene (MRP1), in Human Cancer Cell Lines, Cancer Research vol. 57: 3537–3547, 1997.

Lee, K. et al., Isolation of MOAT–B, a Widely Expressed Multidrug Resistance–associated Protein/Canalicular Multispecific Organic Anion Transporter–related Transporter, Cancer Research vol. 58: 2741–2747, 1998.

Lee, K. et al., Isolation of MOAT–B, an MRP/cMOAT–related transporter over–expressed in a cisplatin resistant cell line, Proceeding of the Amer. Assoc. for Cancer Research vol. 39: Abstract No. 1151, 1998.

Loe, D.W. et al., Biology of the Multidrug Resistance–associated Protein, MRP, European J. Cancer vol. 32A: 945–957, 1996.

Nienhuis, A.W. et al., St. Jude Children's Research Hospital Scientific Report No. vol. 31: 52, 1997.

Robbins, B.L. et al., A Human T Lymphoid Cell Variant Resistant to the Acyclic Nucleoside Phosphonate 9–(2–Phosphonylmethoxyethyl) adenine Shows a Unique Combination of a Phosphorylation Defect and Increased Efflux of the Agent, Molecular Pharmacology vol. 47: 391–397, 1995.

Schuetz, J.D. et al., MRP4: A previously unidentified factor in resistance to nucleoside–based antiviral drugs, Nature Medicine vol. 5, No.9: 1048–1051, 1999.

*Primary Examiner*—Hankyel T. Park
(74) *Attorney, Agent, or Firm*—Licata & Tyrrell P.C.

(57) ABSTRACT

The present invention relates to multi-drug resistance, specifically to multi-drug resistant protein 4 (MRP4) and uses thereof. The present invention provides nucleic acid encoding MRP4, MRP4 protein, antibody reactive to MRP4 and discloses MRP4 as perhaps the first mammalian efflux pump described for nucleoside analogs. The present invention provides the first example of a role of MRP4 in drug resistance. Certain patients who develop drug resistance to anti-microbial therapy or anti-cancer therapy may develop cellular resistance mediated by MRP4. Accordingly, the present invention possesses both diagnostic and therapeutic utility as diagnostic kits, including drug assays and screens are contemplated, as well as pharmaceutical compositions and the corresponding methods of their respective use. For example, a diagnostic kit is disclosed that may be used in order to facilitate determination of patient susceptibility to MRP4 mediated drug resistance.

24 Claims, 27 Drawing Sheets

Alignment of MRP Family Members

```
                            _____A_____
MRP1    (1308-1531)  FVLRHINVTI NGGEKVGIVG RTGAGKSSLT LGLFRINESA EGEIIIDGIN  1357
cMOAT   (1315-1545)  LVLRGITCDI GSMEKIGVVG RTGAGKSSLT NCLFRILEAA GGQIIIDGVD  1364
MRP3    (262-485)    LVLRDLSLHV HGGEKVGIVG RTGAGKSSMT LACSRILEAA KGEIRIDGLN   311
38091.aa             ---------- ---------- ---------- ---------- ----------
MRP5                 --------TI KPKEKIGIVG RTGSGKSSLG MALFRLVELS GGCIKIDGVR    42
mrp6    (1178-1401)  LAVQGVSFKI HAGEKVGIVG RTGAGKSSLA SGLLRLQEAA EGGIWIDGVP  1227

Consensus            .........I ...EK.GIVG RTGAGKSSL. ..L.R..E.A .G.I.IDG..    50

MRP1    (1308-1531)  IAKIGLHDLR FKITIIPQDP VLFSGSLRMN LDPFSQYSDE EVWTSLELAH  1407
cMOAT   (1315-1545)  IASIGLHDLR EKLTIIPQDP ILFSGSLRMN LDPFNNYSDE EIWKALELAH  1414
MRP3    (262-485)    VADIGFHDVR CQMTIIPRDP ILFSGTLRMN LDPFGSYSEE DIWWALELSH   361
38091.aa             ---------- ---------- ---------- ---------- -AWH----EE     5
MRP5                 ISDIGLADLR SKLSIIPQEP VLFSGTVRSN LDPFNQYTED QIWDALERTH    92
MRP6    (1178-1401)  IAHVGLHTLR SRISIIPQDP ILFPGSLRMN LDLLQEHSDE AIWAALETVQ  1277

Consensus            IA.IGLHDLR ....IIPQDP .LFSG.LRMN LDPF..YS.E .IW.ALE..H   100
                                                  _____C_____  _____B
MRP1    (1308-1531)  LKDFVSALPD KLDHECAEGG ENLSVGQRQL VCLARALLRK TKILVLDEAT  1457
cMOAT   (1315-1545)  LKSFVASLQL GLSHEVTEAG GNLSIGQRQL LCLGRALLRK SKILVLDEAT  1464
MRP3    (262-485)    LHTFVSSQPA GLDFQCSEGG ENLSVGQRQL VCLARALLRK SRILVLDEAT   411
38091.aa             LKETIEDLPG KMDTELAESG SNFSVGQRQL VCLARAILRK NQILIIDEAT    55
MRP5                 MKECIAQLPL KLESEVMENG DNFSVGERQL LCIARALLRH CKILILDEAT   142
MRP6    (1178-1401)  LKALVASLPG QLOYKCADRG EDLSVGQKQL LCLARALLRK TQILILDEAT  1327

Consensus            LK..V..LP. .L...E..E.G .NLSVGQRQL .CLARALLRK ..IL.LDEAT   150

MRP1    (1308-1531)  AAVDLETDDL IQSTIRTQFE DCTVLTIAHR LNTIMDYTRV IVLDKGEIQE  1507
cMOAT   (1315-1545)  AAVDLETDNL IQTTIQNEFA HCTVITIAHR LHTIMDSDKV MVLDNGKIIE  1514
MRP3    (262-485)    AAIDLETDNL IQATIRTQFD TCTVTIAHR LNTIMDYTRV LVLDKGVVAE   461
38091.aa             ANVDPRTDEL IQKKIREKFA HCTVLTIAHR LNTIIDSDKI MVLDSGRLKE   105
MRP5                 AAMDTETDLL IQETIREAFA DCTMLTIAHR LHTVLGSDRI MVLAQGQVVE   192
MRP6    (1178-1401)  AAVDPGTELQ MQAMLGSWFA QCTVLLIAHR LRSVMDCARV LVMDKGQVAE  1377

Consensus            AAVD.ETD.L IQ.TIR..FA .CTVLTIAHR L.TIMD..RV .VLD.G...E   200

MRP1    (1308-1531)  YGAPSDLQQ  R-GLFYSMAK DAGLV----- ---------- ----------  1531
cMOAT   (1315-1545)  YGSPEELLQI P-GPFYFMAK EAGIENVNST KF-------- ----------  1545
MRP3    (262-485)    FDSPANLIAA R-GIFYGMAR DAGLA----- ---------- ----------   485
38091.aa             YDEPYVLLQN KESLFYKMVQ QLGKAEAAAL TETAHQVYFK RNYPHIGHTD   155
MRP5                 FDTPSVLLSN DSSRFYAMFA AAENKVAVKG ---------- ----------   222
MRP6    (1178-1401)  SGSPAQLLAQ K-GLFYRLAQ ESGLV----- ---------- ----------  1401

Consensus            ...P..LL.. .-G.FY.MA. .AG....... ---------- ----------   250

MRP1    (1308-155)   ---------- ---------- -                                  1531
cMOAT   (1315-1545)  ---------- ---------- -                                  1545
MRP3    (262-485)    ---------- ---------- -                                   485
38091.aa MRP4        HMVTNTSNGQ PSTLTIFETA L                                   176
MRP5                 ---------- ---------- -                                   222
MRP6    (1178-1401)  ---------- ---------- -                                  1401

Consensus            ---------- ---------- -                                   271
```

FIG. 11

| NCBI | BLAST Search Results | Enter | ? |

Reference: Altschul, Stephen F., Warren Gish, Webb Miller, Eugene W.
Myers, and David J. Lipman (1990). Basic local alignment search tool. J. Mol.
Biol. 215:403-10

Query = MRP4 Polypeptide Choice 1  (aa100-119)
(20 letters)

Database: Non-redundant GenBank CDS
translations+PDB+SwissProt+SPupdate+PIR
285,190 sequences; 85,415,576 total letters.
Searching..................................................done Sequences producing High-scoring Segment Pairs:

```
                                                            Smallest Sum
                                                       High  Probability
                                                      Score   P(N)      N
ai|2439972  (U83660) multidrug resistance-associ...    102  3.9e-06    1
pir||s64800           probable membrane protein YLL048c -.  66   0.22      1
sp|P36171|Yk84_YEAST PROBABLE ATP-DEPENDENT TRANSPORTER Y.. 61   0.68      1
pir||A32126           155K membrane glycoprotein - goat (f.. 58   0.94      1
``` ai|2439972  (U83660) multidrug resistance-associated protein homolog
            [Homo Sapiens]
            Length = 162

Score = 61 (27.0 bits), Expect = 1.1, P = 0.68
Identities = 9/19 (47%), Positives = 15/19 (78%)

Query:    2  GRLKEYDEPYVLLQNKESL  20
             GR+KEYD PY L+ ++ ++
Sbjct:  262  GRVKEYDHPYTLISDRNTI  280 pir||A32126  155K membrane glycoprotein - goat (fragments)
             Length = 104

Score = 58 (25.7 bits), Expect = 2.8, P = 0.94
Identities = 10/15 (66%), Positives = 14/15 (93%)

Query:    3  RLKEYDEPYVLLQNK  17
             +L+EYD+P+VLL NK
Sbjct:   12  KLEEYDKPHVLLHNK  26

Parameters:
V=100
B=50
H=0

Lambda     K      H
 0.307   0.133  0.355

Cutoff to enter 2nd pass:  >=  36  (0.0 bits)

E      S     T1    T2    X1    X2    W    Gap
      10.0   58    11    11    11   -16   -23   40    50

FIG. 12A

```
Database: Non-redundant GenBank CDS translations+PDB+SwissProt+SPupdate+PIR
Posted date:  Jan 21, 1998  7:53AM
# of letters in database: 85,415,576
# of sequences in database:  285,190

Number of Hits to DB:                         1st pass: 3105475, 2nd pass: 15562
Number of Sequences:                          1st pass: 285190,  2nd pass:   430
Number of extensions:                         1st pass: 27037,   2nd pass: 11491
Number of successful extensions:              1st pass: 430,     2nd pass:   857
Number of sequences better than 10:  4
```

```
Score = 102 (45.2 bits), Expect = 3.9e-06, P = 3.9e-06
Identities = 20/20 (100%), Positives = 20/20 (100%)

Query:    1  SGRLKEYDEPYVLLQNKESL   20
             SGRLKEYDEPYVLLQNKESL
Sbjct:   95  SGRLKEYDEPYVLLQNKESL  114 pir|S64800  probable membrane protein YLL048c - yeast (Saccharomyces
            cerevisiae) gnl|PID|e245758 (Z73153) ORF YLL048c (Saccharomyces
            cerevisiae)
            Length = 1661

Score = 66 (29.2 bits), Expect = 0.24, P = 0.22
Identities = 12/19 (63%), Positives = 15/19 (78%)

Query:    1  SGRLKEYDEPYVLLQNKES   19
             +G +KEYD PY LL NK+S
Sbjct: 1611  AGEVKEYDHPYSLLLNKQS 1629 sp|P36171|YK84_YEAST  PROBABLE ATP-DEPENDENT TRANSPORTER YKR104W
            pir||S38183 probable purine nucleotide-binding protein YKR104w -
            yeast (Saccharomyces cerevisiae) gi|486613 (Z28329) ORF YKR104w
            (Saccharomyces cerevisiae)
            Length = 306
```

FIG. 12B

| | | | | | | |
|---|---|---|---|---|---|---|
|ACTTAAAGAA|ACCATTGAAG|ATCTTCCTGG|TAAAATGGAT|ACTGAATTAG|CAGAATCAGG|60|
|ATCCAATTTT|AGTGTTGGAC|AAAGACAACT|GGTGTGCCTT|GCCAGGGCAA|TTCTCAGGAA|120|
|AAATCAGATA|TTGATTATTG|ATGAAGCGAC|GGCAAATGTG|GATCCAAGAA|CTGATGAGTT|180|
|AATACAAAAA|AAAATCCGGG|AGAAATTTGC|CCACTGCACC|GTGCTAACCA|TTGCACACAG|240|
|ATTGAACACC|ATTATTGACA|GCGACAAGAT|AATGGTTTTA|GATTCAGGAA|GACTGAAAGA|300|
|ATATGATGAG|CCGTATGTTT|TGCTGCAAAA|TAAAGAGAGC|CTATTTTACA|AGATGGTGCA|360|
|ACAACTGGGC|AAGGCAGAAG|CCGCTGCCCT|CACTGAAACA|GCAAACAGG|TATACTTCAA|420|
|AAGAAATTAT|CCACATATTG|GTCACACTGA|CCACATGGTT|ACAAACACTT|CCAATGGACA|480|
|GCCCTCGACC|TTAACTATTT|TCGAGACAGC|ACTGTGAATC|CAACCAAAAT|GTCAAGTCCG|540|
|TTCCGAAGGC|ATTTTCCACT|AGTTTTTGGA|CTATGTAAAC|CACATTGTAC|TTTTTTTTAC|600|
|TTTGGCAACA|AATATTTATA|CATACAAGAT|GCTAGTTCAT|TTGAATATTT|CTCCCAACTT|660|
|ATCCAAGGAT|CTCCAGCTCT|AACAAATGG|TTTATTTTA|TTTAAATGTC|AATAGTTGTT|720|
|TTTTAAAATC|CAAATCAGAG|GTGCAGGCCA|CCAGTTAAAT|GCCGTCTATC|AGGTTTTGTG|780|
|CCTTAAGAGA|CTACAGAGTC|AAAGCTCATT|TTTAAGGAG|TAGGACAAAG|TTGTCACAGG|840|
|TTTTTGTTGT|TGTTTTTATT|GCCCCCAAAA|TTACATGTTA|ATTTCCATTT|ATATCAGGGA|900|
|TTCTATTTAC|TTGAAGACTG|TGAAGTTGCC|ATTTTGTCTC|ATTGTTTTCT|TTGACATAAC|960|
|TAGGATCCAT|TATTTCCCCT|GAAGGCTTCT|TGTTAGAAAA|TAGTACAGTT|ACAACCAATA|1020|
|GGAACAACAA|AAAGGAAAAA|GTTTGTGACA|TTGTAGTAGG|GAGTGTGTAC|CCCTTACTCC|1080|
|CCATCAAAAA|AAAAATGGAT|ACATGGTTAA|AGGATAGAAG|GGCAATATTT|TATCATATGT|1140|
|TCTAAAAGAG|AAGGAAGAGA|AAATACTACT|TTCTCAAAAT|GGAAGCCCTT|AAAGGTGCTT|1200|
|TGATACTGAA|AGACACAAAT|GTGACCGTCC|ATCCTCCTTT|AGAGTTGCAT|GACTTGGACA|1260|
|CGGTAACTGT|TGCAGTTTTA|GACTCAGCAT|TGTGACACTT|CCCAAGAAGG|CCAAACCTCT|1320|
|AACCGACATT|CCTGAAATAC|GTGGCATTAT|TCTTTTTTGG|ATTTCTCATT|TATGGAAGGC|1380|
|TAACCCTCTG|TTGACCGTAA|GCCTTTTGGT|TTGGGCTGTA|TTGAAATCCT|TTCTAAATTG|1440|
|CATGAATAGG|CTCTGCTAAC|GTGATGAGAC|AAACTGAAAA|TTATTGCAAG|CATTGACTAT|1500|
|AATTATGCAG|TACGTTCTCA|GGATGCATCC|AGGGGTTCAT|TTTCATGAGC|CTGTCCAGGT|1560|
|TAGTTTACTC|CTGACCACTA|ATAGCATTGT|CATTTGGGCT|TTCTGTTGAA|TGAATCAACA|1620|
|AACCACAATA|CTTCCTGGGA|CCTTTTGTAC|TTTATTTGAA|NTATGAGTCT|TTAATTTTTC|1680|
|CCTGATGATG|GTGGCTGTAA|TATGTTGAGT|TCAGTTTACT|AAAGGTTTTA|CTATTATGGT|1740|
|TTGAAGTGGA|GTCTCATGAC|CTCTCAGAAT|AAGGTGTCAC|CTCCCTGAAA|TTGCATATAT|1800|
|GTATATAGAC|ATGCACACGT|GTGCATTTGT|TTGTATACAT|ATATTTGTCC|TTCGTATAGC|1860|
|AAGTTTTTTG|CTCATCAGCA|GAGAGCAACA|GATGTTTTAT|TGAGTGAAGC|CTTAAAAAGC|1920|
|ACACACCACA|CACAGCTAAC|TGCCAAAATA|CATTGACCGT|AGTAGCTGTT|CAACTCCTAG|1980|
|TACTTAGAAA|TACACGTATG|GTTAATGTTC|AGTCCAACAA|ACCACACACA|GTAAATGTTT|2040|
|ATTAATAGTC|ATGGTTCGTA|TTTTAGGTGA|CTGAAATTGC|AACAGTGATC|ATAATGAGGT|2100|
|TTGTTAAAAC|GATAGCTATA|TTCAAAATGT|CTATATGTTT|ATTTGGACTT|TGAGGTTAA|2160|
|AGACAGTCAT|ATAAACGTCC|TGTTTCTGTT|TTAATGTTAT|CATAGAATTT|TTAATGAAA|2220|
|CTAAATTCAA|TTGAAATAAA|TGATAGTTTT|NATTTCCAAA|AAAAAAAAA|AAAAA|2275|

Formatted Alignmer

```
38091.aa    AWHEELKETI EDLPGKMDTE LAESGSNFSV GQRQLVCLAR AILRKNQILI    50
MRP4-       ----LKETI EDLPGKMDTE LAESGSNFSV GQRQLVCLAR AILRKNQILI    45
Consensus   ......LKETI EDLPGKMDTE LAESGSNFSV GQRQLVCLAR AILRKNQILI    50

38091.aa    IDEATANVDP RTDELIQKKI REKFAHCTVL TIAHRLNTII DSDKIMVLDS   100
MRP4-       IDEATANVDP RTDELIQKKI REKFAHCTVL TIAHRLNTII DSDKIMVLDS    95
Consensus   IDEATANVDP RTDELIQKKI REKFAHCTVL TIAHRLNTII DSDKIMVLDS   100

38091.aa    GRLKEYDEPY VLLQNKESLF YKMVQQLGKA EAAALTETAK QVYFKRNYFH   150
MRP4-       GRLKEYDEPY VLLQNKESLF YKMVQQLGKA EXXXLTETAK XVYFKRNXXH   145
Consensus   GRLKEYDEPY VLLQNKESLF YKMVQQLGKA E...LTETAK .VYFKRN..H   150

38091.aa    IGHTDHMVTN TSNGQPSTLT IFETAL                              176
MRP4-       IGDXXHMVTN XXNGXXS---------                               162
Consensus   IG...HMVTN ..NG...S.. ......                              176
```

FIG. 17

MDR

```
              1                                                              50
crupgp1       VQILKGLNLK  VQSGQTVALV  GNSGCGKSTT  VQLLQRLYDP  TEGVVSIDGQ
crupgp2       IKILKGLNLK  VQSGQTVALV  GKSGCGKSTT  VQLLQRLYDP  TEGVVSIDGQ
humpgp1       VKILKGLNLK  VQSGQTVALV  GNSGCGKSTT  VQLMQRLYDP  TEGMVSVDGQ
pgprat1b      VKILKGLNLK  VKSGQTVALV  GNSGCGKSTT  VQLLQRLYDP  IEGEVSIDGQ
muspgp        VQILKGLNLK  VKSGQTVALV  GNSGCGKSTT  VQLMQRLYDP  LEGVVSIDGQ
crupgp3       IKILKGLNLK  VQSGQTVALV  GNSGCGKTTT  LQLLQRLYDP  TEGTISIDGQ
humpgp3       VKILKGLNLK  VQSGQTVALV  GSSGCGKSTT  VQLIQRLYDP  DEGTINIDGQ
```

FIG. 19A

MRP

```
                            **  *  **  ***  ****         *    *    *  *  ***
         MRP1     FVLKHINVTI  NGGEKVGIVG  RTGAGKSSLT  LGLFRINESA  EGEIIIDGIN
cMOAT/   MRP2     LVLRGITCDI  GSMEKIGVVG  RTGAGKSSLT  NCLFRILEAA  GGQIIIDGVD
         MRP3     LVLRDLSLHV  HGGEKVGIVG  RTGAGKSSMT  LACSRILEAA  KGEIRIDGLN
         MRP4     ..........  ..........  ..........  ..........  ..........
         MRP5     ........TI  KPKEKIGIVG  RTGSGKSSLG  MALFRLVELS  GGCIKIDGVR
         MRP6     LAVQGVSFKI  HAGEKVGIVG  RTGAGKSSLA  SGLLRLQEAA  EGGIKIDGVP
         HSUR     PVLKHTNALI  SPGQKIGICG  RTGSGKSSFS  LAFFRMVDTF  EGHIIIDGID
```

FIG. 19B

MRP4 PCR Product

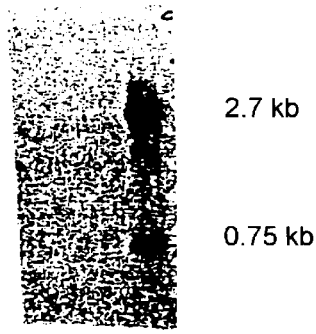

5' Sequence of MRP4 2.7 kb PCR product
Showing a Walker A Motif

```
GTGGGGCGGA CGGAGGCGGG GAAGTCATCA CTGGTAAGTG CCGTGCTCGG          50

NGAATTGGCC CCAAGTCACG GGCTGGTTAG CGTGCATGGA ANAATTGCCT         100

ATGTGTCTCA GCAGCCCTGG GTGTTCTCGG GAACTCTGAG GAGTAATATT         150

TTATTTGGGA AGAAATACGA AAAGGAACGA TATGAAAAAG TCATAAAGGC         200

TTGTGCTCTG AAAAAGGATT TACAGCTGTT GGAGGATGGN GATCTGACTG         250

TGATAGGAGA TCGGNGAACC ACGCTGAGTG GAGGGCNNAA AGCACGGGTA         300

AACCTTGCAA GAGCAGTGTA TCAAGATGCT GACATCTATC TCCTGGACGA         350

TCCTCTCANT GCAAGTANAT GCGGAAGTTA GCANACACTT GTTCGAACTG         400

TGTAATTTGN CANNTTTTGC ATGAGAAGAT CACAATTTTA ATCGACTCAT         450

NAAGTNTGCA AGTACCTCAA AGCTGCAAGT CNNATTCTTG ATANTGAAAG         500

ATGGTAAAAT GGNGCCAAAA NGGNACTTAC ACTTGAGCTT CCTAAAATCT         550

GGNATACAAT TTNGCTTCCT TTTAAANAAA CGATAA                        586
```

FIG. 20

```
Query= M13 For Sequence of 2.7kb MRP4  PCR prod  (5' end seq
       (586 letters)

Database:  Non-redundant GenBank+EMBL+DDBJ+PDB sequences
           344,964 sequences; 722,615,370 total letters Searching..................................................done Smallest
                                                              Sum
                                                    High      Probability
          Sequences producing High scoring Segment Pairs   Score     P (N)

emb|X96393|RNCMRP       R.norvegicus mRNA for canalicular mu...   539    1.8e-34
gb|149379|RATCMOAT      Rattus norvegicus canalicular multis...   539    1.8e-34
db+|D86086|D86086       Rat mRNA for canalicular multispecif...   539    1.8e-34
gb|U66261|CEU66261      Caenorhabditis elegans multidrug res...   469    1.2e-28
gb|AC002411|F20D22      Arabidopsis thaliana chromosome 1 BA...   468    1.5e-28
emb|Y11250|ATMRPPROT    Arabidopsis thaliana mRNA for putati...   465    2.6e-28
gb|U41015|CELF20B6      Caenorhabditis elegans cosmid F20B6       457    1.2e-27
gb|U63970|HSU63970      Human canalicular multispecific orga...   451    3.8e-27
emb|X96395|HSCMRP       H.sapiens mRNA for canalicular multi...   451    3.8e-27
gb|U49248|HSU49248      Human canalicular multispecific orga...   451    3.8e-27
emb|Z48179|SC9302X      S.cerevisiae chromosome IV cosmid 9302    426    4.6e-25
gb|L35237|YSCYCF1MRP    Saccharomyces cerevisiae metal resis...   426    4.6e-25
gb|U92650|ATU92650      Arabidopsis thaliana MRP-like ABC tr...   422    9.9e-25
gb|U41554|CELF57C12     Caenorhabditis elegans cosmid F57C12...   284    4.1e-22
emb|X65256|XLCFTRM      X.laevis CFTR mRNA                        381    2.5e-21
gb|U20418|OAU20418      Ovis aries cystic fibrosis transmemb...   358    2.1e-19
gb|M76128|BQVTCRCF      B.taurus cystic fibrosis transmembra...   349    1.2e-18
gb|S82688|S82688        CFTR=cystic fibrosis transmembrane c...   349    1.2e-18
gb|AF013753|AF013753    Macaca mulatta cystic fibrosis trans...   349    1.2e-18
gb|M28668|HUMCFTRM      Human cystic fibrosis mRNA, encoding...   349    1.2e-18
gb|U60209|XLU60209      Xenopus laevis cystic fibrosis trans...   345    2.5e-18
gb|M60493|MUSMCFTR      Mouse cystic fibrosis transmembrane ...   323    1.7e-16
gb|M84613|MUSCFTRY      Mouse cystic fibrosis transmembrane ...   323    1.7e-16
gb|U40227|OCU40227      Oryctolagus cuniculus CFTR chloride ...   322    2.1e-16
gb|M69298|MUSCFTR       Mouse cystic fibrosis transmembrane ...   322    2.1e-16
gb|U33010|SPU33010      Schizosaccharomyces pombe cosmids 35...   303    7.8e-15
gb|AF022908|AF022908    Mus musculus multidrug resistance pr...   292    6.4e-14
gb|M89906|RATCFTR       Rattus norvegicus cystic fibrosis tr...   285    2.5e-13 emb|X96393|ANCMRP  R.norvegicus mRNA for canalicular multidrug resistance protein
          Length = 4909

Plus Strand HSPs:

Score = 539  (148.9 bits), Expect = 1.8e-34, P = 1.8e-34
    Identities = 209/349  (61%), Positives = 209/340  (61%), Strand = Plus / Plus Query:    17 CGGGGAAGTCATCACTGGTAAGTGCCGTGCTCGGNGAATTGGCCCCAAGTCACGGGCTGG    76
              ||||| || || |||||   ||| |||| ||  ||||||         |||||||
Sbjct:  2061 CTGGGAAATCCTCTTTGGTATCAGCCATGCTGGGAGAAATGGAAAACGTTCACGGGCACA  21

Query:    77 TTAGCGTGCATGGAANAATTGCCTATGTGTCTCAGCAGCCCTGGGTGTTCTCGGGAACTC   13
              | | | || |||   |  ||   |||||||| |||||| |||| |||| |    |||||
Sbjct:  2121 TCACCATCCAGGGATCCACAGCCTATGTCCCTCAGCAGTCCTGGATTCAGAATGGAACCA  21

Query:   137 TGAGGAGTAATATTTTATTTGGGAAGAAATACGAAAAGGAACGATATGAAAAAGTCATAA   19
              | |   ||  ||   | |||||||| || ||    |  ||   |  | |||| |   |
Sbjct:  2181 TCAAAGACAACATCCTGTTTGGGTCCGAATACAATGAAAAGAAGTACCAGCAAGTTCTCA  22

Query:   197 AGGCTTGTGCTCTGAAAAAGGATTTACAGCTGTTGGAGGATGGNGATCTGACTGTGATAG   25
              | || ||  || ||   |  |||   ||   ||  | | |   |  | |  | || | |
Sbjct:  2241 AAGCATGCGCTCTCCTCCCAGACTTGGAAATATTGCCTGGAGGAGACATGGCTGAGATCG  23

Query:   257 GAGATCGGNGAACCACGCTGAGTGGAGGGCNNAAAGCACGGGTAAACCTTGCAAGAGCAG   31
              |||| ||  | |     |  | ||||      ||  ||| ||   || ||   ||| |
Sbjct:  2301 GAGAGAAGGGGATAAATCTCAGTGGTGGTCAGAAGCAGCGAGTCAGCCTGGCCAGAGCTG  23

Query:   317 TGTATCAAGATGCTGACATCTATCTCCTGGACGATCCTCT                      356
              || ||||||||||||||||||||| | |||||||||| |
Sbjct:  2361 CCTATCAAGATGCTGACATCTATATTCTGGACGATCCCCT                     2400
```

FIG. 21

MRP4 is Abundantly Expressed in Many Tumor Cells

← 6.5 kb

HL60 | Hela | K562 | Molt4 | RAJI | SW480 | Lung A459 | Melanoma

MRP4 Expression is Down-regulated by
p53 in K562 Erytholeukemia Cells

Temp (°C): 32  37   32  37   32  37   + control
Time:       24h     24h      48h
Cells:      K562vc    K562143p53

PMEA Resistant CEM Cell Lines Have Increased MRP4 Gene Copy and Expression
FIG. 25A
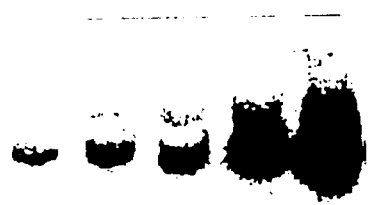
CEM | 0.4  2.0  10.0  50.0
PMEA (mM)
FIG. 25B
← MRP4
CEM | 0.4  2.0  10.0  50.0
PMEA (mM)
FIG. 25C
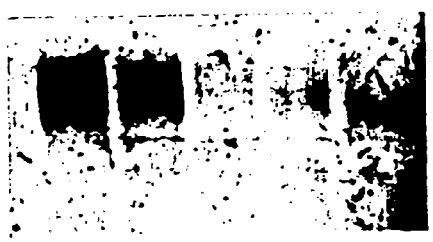
← MRP4
← MRP1
CEM | 50.0  10.0  2.0  0.4
PMEA (mM)

MRP4 Antibody Reveals MRP4 is Selectively Increased in PMEA Resistant CEM Cells

PMEA Resistant CEM Cell Lines Have Increased MRP4 Gene Copy and Expression
FIG. 28A
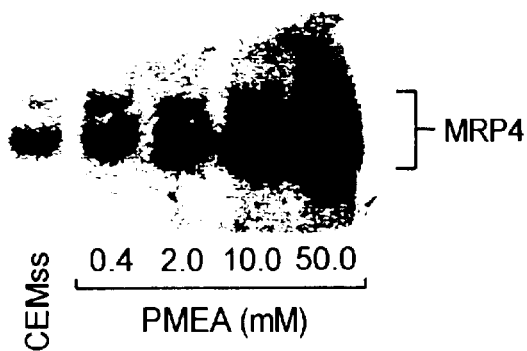
FIG. 28B
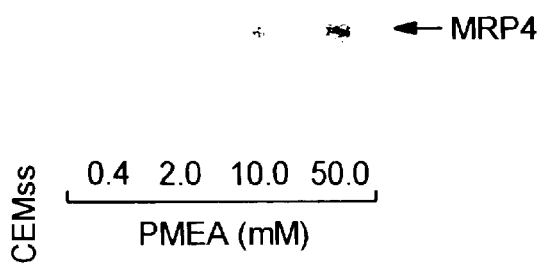
FIG. 28C
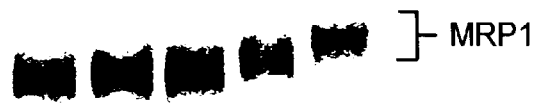
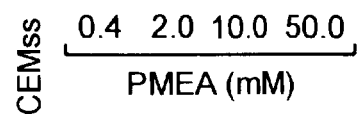

MULTIDRUG RESISTANCE ASSOCIATED PROTEINS AND USES THEREOF

GOVERNMENTAL SUPPORT

This invention was made with the support of National Institutes of Health Grant Nos.: ES/GM05851 and NIH A127652. The United States government may have certain rights to this invention.

Throughout this application, certain publications are referenced by number. Full citations for these publications may be found listed at the end of the specification and preceding the Claims. The disclosures of these publications in their entireties are hereby incorporated by reference into this application in order to more fully describe the state of the art. A Sequence Listing is provided.

FIELD OF THE INVENTION

The present invention relates generally to to multi-drug resistance, and more particularly to materials such as multi-drug resistant proteins (MRP), and to possible diagnostic and therapeutic uses thereof. The invention further relates to methods for identifying treatments refractive to drug resistance.

BACKGROUND OF THE INVENTION

Microbial and cellular resistance to drug therapy is a major and long-standing problem to the treatment of disease and infection, including cancer. Cross-resistance between different anti-microbial and anti-cancer agents, which are structurally and functionally distinct, is a relatively common phenomenon called multi-drug resistance (MDR).

With respect to cancers, some malignant tumors respond poorly to chemotherapy, indicating that the target cells are intrinsically resistant. Other tumors initially respond well to chemotherapy, but appear to develop resistance, indicating a selection process or cellular response to the chemotherapeutic agent(s). The broad-spectrum resistance characteristic of MDR, therefore, is of great clinical significance.

MDR was initially described in cultured tumor cells which following selection for resistance to a single anti-tumor agent became resistant to a range of chemically diverse anti-cancer agents (52). These MDR cells exhibited a decrease in intracellular drug accumulation due to active efflux by transporter proteins. The so-called "multi-drug transporters" are membrane proteins capable of expelling a broad range of toxic molecules from the cell (53). These multi-drug transporters belong to the ATP-binding cassette (ABC) superfamily of transport proteins that utilize the energy of ATP hydrolysis for activity (53, 57). In microorganisms, multi-drug transporters play an important role in conferring antibiotic resistance on pathogens.

Several mechanisms have been described as responsible for MDR. The most well characterized gene conferring drug resistance by an ATP-dependent efflux mechanism is the MDR1 gene product, P-glycoprotein (Pgp). a member of the ABC cassette family of transporters. Pgp removes hydrophobic drugs of diverse chemical structures from cells as an efflux pump (55).

Another transporter protein, capable of conferring drug resistance, the multi-drug resistance protein (MRP), has been identified in a number of MDR human tumor cell lines that do not appear to express Pgp (52). The presence of MRP at the cell surface of such cells has been associated with alterations in drug accumulation and distribution (52). Expression of MRP causes a form of multi-drug resistance similar to that conferred by Pgp (52). The two proteins, however, are only distantly related. MRP has also been shown to be a primary active transporter of a structurally diverse range of organic anionic conjugates. Like Pgp, MRP has a broad substrate specificity. In addition to hydrophobic compounds, MRP is able to transport metallic oxyanions and glutathione and other conjugates, including peptidyl leukotrienes (52). This is in contrast to Pgp. (Stride, B D, et al., 1997, Mol. Pharmacol., 52:344–53). The mechanism by which MRP transports these compounds and mediates multi-drug resistance is not understood. In addition, topoisomerase II has been associated with MDR. Like Pgp, MRP is expressed in normal human tissues in addition to tumor cells (52). In normal cells, MRP appears to be located within the cytoplasm, indicating that it may function differently in normal cells as compared with tumor cells (52). Homologs of human Pgp and MRP have been found in microorganisms such as Plasmodium falciparum, candida albicans, Saccharomyces cerevisiae and Lactococcus lactis (53).

Although MDR1 was cloned some time ago, proteins in animal cells that were functionally similar were not readily identified. MRP has been described which in some cell types confer a drug resistance phenotype similar to the MDR1 gene (58). The prototype MRP1 gene was first described in 1992. Subsequently, MRP2 (cMOAT) was cloned. Both MRP1 and MRP2 act to efflux anionic compounds, including drugs or endogenous compounds. Several yeast MRP homologues have been identified (49) and recently, additional human homologues have been identified in the EST databases. Particularly, Borst and colleagues searched the EST database and identified four additional family members (MRP2, MRP3, MRP4, and MRP5). Nonetheless, the human MRP homologues have until now remained functionally undefined. MRP3 has been described as exhibiting high expression in some cell lines but not in others, with overexpression of MRP3 in resistant lines being identified in several doxorubicin-resistant and cisplatin-resistant cell lines (49). MRP5 was identified as being very widely expressed. MRP4 in contrast to MRP3 and MRP5, was not reportedly overexpressed in any cell line analyzed (49). Importantly, the EST-based primary MRP4 sequence determined lacks several crucial pieces of information including: (1) a classic Walker A motif which is a signature of the ATP-binding domain found in ABC cassette transporter members; (2) more than 90% of the protein sequence; and (3) any functional marker. MRP3, MRP4 and MRP5 have been localized to a different chromosome than MRP1 and MRP2, indicating that they are not merely alternative splicing products (49).

ABC transporters are integral membrane proteins involved in ATP-dependent transport across biological membranes. Members of this superfamily play roles in a number of phenomena of biomedical interest, including cystic fibrosis (CFTR) and multi-drug resistance. Many ABC transporters are predicted to consist of two functional domains, a membrane-spanning domain and a cytoplasmic domain. The latter contain conserved nucleotide-binding motifs with the former containing substrate binding or recognition sites. Attempts to determine the structure of ABC transporters and of their separate domains have not yet been successful (57).

The ABC transporters of glutathione S-conjugates and related amphiphilic anions have been identified as MRP1 and MRP2. These 190-kDa membrane glycoproteins have been cloned. MRP1 and MRP2 have been shown to be unidirectional, ATP-driven, export pumps with an amino acid identity of 49% in humans. MRP1 is detected in the plasma membrane of many cell types, including erythrocytes. MRP2, also known as canalicular MRP (cMRP) or canalicular multispecific organic anion transporter (cMOAT), has been localized to the apical domain of polarized epithelia, such as the hepatocyte canalicular membrane and kidney proximal tubule luminal membrane. Physiologically important substrates of both transporters include glutathione S-conjugates, such as leukotriene C4, as well as bilirubin glucuronides, 17β-glucuronosyl estradiol and glutathione disulfide. Both transporters have been associated with multiple drug resistance of malignant tumors because of their capacity to pump drug conjugates and drug complexes across the plasma membrane into the extracellular space. The substrate specificity of MRP1 and MRP2 studied in inside-out oriented membrane vesicles is very different from MDR1 (Pgp). MRP1 and MRP2 have been called conjugate transporting ATPases, functioning in detoxification and, because of their role in glutathione disulfide export, in the defense against oxidative stress (54).

A cDNA encoding another ATP-binding cassette transporter, MOAT-B, has been reportedly cloned and mapped (56). Comparison of the MOAT-B predicted protein with other transporters revealed that it is most closely related to MRP. cMOAT, and the yeast organic anion transporter YCF1. Although MOAT-B is closely related to these transporters, it is distinguished by the absence of a approximately 200 amino acid $NH_2$-terminal hydrophobic extension that is present in MRP and cMOAT and which is predicted to encode several transmembrane spanning segments. In addition, the MOAT-B tissue distribution is distinct from MRP and cMOAT. In contrast to MRP, which is widely expressed in tissues, including liver, and cMOAT, the expression of which is largely restricted to liver, the MOAT-B transcript is widely expressed, with particularly high levels in prostate, but is barely detectable in liver. (6).

The sequence and structural similarity between eukaryotic and prokaryotic ABC transporters is striking. The sequence similarity extends beyond the conserved components (the nucleotide-binding sequence motif, i.e. Walker motifs, and the ABC signature sequence) and includes several hundred amino acids on either side of the Walker motifs. Functionally, this suggests conservation between the coupling of ATP binding and ATP hydrolysis, with both processes necessary to facilitate substrate transport. The functional conservation is observed from prokaryotic to eukaryotes even though the substrates may be markedly different. Further evidence that the ABC transporters can be grouped together is found in an analysis of their predicted secondary structures which shows these molecules possess remarkably similar secondary structures across the entire phylogenetic spectrum of ABC transporters.

The recently completed sequence of the yeast genome revealed that over 29 proteins belong to the ABC transporter family (59). Despite the sequence and structural similarity a diverse array of substrates and functions are attributed to the ABC transporters. For example, in S. cerevisiae, the STE6 protein is necessary for the secretion of essential mating protein, α-factor; in D. melanogaster, the white and brown gene products may transfer pigment proteins: in mammals, MRP1 transports some cancer therapeutic agents and glutathione conjugates; and CFTR serves as a ion channel. Thus, it is clear that simply being a member of the large ABC transport family does not in any way define the type of substrate transported nor does a predicted secondary structure. Further, many of the substrates transported are structurally diverse and do not share clearly definable molecular signatures.

Antiviral therapies used to treat HIV and other DNA virus infections include acyclic nucleoside phosphonates. These represent a new class of nucleotide analogs that exhibit potent and selective activity against a variety of both DNA and RNA viruses, including the human immunodeficiency virus and hepatitis B virus.

The acyclic nucleoside phosphonate PMEA (9-(2phosphonylmethoxyethyl)adenine) is a broad-spectrum agent that exhibits potent antiviral activity against various DNA viruses and retroviruses, including HIV (1–14). PMEA and its lipophilic prodrug bispom-PMEA (15) have entered phase I clinical trials as treatment for HIV infections (6.17). PMEA acts as a stable monophosphate analog of AMP and dAMP, and its antiviral activity is thought to require activation to the diphosphate derivative PMEApp, which then acts to inhibit viral DNA polymerases with relative sparing of cellular DNA replication (8, 11, 18). However, the exact mode of metabolism and action of PMEA and related acyclic phosphonate analogs remains unclear. Studies have suggested that PMEA enters cells via endocytosis and is further metabolized to PMEAp and PMEApp by cellular enzymes (19). One report suggested that the anabolism of PMEA may involve direct conversion to PMEApp via PRPP synthetase, although direct evidence for this mechanism in intact cells has not been obtained (11).

Sequential intracellular phosphorylation of the nucleoside and phosphonate analogs is essential for the bioactivation of these compounds (6–8). The phosphorylated metabolites function as anti-HIV drugs by inhibiting the reverse transcriptase (RT) enzyme of HIV. It has been well documented that achieving optimal intracellular concentrations of the phosphorylated biotransformation products is important for exerting the anti-viral effect (9, 10).

For a clinically efficacious treatment of HIV infection, tong-term use of the nucleoside RT inhibitors is a very common practice. The development of drug resistance to these compounds is well documented in the literature. Several reasons for the development of drug resistance have been observed: (i) These nucleoside analogs and the acyclic nucleoside phosphonates select for various mutations in the RT that confers varying degrees of viral resistance to the different analogs (11, 12). (ii) A decrease in the enzymes involved in the biotransformation of the drug to the active metabolite leads to cellular resistance (13). (iii) A change in the transport of the drug, either decreased uptake or increased flux such that optimal intracellular levels are not attained could lead to cellular resistance (48).

Because PMEA is a nucleotide analog which enters cells by a nonspecific process of endocytosis, decreased cellular influx is unlikely as a mode of cellular resistance. Nevertheless, studies have revealed that resistance to PMEA and similar compounds (e.g. AZT) appears secondary to decreased intracellular accumulation, thus limiting the therapeutic effectiveness of these compounds. Moreover, different T-cell lines do not achieve comparable intracellular concentrations of these compounds despite comparable extracellular concentrations.

These findings are consistent with the suggestion that intracellular accumulation may negatively impact pharmacologic antiviral therapeutic efficacy and imply enhanced transport of these compounds out of the cell as an important unrecognized mechanism in therapeutic failure. Accordingly, the identification of inhibitors and substrates associated with drug efflux and the development of strategies for controlling this activity, would therefore be expected to have substantial therapeutic impact, and it is toward the fulfillment of this and other like objectives that the present invention is directed.

SUMMARY OF THE INVENTION

In its broadest aspect, the present invention relates to a protein hereinafter referred to and exemplified by multi-drug resistance protein 4 (MRP4), and extends to nucleic acid molecules encoding it, cells that express it, and to its variants, including conserved variants, antagonists including antibodies, analogs, and mimics, including small molecules.

The invention further relates to finding respecting the role of MRP4 in drug efflux particularly in humans, and to the diagnostic and therapeutic applications of this activity, such as the ability to enhance and extend drug and like therapies where efficacy is dependent upon the development and maintenance of consistent, high intracellular levels of the therapeutic agent. In such event, the invention extends to, e.g. methods for administering anti-cancer or anti-HIV therapeutic agents, which methods include modulating the expression of MRP4 and/or administering antagonists or other agents that suppress the drug efflux activity of MRP4.

Further, the invention extends to the novel human T cell line. termed CEMr-1 has been generated which expresses a multi-drug-resistant phenotype to a variety of unrelated clinically active anti-HIV nucleoside agents such as zidovudine (AZT), lamivudine (3TC), and the acyclic phosphonate analogs such as PMEA and PMPA. (48). This multi-drug-resistant phenotype is associated with an ATP-dependent efflux of the mono phosphorylated congeners from these cells. These results suggested the involvement of an efflux pump similar to those described for many cancer drugs. However, biochemical characterization of the resistant cells revealed that the known P-glycoprotein pump was not responsible for drug efflux in CEMr-1 cells As stated above, the present invention further extends to and provides a method for modulating drug resistance by controlling the presence, activity and/or the expression of MRP4, its mimics, antagonists, analogs, congeners, active fragments, conserved variants, and mixtures. The present invention represents the first example of a role of MRP4 in drug resistance. Moreover and as stated above, these results suggest that MRP4 functions as an organic anion transporter that is capable of effluxing nucleoside analogs and other drugs with anionic functionality. Indeed this represents the first mammalian pump described for nucleoside analogs with anionic functionality (i.e. all analogs with a purine and pyrimidine selection). It is expected that certain patients who either develop resistance to therapy without displaying viral resistance may develop cellular resistance by this mechanism. Alternatively, variation between individual's MRP4 expression may determine therapeutic efficacy.

The present invention discloses that MRP4 functions as a drug efflux protein. MRP4 antibodies are also disclosed by the instant invention, and their diagnostic and therapeutic use is also contemplated.

MRP4 may represent the first gene described in mammals that effluxes intracellular nucleotides, thus representing an important molecule regulating nucleotide balance within cells, with therapeutic relevance.

It is another object of the present invention to provide an antibody capable of specifically binding to the provided protein without substantially cross-reacting with non MRP4 proteins or homologs thereof under conditions permissive to antibody binding.

Also an object of the present invention is to provide a diagnostic kit for identifying individuals resistant to anti-retroviral agent therapy comprising the provided probe or antibody.

It is also an object of the present invention to provide a kit for identifying a compound which is refractive to MRP4 efflux comprising the provided probe.

It is an object of the present invention to provide a nucleic acid probe capable of specifically hybridizing with the provided nucleic acid.

Additionally, it is an object of the present invention to provide a method of identifying the provided MRP4 protein in a sample.

It is a further object of the present invention to provide a method for identifying a nucleic acid in a sample which encodes MRP4 protein.

Still a further object of the present invention is to provide a method for identifying a compound that modulates expression of MRP4.

Further still, it is an object of the present invention to provide a method for identifying a compound capable of modulating MRP4 protein activity.

Also an object of the present invention is to provide a method of modulating MRP4 protein activity in a sample, comprising contacting the sample with the modulator compound identified by the provided method.

Yet another object of the present invention is to provide a pharmaceutical composition which comprises the identified modulator compound and a pharmaceutically acceptable carrier.

Still a further object of the present invention is to provide a method for treating a condition in a subject which comprises administering to the subject an amount of the provided pharmaceutical composition, effective to treat the condition in the subject.

A further still object of the present invention is to provide a method for identifying subjects at risk for resistance to anti-microbial agent therapy.

Yet another object of the present invention is to provide a method for identifying an anti-microbial agent which is refractive to MRP4 efflux activity.

It is still further object of the present invention to provide a transgenic non-human animal whose somatic and germ cells contain and express a gene encoding MRP4 protein, the gene having been introduced into the animal or an ancestor of the animal at an embryonic stage and wherein the gene may be operably linked to an inducible promoter element.

Other objects and advantages will become apparent to those skilled in the art from a consideration of the ensuing description which proceeds with reference to the illustrative drawings.

BRIEF DESCRIPTION OF THE DRAWINGS

FIG. 11. Multiple sequence alignment of C-terminus of MRP family members permits the identification of possible unique MRP4 peptide fragments for antisera development. MRP1 (SEQ.ID.NO.:21), MRP2 (CMOAT) (SEQ.ID.NO.:22), MRP3 (SEQ.ID.NO.:23), MRP5 (SEQ.ID.NO.:24), MRP6 (SEQ.ID.NO.:25), MRP4 (38091aa) (SEQ.ID.NO.:2).

FIG. 12. GenBank databank analysis identifies that the peptide SGR LKE YDE PYV LLQ NKE SL (SEQ ID NO.:4) is potentially useful for anti-sera development.

FIG. 15. The MRP4 EST (Genbank Accession R35798) was entirely sequenced (SEQ. ID. NO.:1) and found to contain an open reading frame of 171 amino acids representing the C-terminus of MRP4.

FIG. 16. The MRP4 EST (Genbank Accession R35798) was translated in the three forward reading frames (SEQ.ID.NO.:30, SEQ.ID.NO.:31, SEQ.ID.NO.:32) to identify the longest open reading frame (ORF). The two additional sequences show divergence from other published sequence ORF fragments from the same clone.

FIG. 17. Alignment between sequenced MRP4 regions reveals a region of sequence divergence (SEQ ID NO.:3), (SEQ ID NO.:12).

FIGS. 19A–19C. Use of a degenerate oligonucleotide strategy to obtain a much larger portion of the MRP4 cDNA. The conserved VGRTGAKSS (SEQ.ID.NO.:16) sequence is used to generate degenerate oligonucleotides. (A) The multiple sequence alignment shows among the p-glycoprotein family members (SEQ.ID.NO.:9, SEQ.ID.NO.:10, SEQ.ID.NO.:11, SEQ.ID.NO.:17, SEQ.ID.NO.:18, SEQ.ID.NO.:19, SEQ.ID.NO.:20) the conservation of the Walker A motif (G(X4)GKS) (SEQ ID NO.:13). (B) The multiple sequence alignment of the ORFs of the MRP family members reveals that MRP4 does not contain a Walker A while other MRP ESTs contain the Walker A. (C) Result of PCR amplification using walker A and MRP4 specific oligonucleotides of the MRP4 product from CEM-r1.

FIG. 20. Sequence analysis reveals the presence of Walker A in MRP4 amplified sequence, (SEQ ID NO.: 14). The position of the Walker A motif is at the 5' end region of the 2.7 kb fragment.

FIG. 21. A Genbank database search reveals that the MRP4 sequence is highly related to another MRP family member, cMOAT (aka, MRP2) (SEQ ID NO.: 15).

FIGS. 25A–C. PMEA Resistant CEM Cell Lines Have Increased MRP4 Gene Copy and Expression. (A) Southern blot, (B) RNAse protection assay, (C) Western Blot.

FIG. 28. Amplification and overexpression of MRP4 in CEMss cells selected for PMEA resistance. Individual PMEA resistant CEM cell lines were developed from CEMss cells by step-wise to exposure to increasing concentrations of 0.4, 2, 10 and 50 mM PMEA. (A) Southern blot analysis was performed on genomic DNA (10 ug) isolated from the indicated PMEA resistant cell lines and hybridized with MRP4. (B) 10 ug of total RNA from the same cell lines were analyzed by RNAse protection. (C) Immunoblot analysis of MRP4 and MRP1 was performed on total cell lysates of the same cells.

DETAILED DESCRIPTION OF THE INVENTION

Figure 1:
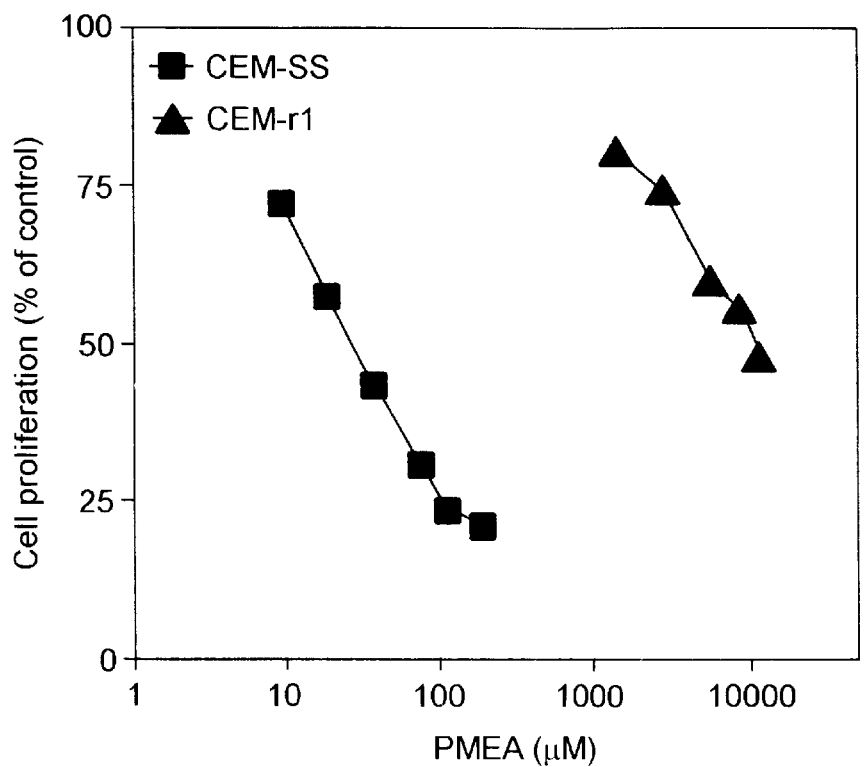
FIG. 1. Cytostasis (inhibition of cell proliferation) of PMEA in CEM-SS and CEM-r1 cells. Exponential cultures were incubated with PMEA, and the increases in cell numbers were monitored after 48-hr incubations, using a Coulter counter, as described herein. The results are the mean from two independent experiments done in duplicate.

The present invention provides an isolated nucleic acid encoding a multi-drug resistance protein 4 (MRP4) or a portion thereof. An embodiment according to this invention is an isolated multi-drug resistance protein 4 (MRP4) nucleic acid having the following characteristics: (1) encoding an MRP4 protein; and (2) the ability to hybridize under standard hybridization conditions to the sequence shown in SEQ. ID.No. :1 or a portion thereof. An embodiment of the present invention is the provided nucleic acid comprising SEQ.ID.No.:1 or a portion thereof.

According to an embodiment of the present invention the nucleic acid is selected from the group consisting of DNA, RNA, and cDNA. Another embodiment of the present invention is a vector comprising the provided nucleic acid. According to still another embodiment of this invention, the vector comprises viral or plasmid DNA. Still another embodiment of the present invention is an expression vector comprising the provided nucleic acid and regulatory elements. As additional embodiment of the present invention provides a host vector system which comprises the provided expression vector in a suitable host. The present invention additionally provides a vector, comprising cDNA encoding MRP4. According to yet another embodiment of the present invention the suitable host is selected from the group consisting of a bacterial cell, a eukaryotic cell, a mammalian cell and an insect cell.

The present invention also provides an isolated MRP4 protein or a portion thereof. According to one embodiment of the present invention, MRP4 has substantially the same amino acid sequence as shown in SEQ.ID.No.: 2.

The present invention additionally provides a nucleic acid probe capable of specifically hybridizing with the provided nucleic acid. According to an embodiment of this invention, the probe is capable of specifically hybridizing with a nucleic acid selected from the group consisting of SEQ.ID.No:5, SEQ.ID.No:6, SEQ.ID.No:7, and SEQ.ID.No:8.

Also, the present invention provides an antibody capable of specifically binding to the provided protein without substantially cross-reacting with non-MRP4 proteins or homologs thereof under conditions permissive to antibody binding. An embodiment of this invention is a cell capable of producing the provided antibody. Additionally, the present invention provides a method of identifying the provided MRP4 protein in a sample comprising: a) contacting the sample with the provided antibody under conditions permissive to the formation of a complex between the antibody and the protein; b) determining the amount of complex formed: and c) comparing the amount of complex formed in step (b) with the amount of complex formed in the absence of the antibody, the presence of an increased amount of complex formed in the presence of the antibody indicating identification of the protein in the sample.

The present invention further provides a method for identifying a nucleic acid in a sample which encodes MRP4 protein which comprises: (a) contacting the sample with the provided nucleic acid probe under conditions permissive to the formation of a complex between the nucleic acid probe and the nucleic acid encoding the MRP4 protein in the sample: (b) determining the amount of complex formed in step (a); and (c) comparing the amount of complex determined in step (b) with the amount of complex formed using an arbitrary sequence, a greater amount of complex formed with the MRP4-specific probe indicating the presence of a nucleic acid encoding a MRP4 protein in the sample. An embodiment of the present invention is further comprising amplifying the nucleic acid molecule encoding the MRP4 protein under conditions suitable for polymerase chain reaction. According to yet another embodiment of this invention, the amplified nucleic acid molecule encoding MRP4 is detected by size fractionation. According to still another embodiment, the probe is labeled with a detectable marker. According to a further embodiment, the detectable marker is a radiolabeled molecule, a fluorescent molecule, an enzyme, a ligand, or a magnetic bead. Still further, an embodiment of this invention provides an isolated nucleic acid, previously unknown, identified by the provided method.

Still further, the present invention provides a method for identifying a compound that modulates expression of MRP4 comprising: (a) contacting a sample which expresses MRP4 with the compound; (b) determining the amount of expression of MRP4 protein in the sample; and (c) comparing the amount of MRP4 protein expression determined in step (b) with the amount determined in the absence of the compound. Also the present invention provides a compound, previously unknown, identified by the provided method.

According to an embodiment of the present invention the sample is selected from the group consisting of cell lysate, a cell-free translation expression system, an isolated cell and a cultured host cell.

Further still, the present invention provides a method for identifying a compound capable of modulating MRP4 protein activity comprising: (a) contacting a sample which expresses MRP4 protein with the compound; (b) determining the amount of MRP4 protein activity in the sample; and (c) comparing the amount of MRP4 protein activity determined in step (b) with the amount determined in the absence of the compound, an increase or decrease in activity indicating the presence of a compound capable of modulating the MRP4 protein activity. An embodiment of this invention is step (a) comprising first introducing the nucleic acid encoding a MRP4 protein into an expression system and causing the expression system to express the nucleic acid under conditions whereby a MRP4 protein is produced. According to a further embodiment of this invention, step (b) comprises measuring the efflux of an antimicrobial agent from a cell in the presence of the compound. According to a still further embodiment, the agent is selected from the group consisting of nucleoside inhibitors and protease inhibitors. According to yet a further embodiment, the agent is selected from the group consisting of antiviral agents such as azidothymidine (AZT), acyclovir and gancyclovir. According to yet another embodiment, the agent is selected from the group consisting of anti-neoplastic agents, such as AraC, Adenine arabinoside (Ara-A), 2-Chlorodeoxyadenosine (2-CDA), 2-fluoroarabinosyladenine and gemcitabine. The present invention further provides a compound, previously unknown, identified by the provided method.

According to an embodiment of the present invention the sample is selected from the group consisting of cell lysate, a cell-free translation expression system, an isolated cell and a cultured cell. According to still yet another embodiment, the compound is a peptide, a peptidomimetic, a nucleic acid, a polymer, or a small molecule. According to still yet a further embodiment, the compound is bound to a solid support.

The present invention still further provides a method of modulating MRP4 protein activity in a sample, comprising contacting the sample with the compound identified by the provided method.

The present invention yet still further provides a pharmaceutical composition which comprises the identified compound and a pharmaceutically acceptable carrier. According to an embodiment of this invention, the carrier is a diluent, an aerosol, a topical carrier, an aqueous solution, a nonaqueous solution or a solid carrier.

Still further, the present invention provides a method for treating a condition in a subject which comprises administering to the subject an amount of the provided pharmaceutical composition, effective to treat the condition in the subject. According to an embodiment of this invention, the condition is selected from the group consisting of an infectious, immunodeficiency, neurological, renal, pulmonary, hepatic, cardiovascular, neoplastic and malignant condition. According to still a further embodiment of this invention, the condition is a result of virus, bacterial, or yeast infection.

Further still, the present invention provides a method for identifying subjects at risk for resistance to anti-microbial agent therapy comprising: (a) identifying by the provided method, the presence of MRP4 in a sample from the subject; (b) measuring the amount of MRP4 present in the sample from the subject; (c) comparing the amount of MRP4 present in a control sample having an amount of MRP4 which does not indicate resistance to drug therapy, an elevated amount of MRP4 present in the sample from the subject indicating increased risk for resistance to drug therapy in the subject.

Yet further still, the present invention provides a method for identifying an anti-microbial agent which is refractive to MRP4 efflux activity comprising: (a) contacting a cell expressing MRP4 with the agent: (b) measuring the amount of agent in the cell; (c) incubating the cell with the agent; and (d) comparing the amount of agent in the cell before and after the incubation of step (c) no substantial decrease in the amount of the agent in the cell after the incubation of step (c) indicating an agent which is refractive to MRP4 efflux activity. An embodiment of this invention is step (a) further comprising labeling the agent with a detectable marker. According to another embodiment of this invention, the detectable marker is a radiolabeled molecule, a fluorescent molecule, an enzyme, a ligand, or a magnetic bead. The present invention also provides the agent identified by the provided method. Yet another embodiment of this invention is a pharmaceutical composition comprising the agent and a pharmaceutically acceptable carrier.

Even further still, the present invention provides a transgenic non-human animal whose somatic and germ cells contain and express a gene encoding MRP4 protein the gene having been introduced into the animal or an ancestor of the animal at an embryonic stage and wherein the gene may be operably linked to an inducible promoter element. According to one embodiment of this invention, the transgenic animal is a mouse. According to another embodiment of this invention, the gene encoding MRP4 is overexpressed. According to still another embodiment, the transgenic animal is a knockout, comprising a genetic mutation which substantially reduces expression of MRP protein under normal conditions. A still further embodiment of this invention is a cell isolated from the transgenic animal. Further even still, the present invention provides a method of identifying an antimicrobial agent which is refractive to MRP4 efflux comprising the steps of: (a) contacting the cell isolated from the transgenic animal with the agent; (b) measuring the amount of agent in the cell; (c) incubating the cell with the agent; (d) comparing the amount of agent in the cell before and after the incubation of step (c) no substantial decrease in the amount of the agent in the cell after the incubation of step (c) indicating a agent which is refractive to MRP4 efflux. According to yet still another embodiment of this invention, the transgenic animal overexpresses MRP4 protein.

Finally, the present invention provides a kit for identifying a compound which is refractive to MRP4 efflux comprising the provided probe. Also the present invention provides a diagnostic kit for identifying individuals resistant to antiretroviral agent therapy comprising the provided probe, and/or antibody. According to an embodiment of this invention, the diagnostic kit further comprises nucleoside analogs or antibodies.

Antibodies including both polyclonal and monoclonal antibodies, and drugs that modulate the production or activity of MRP4 and/or subunits thereof, may possess certain diagnostic applications and may for example, be utilized for the purpose of detecting and/or measuring the susceptibility to or presence of MDR in cells or individuals, or with respect to drug refractivity to resistance development.

For example, MRP4 or any subunits thereof, may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic the activity(ies) of MRP4, may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See. e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632: 4,493,890.

Panels or monoclonal antibodies produced against MRP4 or subunits thereof can be screened for various properties: i.e. isotype, epitope, affinity, etc. Of particular interest are monoclonal antibodies that neutralize the activity of MRP4. Such monoclonals can be readily identified in MRP4 activity assays. High affinity antibodies are also useful when immunoaffinity purification of native or recombinant MRP4 is possible.

Preferably, the anti-MRP4 antibody used in the diagnostic methods of this invention is an affinity purified polyclonal antibody. More preferably, the antibody is a monoclonal antibody (mAb). In addition, it is preferable for the anti-antibody molecules used herein be in the form of Fab, Fab', F(ab')$_2$ or F(v) portions of whole antibody molecules.

One diagnostic method of the present invention comprises examining a cellular sample or medium by means of an assay including, an effective amount of an antagonist to a MRP4 protein, such as an anti-MRP4 antibody, preferably an affinity-purified polyclonal antibody, and more preferably a mAb. In addition, it is preferable for the anti-MRP4 antibody molecules used herein be in the form of Fab, Fab', F(ab')$_2$ or F(v) portions or whole antibody molecules. Patients capable of benefitting from this method include those suffering from microbial infections such as viral infections and their related disorders such as Acquired Immune Deficiency in the case of human immunodeficiency virus (HIV); and cancers and their related disorders. Methods for isolating MRP4 and inducing anti-MRP4 antibodies and for determining and optimizing the ability of anti-MRP4 antibodies to assist in the examination of the target cells are all well-known in the art.

Methods for producing polyclonal anti-polypeptide antibodies are well-known in the art. See U.S. Pat. No. 4,493,795 to Nestor et al. A monoclonal antibody, typically containing Fab and/or F(ab')$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a MRP4-binding portion thereof, or MRP4, or an origin-specific DNA-binding, portion thereof.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present MRP4 and their ability to inhibit either specified MRP4 activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

Methods for producing monoclonal anti-MRP4 antibodies antibodies are also well-known in the art. See Niman et al., *Proc. Natl. Acad. Sci. USA,* 80:4949–4953 (1983).

Typically, the present MRP4 or a peptide analog is used either alone or conjugated to an immunogenic carrier, as the immunogen in the before described procedure for producing anti-MRP4 monoclonal antibodies. The hybridomas are screened for the ability to produce an anti-MRP4 antibody that immunoreacts with the a peptide analog of MRP4 and the present MRP4.

Furthermore, the present invention relates to a variety of diagnostic applications and methods for detecting a susceptibility to MDR, a predisposition to MDR, or the presence of MRP4, or disorders related thereto, in relation to levels of MRP4 present in a patient as compared to a standard or control. Anti-MRP4 antibodies as described above, have broad applications in these types of diagnostic applications and methods.

As described in detail above, antibody(ies) to MRP4 can be produced and isolated by standard methods including the well known hybridoma techniques. For convenience, the antibody(ies) to MRP4 will be referred to herein as $Ab_1$ and antibody(ies) raised in another species as $Ab_2$ (secondary antibody).

The presence of MRP4 in cells can be ascertained by the usual immunological procedures applicable to such determinations. A number of useful procedures are known. Three such procedures which are especially useful utilize either the MRP4 labeled with a detectable label, antibody $Ab_1$ labeled with a detectable label, or antibody $Ab_2$ labeled with a detectable label. The procedures may be summarized by the following equations wherein the asterisk indicates that the particle is labeled, and "MRP4" stands for MRP4:

A. MRP4*+Ab1=MRP4*$Ab_1$
B. MRP4+Ab*=MRP4$Ab_1$*
C. MRP4+$Ab_1$+$Ab_2$*=MRP4$Ab_1Ab_2$*

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody." or "DASP" procedure.

In each instance, the MRP4 forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims. $Ab_1$ will be referred to as a primary or anti-MRP-4 antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine. Texas Red, AMCA blue and Lucifer Yellow. A particular detecting material is anti-rabbit antibody prepared in goats and conjugated with fluorescein through an isothiocyanate.

MRP4 or its binding partner(s) can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging, molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752: and 4,016,043 are referred to by way of example for their disclosure of alternate labeling material and methods.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of MRP4 may be radiolabeled and combined, for example, with antibodies or other inhibitors thereto, after which binding studies would be carried out. Solutions would then be prepared that contain various quantities of labeled and unlabeled uncombined MRP4, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which the assay may be performed and utilized.

A PCR assay can be also utilized. For example, for detection of MRP4 nucleic acid, the following primers may be used: SEQ ID NO: 1 or portions thereof, SEQ ID NO: 5 and SEQ ID NO: 6). PCR is generally performed as described, using the thermostable enzyme Taq polymerase (1.5 u/sample) (AmpliTaq, Perkin Elmer Cetus) and a programmable PCR apparatus (MJ Research, Inc.). Target sequences are amplified as described herein and may be electrophoresed in a 6% 1×TBE polyacrylamide gel, at 1200V×2.5 h at room temperature, gels dried and signal detected by overnight autoradiography with or without an intensifying screen.

Commercial test kits suitable for use by a medical or laboratory specialist may be prepared to determine the presence or absence of MRP4 activity in a test sample or in a predetermined (control) sample, or the presence of MRP4 protein or subunits thereof in a test sample or in a predetermined (control sample), or the presence of MRP4 encoding nucleic acid in a test sample or in a predetermined (control sample), or the presence of nucleic acid capable of binding MRP4 encoding nucleic acid or subunits thereof in a test sample or in a predetermined (control) sample.

In accordance with the testing techniques discussed above, one class of such kits will contain at least labeled MRP4 or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Another class of such kits may also include PCR reagents, such as oligonucleotide primers, enzymes, gel matrixes, buffers, etc.

Accordingly, a test kit may be prepared for the diagnosis or detection of a susceptibility or predisposition to MDR related conditions including those resulting from infectious diseases and cancers.

Such a kit may be comprising: (a) a predetermined amount of at least one labeled immunochemically reactive component obtained by the direct or indirect attachment of present MRP4 factor or a specific binding partner thereto, to a detectable label; (b) other reagents; and (c) directions, including comparison levels of MRP4, for use of said kit.

An alternate kit for measuring the levels of MRP4 activity may comprise PCR reagents, such as oligonucleotide primers, enzymes, gel matrixes, buffers, directions, including comparison levels of MRP4, for use of said kit. A still further alternate can utilize reagents for measuring the levels of MRP4 activity as described: and directions, including comparison levels of MRP4, for use of said kit. More specifically, the diagnostic test kit may comprise: (a) a known amount of the MRP4 or fragment thereof as described above (or a binding partner) generally bound to a solid phase to form an immunosorbent, or in the alternative, bound to a suitable tag, or plural such end products, etc. (or their binding partners) one of each: (b) if necessary, other reagents: and (c) directions, including comparison levels of MRP4, for use of said kit.

In a further variation, the test kit may be prepared and used for the purposes stated above, which operates according to a predetermined protocol (e.g. "competitive," "sandwich," "double antibody," etc.), and comprises: (a) a labeled component which has been obtained by coupling the MRP4 to a detectable label; (b) one or more additional immunochemical reagents of which at least one reagent is a ligand or an immobilized ligand, which ligand is selected from the group consisting of: (i) a ligand capable of binding with the labeled component (a); (ii) a ligand capable of binding with a binding partner of the labeled component (a): (iii) a ligand capable of binding with at least one of the component(s) to be determined; and (iv) a ligand capable of binding with at least one of the bindings partners of at least one of the component(s) to be determined; and (c) directions for the performance of a protocol for the detection and/or determination of one or more components of an immunochemical reaction between the MRP4 and a specific binding partner thereto.

In accordance with the above, an assay system for screening potential drugs effective to modulate (i.e. increase or decrease) the levels of, or the activity of, the MRP4 may be prepared. The MRP4 may be introduced into a test system, and the prospective drug may also be introduced into the resulting cell culture, and the culture thereafter examined to observe any changes in the MRP4 activity of the cells, due either to the addition of the prospective drug alone, or due to the effect of added quantities of the known MRP4.

In addition to PCR based diagnostics, more traditional hybridization techniques may be used based on well known methods using MRP4-conserved sequences which show homology to MRP4 or sequences which specifically hybridize with MRP4. Nucleic acid analogs are also contemplated.

As used herein, a sequence is conserved if there is substantial homology of sequence between multiple gene species.

As used herein, the terms, "hybridization" and "binding" in the context of probes, primers and denatured DNA are used interchangeably. Probes which are hybridized or bound to denatured DNA are aggregated to complementary sequences in the polynucleotide. Whether or not a particular probe remains aggregated with the polynucleotide depends on the degree of complementarity, the length of the probe, and the stringency of the binding conditions. The higher the stringency, the higher must the degree of complementarity, and/or the longer the probe.

As used herein, the terms, "probe" and "primer" refer to an oligonucleotide designed to be sufficiently complementary to a sequence in a denatured nucleic acid to be probed, in relation to its length, to be bound under selected stringency conditions. The terms probes and primers may be used interchangeably. Probes may vary in length. Preferably such probes should be sufficiently long to hybridize to the modified RNAs in a specific and stable manner. A "semi-random probe" as the term is used herein, encompasses a class of probes wherein either a discrete portion of the probe is random, while another discrete portion is conserved as well as probes which have nucleotide preferences at particular positions within a sequence. For example, the discrete portion-type probe may have a predetermined adaptor sequence at its 5' end and a random sequence at its 3' end. Alternatively. several preferred probes have nucleotide preferences at specific positions within the probes while other positions are random. A "degenerate probe" as the term is used herein, encompasses a cocktail or mixture of probes wherein one or more of the possible triplet nucleotide sequences encoding an amino acid is incorporated into the probe sequence. For example, Serine may be encoded by six separate triple sequences (AGU, AGC, UCU, UCC, UCA, and UCG). Thus, a degenerate probe may reflect the degeneracy of the nucleotide triplet code. Alternatively, a randomized probe, as the term is used herein, encompasses a probe wherein the nucleotide at one or more positions may be randomized in order to yield a triplet sequence encoding an alternative or a random amino acid at the position.

An "end region" as the term is used herein, consists of the end nucleotide and a portion of the region including as much as that half of the entire sequence. For example, the "3' end region" or "3' region" of a probe may include the 3' half of the probe.

A preferred method of hybridization is blot hybridization. See Sambrook et al. 1989 *Molecular Cloning: A Laboratory Manual* 2nd Ed. for additional details regarding blot hybridization. Using this method, separated amplification products are transferred onto a solid matrix, such as a filter. The probe, which is detectable, either directly or indirectly, is hybridized to the solid matrix under appropriate conditions. The matrix is washed to remove excess probe. Thereafter the probe which specifically hybridized to the solid matrix can be detected.

The probe can be DNA or RNA and can be made detectable by any of the many labeling techniques readily available and known to the skilled artisan. Such methods include, but are not limited to, radio-labeling, digoxygenin-labeling, and biotin-labeling. A well-known method of labeling DNA is $^{32}$P using DNA polymerase, Klenow enzyme or polynucleotide kinase. In addition, there are known non-radioactive techniques for signal amplification including methods for attaching chemical moieties to pyrimidine and purine rings (Dale, R. N. K. et al. 1973 *Proc. Natl. Acad. Sci. USA* 70:2238–42), methods which allow detection by chemiluminescence (Barton, S. K. et al, 1992 *J. Am. Chem. Soc.* 114:8736–40) and methods utilizing biotinylated nucleic acid probes (Johnson. T. K. et al, 1983 *Anal. Biochem.* 133:125–131: Erickson. P. F. et al. 1982 *J. Immunol. Methods* 51:241–49; Matthaei. F. S. et al. 1986 *Anal. Biochem.* 157–123–28) and methods which allow detection by fluorescence using commercially available products. Non-radioactive labeling kits are also commercially available.

A basic description of nucleic acid amplification is described in Mullis, U.S. Pat. No. 4,683,202, which is incorporated herein by reference. The amplification reaction uses a template nucleic acid contained in a sample, two primer sequences and inducing agents. The extension product of one primer when hybridized to the second primer becomes a template for the production of a complementary extension product and vice versa, and the process is repeated as often as is necessary to produce a detectable amount of the sequence.

The inducing agent may be any compound or system which will function to accomplish the synthesis of primer extension products, including enzymes. Suitable enzymes for this purpose include, for example, *E. coli* DNA polymerase I, thermostable Taq DNA polymerase, Klenow fragment of *E coli* DNA polymerase I, T4 DNA polymerase, other available DNA polymerases, reverse transcriptase and other enzymes which will facilitate combination of the nucleotides in the proper manner to form amplification products. The oligonucleotide primers can be synthesized by automated instruments sold by a variety of manufacturers or can be commercially prepared based upon the nucleic acid sequence of this invention.

The degree of hybridization depends on the degree of complementarity, the length of the nucleic acid molecules being hybridized, and the stringency of the conditions in a reaction mixture. Stringency conditions are affected by a variety of factors including, but not limited to temperature, salt concentration, concentration of the nucleic acids, length of the nucleic acids, sequence of the nucleic acids and viscosity of the reaction mixture. More stringent conditions require greater complementarity between the nucleic acids in order to achieve effective hybridization.

Solid matrices, useful for hybridization or binding assays or in diagnostic kits are available to the skilled artisan. Solid phases useful to serve as a matrix for the present invention include but are not limited to polystyrene, polyethylene, polypropylene, polycarbonate, or any solid plastic material in the shape of test tubes, beads, microparticles, dip-sticks, plates or the like. Additionally matrices include, but are not limited to membranes, 96-well microtiter plates, test tubes and Eppendorf tubes. Solid phases also include glass beads, glass test tubes and any other appropriate shape made of glass. A functionalized solid phase such as plastic or glass which has been modified so that the surface carries carboxyl, amino, hydrazide, or aldehyde groups can also be used. In general such matrices comprise any surface wherein a ligand-binding agent can be attached or a surface which itself provides a ligand attachment site.

As used herein, "pharmaceutically acceptable" refers to molecular entities and compositions that are physiologically tolerable and do not typically produce an allergic or similar untoward reaction, such as gastric upset, dizziness and the like, when administered to a human. A pharmaceutically acceptable carrier encompasses any of the standard pharmaceutically accepted carriers, such as phosphate buffered saline solution, water emulsions such as an oil/water emulsion or a triglyceride emulsion, various types of wetting agents, tablets, coated tablets and capsules. Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients. The invention also provides for pharmaceutical compositions together with suitable diluents, preservatives, solubilizers, emulsifiers and adjuvants. Other embodiments of the compositions of the invention incorporate particulate forms, protective coatings, protease inhibitors or permeation enhancers for various routes of administration, including but not limited to intravenous, intramuscular, parenteral, pulmonary, nasal and oral.

As used herein, an "effective amount" is the amount required to achieve a clinically significant reduction in infection, preferably of at least 30 percent, more preferably of at least 50 percent, most preferably of at least 90 percent. Accordingly, the effective amount will vary with the subject being treated, as well as the condition to be treated. For the purposes of this invention, the methods of administration are to include, but are not limited to administration cutaneously, subcutaneously, intravenously, parenterally, orally, topically, or by aerosol.

The present invention further contemplates therapeutic compositions useful in practicing the therapeutic methods of this invention. A subject therapeutic composition includes, in admixture, a pharmaceutically acceptable excipient (carrier) and one or more of a polypeptide analog or fragment of the provided peptide or peptide composition, a peptidomimetic composition thereof as described herein as an active ingredient. A cocktail of the provided pharmaceutical composition in various combinations is also contemplated.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

As used herein, the term "synthetic amino acid" means an amino acid which is chemically synthesized and is not one of the 20 amino acids naturally occurring in nature. As used herein, the term "biosynthetic amino acid" means an amino acid found in nature other than the 20 amino acids commonly described and understood in the art as "natural amino acids."

As used herein, amino acid residues are preferred to be in the "L" isomeric form. However, residues in the "D" isomeric form can be substituted for any L-amino acid residue, as long as the desired functional property is retained by the polypeptide $NH_2$ refers to the free amino group present at the amino terminus of a polypeptide. COOH refers to the free carboxy group present at the carboxy terminus of a polypeptide. Abbreviations for amino acid residues are used in keeping with standard polypeptide nomenclature delineated in *J. Biol. Chem.*, 243:3552–59 (1969).

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

Amino acids with nonpolar R groups include: Alanine, Valine, Leucine, Isoleucine, Proline, Phenylalanine, Tryptophan and Methionine. Amino acids with uncharged polar R groups include: Glycine, Serine, Threonine, Cysteine, Tyrosine, Asparagine and Glutamine. Amino acids with charged polar R groups (negatively charged at Ph 6.0) include: Aspartic acid and Glutamic acid. Basic amino acids (positively charged at pH 6.0) include: Lysine, Arginine and Histidine (at pH 6.0). Amino acids with phenyl groups include: Phenylalanine, Tryptophan and Tyrosine. Particularly preferred substitutions are: Lys for Arg and vice versa such that a positive charge may be maintained; Glu for Asp and vice versa such that a negative charge may be maintained; Ser for Thr such that a free —OH can be maintained; and Gln for Asn such that a free $NH_2$ can be maintained. Amino acids can be in the "D" or "L" configuration. Use of peptidomimetics may involve the incorporation of a non-amino acid residue with non-amide linkages at a given position.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces -turns in the protein's structure.

As used herein, "pM" means picomolar, "nM" means nanmolar, "$\mu$M, means micromolar, "mM" means millimolar, "ul" or "$\mu l$" mean microliter, "ml" means milliliter, "l" means liter. As used herein, "$ED_{50}$", the effective dose 50, means the drug concentration yielding ½ maximal RT activity. "$IC_{50}$" means the inhibitory concentration at which growth is arrested by 50 percent.

The following examples are presented in order to more fully illustrate the preferred embodiments of the invention. They should in no way be construed, however, as limiting the broad scope of the invention. While the invention is described and illustrated herein by references to various specific material, procedures and examples, it is understood that the invention is not restricted to the particular material combinations of material, and procedures selected for that purpose. Numerous variations of such details can be implied as will be appreciated by those skilled in the art.

EXAMPLES

Example 1

Cell Variants Resistant to Anti-viral Nucleoside Analogs Contain an Efflux Pump

In this example, a T lymphocytic cell line was selected for PMEA resistance following exposure to cytotoxic concentrations of PMEA. The results show that the variant cells, termed CEM-r1, were limited in their ability to accumulate PMEA and its metabolites and exhibited enhanced cellular export of PMEAp. A modest alteration in phosphorylation of PLEA was also observed in the variant cells. Moreover, this resistant cell displays cross resistance to other related acyclic nucleoside phosphonate analogs including PMEG, AZT and 3TC. A second cell variant, resistant to PMEG, termed CEM-RPMEG, also displays cross-resistance to PMEA, AZT and 3TC. The results indicate that the multidrug resistance phenotypes are associated with an increased efflux of the active drug metabolite from the cells.

RESULTS

Selection of PMEA-resistant Cells

Selection for PMEA resistance was carried out by exposing CEM-SS cells in culture to increasing concentrations of PMEA, over several months. Of the various lines that grew in the presence of high concentrations of PMEA, one (designated CEM-r1) was selected and cultured for at least 10 generations in PMEA-free medium before subsequent studies. CEM-r1 cells, cultured in the presence or absence of PMEA, were morphologically indistinguishable from the parent CEM-SS cells. However, as shown in FIG. 1, CEM-r1 cells were ~250-fold more resistant to the cytotoxic effects of PMEA, compared with the parental cells. This drug resistance of CEM-r1 cells remained stable for at least 3 months of cell culturing in the absence of PMEA.

Uptake and Metabolism of [$^3$H]PMEA

Figure 2:
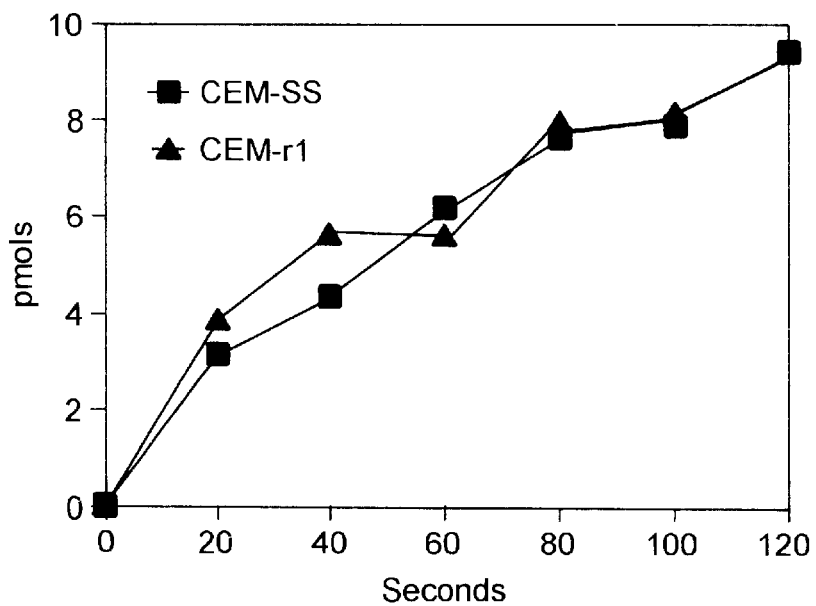
FIG. 2. Uptake and metabolism of [$^3$H]PMEA in CEM-SS and CEM-r1 cells. Exponentially growing cultures were incubated with 10 $\mu$M [$^3$H]PMEA, and at various intervals the cell extracts were analyzed for PMEA and its metabolites by ion exchange HPLC, as described herein. These results are from an experiment that was repeated twice, with identical results.
Figure 3A:
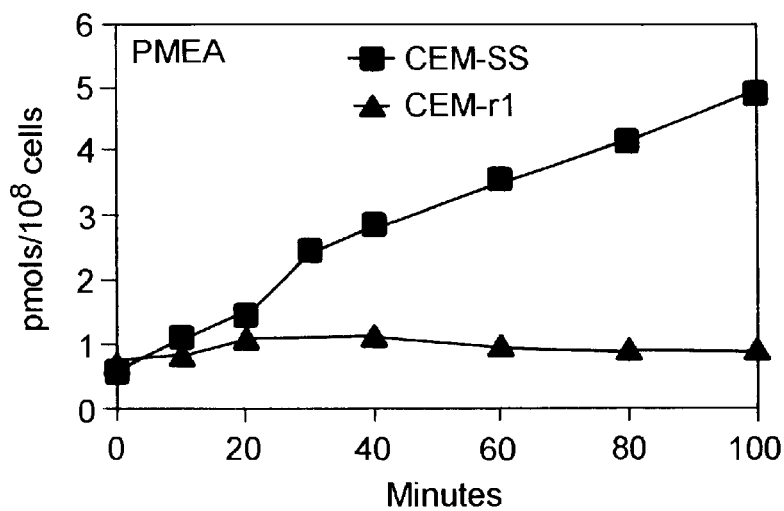
FIGS. 3A–3C. Uptake of [$^3$H]bispom-PMEA in CEM-SS and CEM-r1 cells. Exponentially growing cultures were incubated with 1 μM [³H]bispomPMEA, and at the indicated times incubations were terminated by centrifugation of cells through an inert oil phase. The amounts of bispomPMEA internalized at various intervals of incubation are shown. The data are from a typical experiment, which has been repeated several times with identical results.
Figure 3B:
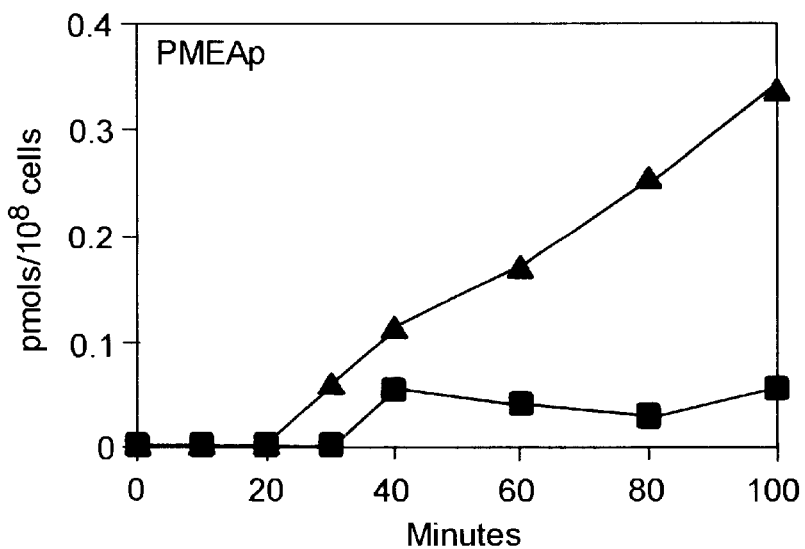
Figure 3C:
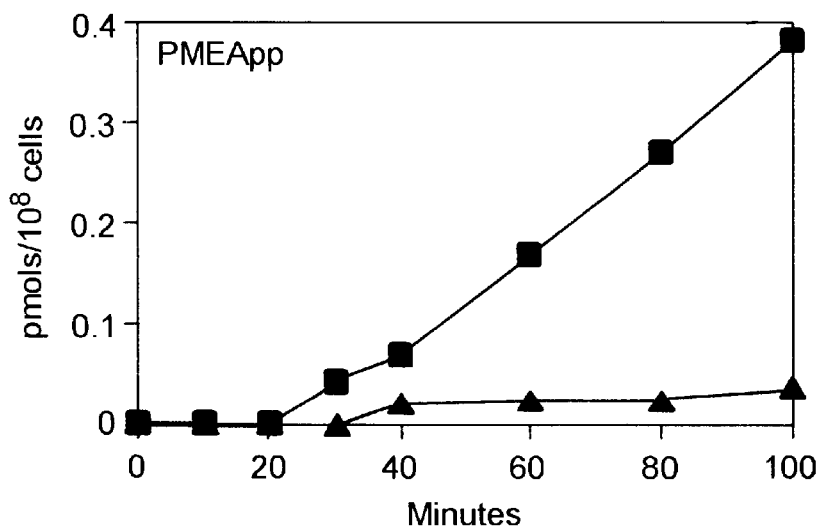

Because PMEA requires activation to the diphosphorylated derivative PMEApp for its activity, it was determined whether the mutant cells exhibit altered drug anabolism. The mutant and parental cells were incubated with 10 $\mu$M [$^3$H]PMEA and at various times were analyzed for intracellular levels of PMEA and its metabolites by Partisil SAX HPLC. In the parental cells the accumulation of PMEA and its anabolites PMEAp and PMEApp was dependent on the concentration of PMEA in the external medium at least up to 2 mM, with no evidence of saturation in either the uptake or phosphorylation of the drug. The parental CEM-SS cells accumulated PMEA and its anabolites PMEAp and PME-App in a relatively linear fashion for at least 100 min, during which measurements were made. In contrast, CEM-r1 cells accumulated markedly lower levels of PMEA than did the parental cells and there were virtually no anabolites, PMEAp and PMEApp, detectable within this time period (FIG. 2). The metabolism of [$^3$H]PMEA was also examined in both cell lines after longer periods (i.e., 8 and 12 hr) of incubation with 10 $\mu$M [$^3$H]PMEA. As shown in Table 1 below, in wild-type cells intracellular PMEA levels measured after 8 and 12 hr reached 1.7 and 2.5 $\mu$M, respectively, and PMEAp and PMEApp concentrations increased to 0.23 and 0.41 $\mu$M, respectively, after a 12-hr incubation period. In contrast, PMEA levels in CEM-r1 cells after 12 hr reached only 1 $\mu$M (40% of the wildtype level) and PMEAp and PMEApp levels were only 2–3% of parental cell levels after 12 hr.

TABLE 1

Intracellular Accumulation Of PMEA, PMEAp And PMEApp In CEM-SS And CEM-R1 Cells

| | Intracellular levels | | | |
|---|---|---|---|---|
| | CEM-SS | | CEM-r1 | |
| | 8 hr | 12 hr | 8 hr | 12 hr |
| | $\mu$M | | | |
| PMEA | 1.7 | 2.5 | 1.0 (56%) | 0.99 (40%) |
| PMEAp | 0.13 | 0.23 | 0.005 (3.8%) | 0.005 (2.2%) |
| PMEApp | 0.22 | 0.41 | 0.008 (3.6%) | 0.01 (2.4%) |

Exponentially growing cultures were incubated with 10 $\mu$M [$^3$H] PMEA for 8 or 12 hr and the cell extracts were analyzed for PMEA and its metabolites by ion exchange HPLC, as described.

Uptake and Metabolism of [$^3$H]bispom-PMEA

Lower levels of PMEA and anabolites in CEM-r1 cells could result from decreased uptake, increased excretion, and/or decreased activation of the drug. However, the level of radioactive PMEA accumulating in CEM-r1 cells was too low for a detailed analysis of the specific mechanism involved. Therefore, the metabolism of [$^3$H]bispom-PMEA (15), a lipophilic prodrug of PMEA, was analyzed in the two cell lines in order to further examine the mechanism of resistance in the mutant cell line. It was previously shown that bispom-PMEA, unlike PMEA, is rapidly taken into cells and converted by cellular esterases to unmodified PMEA (24). FIG. 2 shows data on the early time course (120 sec) of 1 $\mu$M [$^3$H]bispom-PMEA entry into the parental and CEMr1 cells. There was no significant difference between the two cell lines in their initial uptake of bispom-PMEA. However, when the cells were incubated for longer periods with [$^3$H]bispom-PMEA, significant differences in the accumulation of drug metabolites were observed. Table 2 depicts results from an experiment in which the two cell lines were incubated with 1 $\mu$M [$^3$H]bispom-PMEA for 15 min. As shown previously (24), the extent of accumulation of PMEA and its metabolites PMEAp and PMEApp in the parental CEM-SS cells was much higher after a 15-min incubation with 1 $\mu$M bispom-PMEA than after an 8-hr incubation with 10 $\mu$M PMEA (compare Tables 1 and 2). In the resistant CEM-r1 cells, however, incubation with 1 $\mu$M [$^3$H]bispom-PMEA resulted in levels of tritiated PMEA, PMEAp, and PMEApp that were only about one third of those seen in parental cells. Only ~2% of the radioactivity present in the cells after incubation could be detected as the intact pro-drug and this was similar in parental and resistant cells, indicating that there was no significant difference in the hydrolysis of the pro-drug to the unmodified parental drug in the two cell lines.

TABLE 2

Metabolism Of [$^3$H]Bispom-PMEA In CEM-SS And CEM-r1 Cells

| Metabolite | Metabolite Levels | | | |
|---|---|---|---|---|
| | Cells | | Medium | |
| | CEM-SS | CEM-r1 | CEM-SS | CEM-r1 |
| | $\mu$M | | nM | |
| PMEA | 33.1 | 13.3 | 4.8 | 23.2 |
| PMEAp | 0.48 | 0.17 | NDa | ND |
| PMEApp | 0.16 | 0.07 | ND | ND |
| Bispom-PMEA | 0.03 | 0.04 | 490 | 429 |
| Monopom-PMEA | 4.6 | 4.1 | 185 | 166 |

NDa, not determined

Exponentially growing cultures were incubated with 1 $\mu$M [$^3$H]bispom-PMEA for 15 minutes and the various metabolites in the cell extracts and media were analyzed by ion exchange HPLC, as described. Data are shown for one individual experiment; essentially similar results were obtained in a second independent experiment.

The results in Table 2 also include the levels of various metabolites in the medium of cells incubated with tritiated [$^3$H]bispom-PMEA. Most of the radioactivity remaining in the medium was associated with bispom-PMEA and monopomPMEA, and this was comparable for the two cell lines. However, a significant difference was seen in the levels of extracellular PMEA, which were ~5-fold higher with the mutant CME-r1 cells than with the parental CEM-SS cells. Control experiments revealed that under these conditions direct extracellular hydrolysis of bispom-PMEA in the medium did not contribute significantly to PMEA in the medium. Thus, this observation suggested that the appearance of PMEA in the medium was due to the excretion from cells of the drug derived from intracellular metabolism of bispom-PMEA.

Measurements of Efflux of [$^3$H]PMEA

Figure 4A:
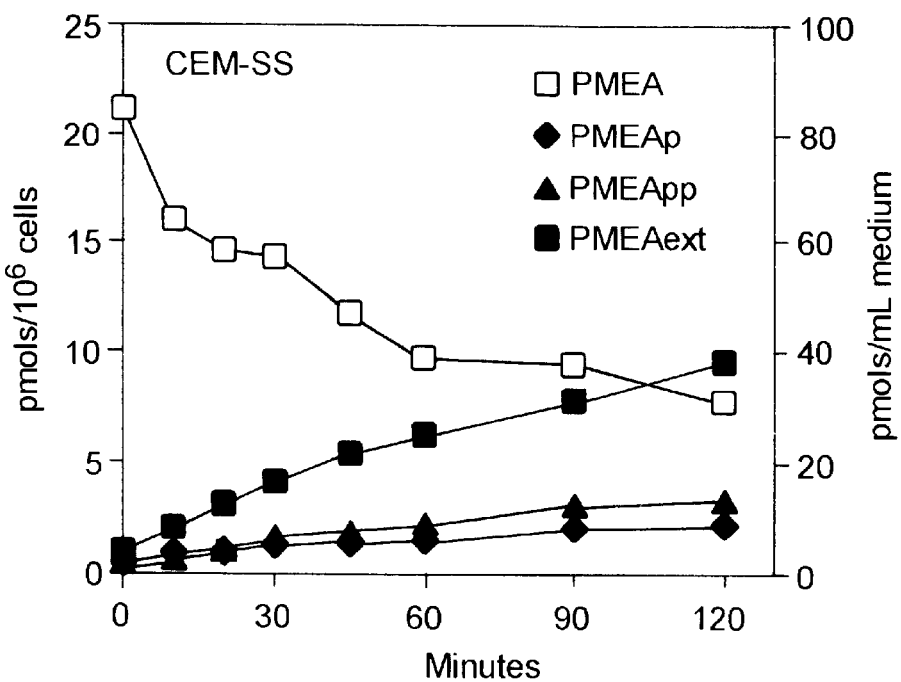
FIGS. 4A–4B. Efflux of PMEA from [³H]bispom-PMEA-treated cultures. Exponentially growing cultures of CEM-SS and CEM-r1 cells were incubated for 15 minutes with 1 μM or 2 μM [³H]bispom-PMEA, respectively. The cell extracts and media were analyzed by ion exchange HPLC as described herein.
Figure 4B:
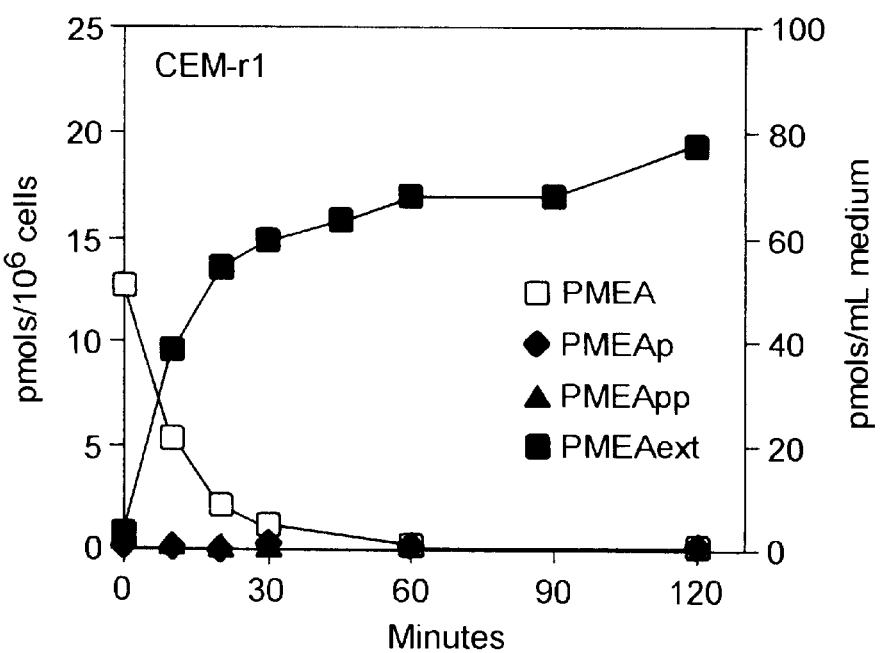

To examine whether the resistant cells could be altered in their capacity to retain the phosphonate analog, the clearance of [$^3$H]PMEA and its metabolites from CEM-SS and CME-r1 cells was determined. CEM-SS or CME-r1 cells were incubated for 15 minutes with 1 $\mu$M or 2 $\mu$M [$^3$H]bispom-PMEA, respectively, in an attempt to accumulate comparable levels of intracellular PMEA and anabolites, and were then incubated in drug-free medium. Aliquots of cells and medium sampled at different intervals over a period of 2 hr were analyzed by HPLC, and the results are shown in FIG. 4. The intracellular levels of radioactivity associated with PMEA declined gradually in the parental cells, and half-maximal clearance was attained within about 60 min. Some of this clearance was probably due to the anabolism of PMEA, because the PMEAp- and PMEApp-associated radioactivity continued to accumulate within the cells, but the majority of the radioactivity was excreted into the medium as PMEA. In contrast to the results with parental cells, loss of intracellular PMEA-associated radioactivity in the resistant CEM-r1 cells was extremely rapid and the majority of the radioactivity within the cells was excreted into the medium within 20–30 minutes of incubation (FIG. 4). From the increases in the extracellular radioactivity accumulated in the medium, one can calculate that the rate of efflux of PMEA was increased ~7-fold to 2.55 pmol/min/$10^6$ in resistant CEM-r1 cells, from 0.4 pmol/min/$10^6$ cells in parental CEM-SS cells.

Cross-resistance to Other Agents

The relative sensitivity of the wild-type and CEM-r1 cells to structurally related and unrelated analogs was also been examined. As shown in Table 3. the CEM-r1 cells are highly cross-resistant to the prodrug bispom-PMEA and the 2,6-diaminopurine derivative PMEDAP. Only partial cross-resistance was observed against two related nucleoside phosphonates. HPMPA and PMEG (Table 3). Interestingly, the mutant was also partially resistant to a number of unrelated purine nucleosides, including adenosine, 2-chlorodeoxyadenosine, and 2-fluoroarabinosyladenine, but not to arabinosyladenine, 2'-deoxyadenosine, hydroxyurea, or the adenine nucleotide precursor 5-amino4-imidazolecarboxamide riboside. CEM-r1 cells were also not resistant to vinblastine and colchicine, two agents that are characteristic of the MDR phenotype in a number of mutant cell lines selected against these agents (25). It should be noted that the MDR mutant CEM/VLB$_{100}$ (26) did not exhibit any cross-resistance to PMEA.

TABLE 3

Comparative Resistance Of CEM And CEM-R1 Cells To Various Agents

| | IC$_{50}$ | | |
|---|---|---|---|
| Compound | CEM-SS | CEM-r1 | Relative Resistance |
| | $\mu$M | | |
| PMEA | 34 | 6200 | 182 |
| PMEADAP | 2.3 | 1200 | 533 |
| Bispom-PMEA | 0.26 | 32 | 123 |
| PMEG | 0.7 | 19 | 30 |
| HPMPA | 92 | 1100 | 12 |
| Adenosine | 38 | 205 | 5.4 |
| 2-Chlorodeoxyadenosine | 0.08 | 0.4 | 5.5 |
| 2-Fluoroarabinosyladenine | 1.2 | 4.4 | 3.7 |
| Arabinosyladenine | 0.7 | 0.9 | ~1 |
| 2'-Deoxyadenosine | 1.7 | 2.5 | ~1 |
| 5-Amino-4-imidazolecarboxamide | 130 | 106 | ~1 |
| Hydroxyurea | 55 | 50 | ~1 |
| Vinblastine | 0.0018 | 0.0021 | ~1 |
| Colchicine | 0.014 | 0.013 | ~1 |

The IC$_{50}$ values were obtained after 2 days of culture. Each result is the mean of one representative experiment performed in duplicate. The cultures with the purine nucleosides adenosine, 2'-deoxyadenosine, and arabinosyladenine contained 5 μM deoxycoformycin to inhibit adenosine deaminase activity.

Enzyme Levels

Cytosolic extracts of CEM-SS and CEM-r1 cells were also examined for differences in enzyme activity of potential importance for nucleoside/nucleotide analog metabolism. The two cell lines had indistinguishable activities of adenosine kinase and deoxycytidine/deoxyadenosine kinase, enzymes that phosphorylate the various purine nucleosides described above to their 5'-phosphorylated derivatives (27–30), and PRPP synthetase, which has been implicated in the phosphorylation of PMEA (11) (Table 4). However, the resistant CEM-r1 cells did exhibit a 2-fold decrease in the activity of adenylate kinase, compared with the wild-type CEM-SS cells (Table 4), suggesting that this enzyme may be important for the phosphorylation of PMEA.

TABLE 4

Purine Nucleoside-Phosphorylating Enzymes In CEM-SS And CEM-R1 Cells.

| | Activity | |
|---|---|---|
| | CEM-SS | CEM-r1 |
| Enzyme | nmol/hr/mg of protein | |
| Adenosine kinase | 143 | 168 |
| Deoxycytidine/deoxyadenosine kinase | 4.5 | 4.9 |
| PRPP synthetase | 492 | 480 |
| Adenylate kinase | 2675 | 1442 |

Mean values from at least two independent determinations are shown. The different enzyme activities, adenosine kinase (24), deoxycytidine kinase (24), PRPP synthetase (11), and adenylate kinase (25), were determined according to previously described procedures.

Antiviral Activity and Cytotoxicity of AZT, 3TC, PMEA and PMEG in CEM-SS and CEM-r1 Cells The PMEA-resistant cell line, CEM-r1, used in the present study was maintained in a drug-free medium for several months before studying the effects of PMEA, PMEG, AZT and 3TC. Table 5 summarizes the ED$_{50}$ and the IC$_{50}$ values, which indicate the antiviral activity and the cytotoxicity, respectively, in both the wild type and mutant cells.

Phosphorylation of AZT

Both CEM-SS and CEM-r1 cells were incubated with 10 μM AZT and the phosphorylated biotransformation products of AZT present intracellularly or in the media were separated by solid phase extraction (19) and quantitated by liquid scintillation counting. The results, shown in Table 6, demonstrate a 4- to 5-fold decrease in the intracellular levels of AZTMP, AZTDP and AZTTP in the CEM-r1 cells compared with CEM-SS cells at the time periods evaluated. The appearance of the phosphorylated metabolites into the medium was also determined in both the cell lines. AZTDP and AZTTP were not detected in the medium of either CEM-SS or CEM-r1 cells. However, the amount of AZTMP accumulated in the media was approximately 3-fold higher in CEM-r1 cells than in CEM-SS cells. The cellular integrity of both CEM-SS and CME-r1 cells was verified by Trypan Blue exclusion assay (22) throughout the time course of the experiments and was found to be greater than 98%.

TABLE 5

Antiviral Activity & Cytotoxicity of Analogs

| | Antiviral Activity ED$_{50}$ (μM) | | Fold | Cytotoxicity IC$_{50}$ (μM) | | Fold |
|---|---|---|---|---|---|---|
| DRUG | WT | CEM-r1 | Resistance | WT | CEM-r1 | Resistance |
| PMEA | 2 | >300 | >150 | 80 | 20000 | 250 |
| PMEG | —* | —* | — | 5 | 200 | 40 |
| AZT | 0.006 | 0.140 | 23 | 500 | 3000 | 6 |
| 3TC | 0.21 | 1.10 | 5.5 | 1000 | 5000 | 5 |

(—*PMEG did not have any antiviral activity against HIV)

The fold resistance for each drug was calculated as the ratio of the IC$_{50}$ of the resistant cell line to the IC$_{50}$ of the wild type cells for that drug.

Cellular Transport-Intracellular Accumulation of AZT

Figure 5:
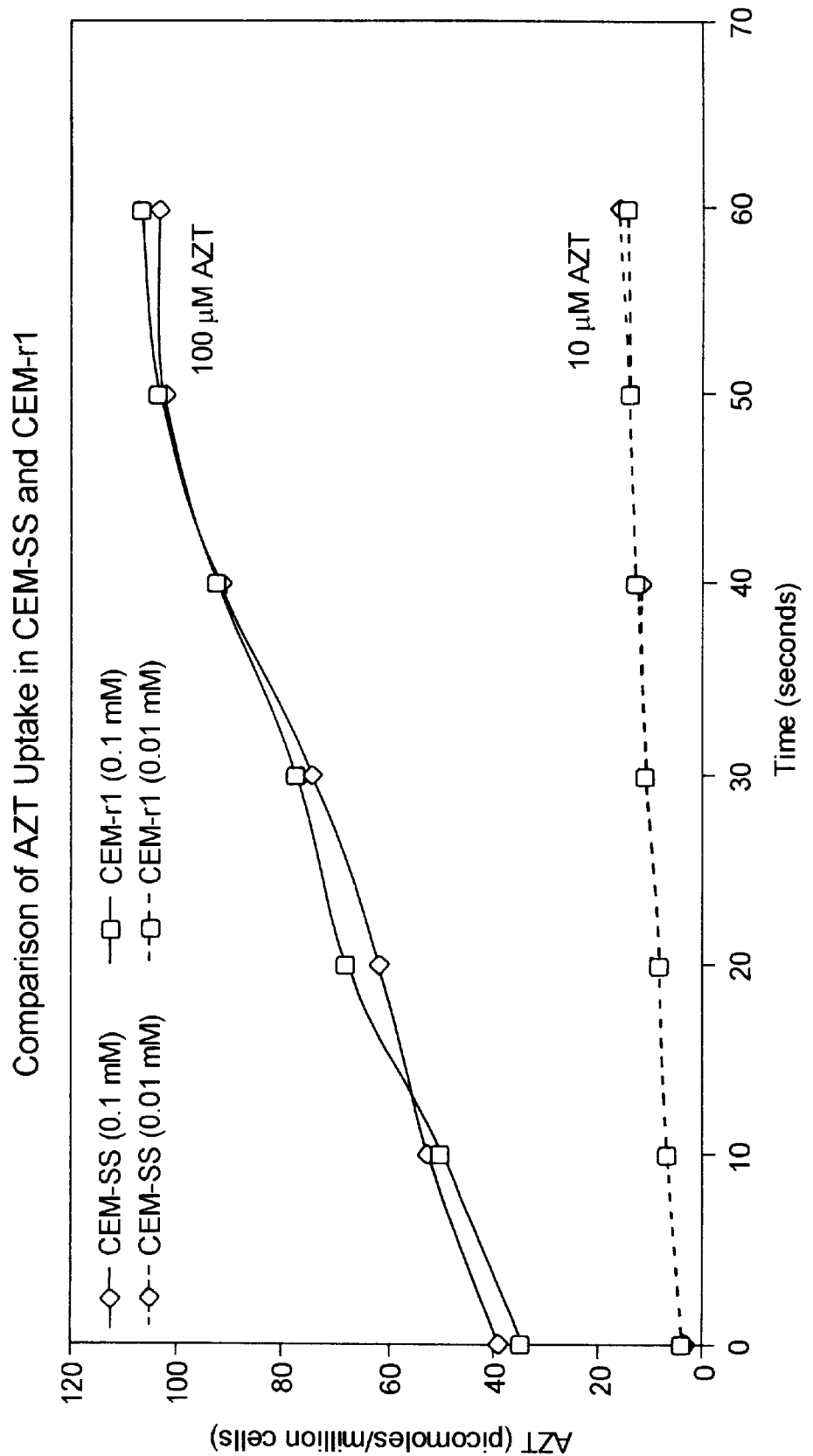
FIG. 5. Uptake of AZT in CEM-SS and CEM-r1 cells, cells were incubated with 10 μM or 100 μM [³H]AZT for time periods ranging from 10–60 seconds Transport was terminated by the addition of cold PBS containing a transport inhibitor and centrifuging the cells through oil in a microfuge. The radioactivity was determined in a liquid scintillation counting.

Using [$^3$H] AZT, the transport of AZT across the cellular membrane was studied in each cell line. Cellular uptake of AZT (10 μM and 100 μM) was measured up to 120 seconds and was similar in both the cell lines. The results displayed in FIG. 5 indicate that both the CEM-SS and CEM-r1 do not exhibit any deficiency in the uptake of the drug.

Cellular Transport: Efflux of AZT

Figure 6A:
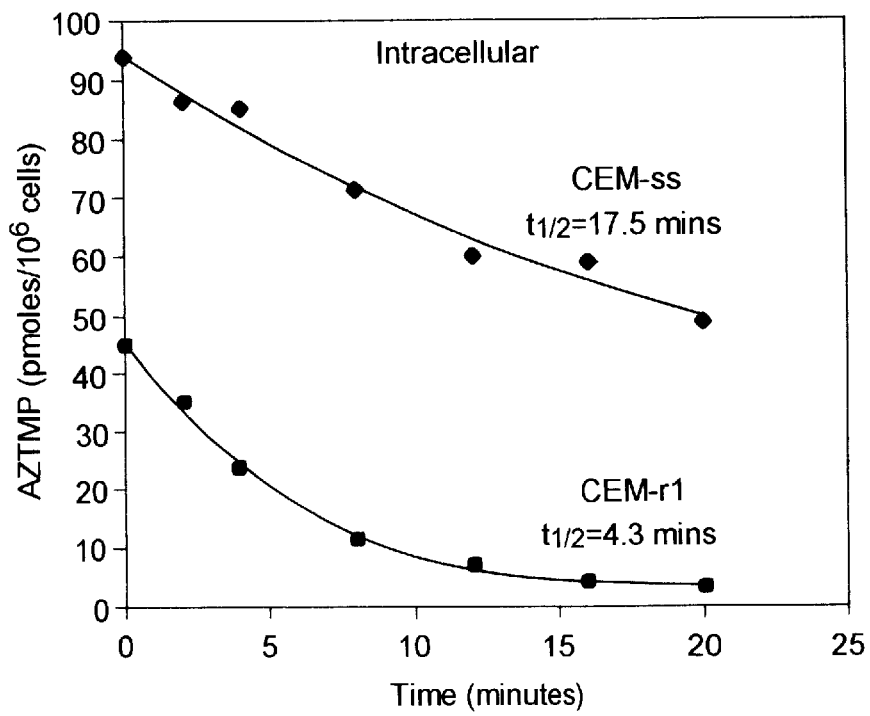
FIGS. 6A–6B. AZTMP efflux. Cells were loaded with 10 μM of [³H]AZT for 1 h at 27° C. Radioactivity was determined immediately after removal of radioactive medium and washing the cells with ice-cold PBS. At various time periods ranging from 2 to 20 minutes samples of the cells were taken and the level of radioactivity remaining in the cells as AZTMP and that excreted into the medium determined after separation of the metabolites by HPLC. Experiments were performed twice and the figure represents a single experiment.
Figure 6B:
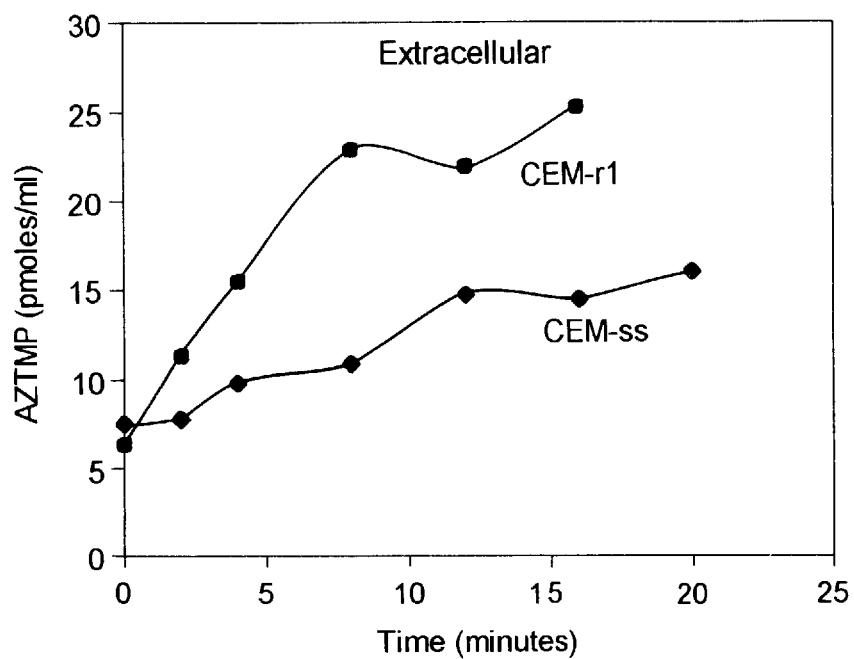

Cells were incubated for 60 minutes with [$^3$H]-AZT (10 μM) after which they were washed free of radioactivity, resuspended in drug-free medium and the intracellular and the extracellular concentration of [$^3$H]-AZT were measured. The results, displayed in FIG. 6. show that following the removal of extracellular AZT the intracellular concentration of AZTMP decreased linearly over 16 minutes. At least 80% of the AZTMP present intracellularly in CEM-r1 cells was excreted into the medium in 10 minutes (FIG. 6A). The time ($t_{1/2}$) required to attain half the intracellular concentration of AZTMP compared to the intracellular concentration at the time of resuspension of cells in the drug-free medium was significantly different (CEM-SS: $t_{1/2}$=17.5 min.; CEM-r1:$t_{1/2}$=4.5 min.). However, there was less difference in the $t_{1/2}$ for intracellular AZT in the wild type and mutant cell lines (CEM-SS: $t_{1/2}$=8.1 min.; CEM-r1: $t_{1/2}$=6.5 min.). The intracellular levels of AZTDP and AZTTP, which represented 1% of total cellular anabolites, were also measured and did not change significantly in either of the two cell lines over the time period studied.

Effect of Concentration of Bis(POM)PMEA on the Efflux of PMEA

Figure 7A:
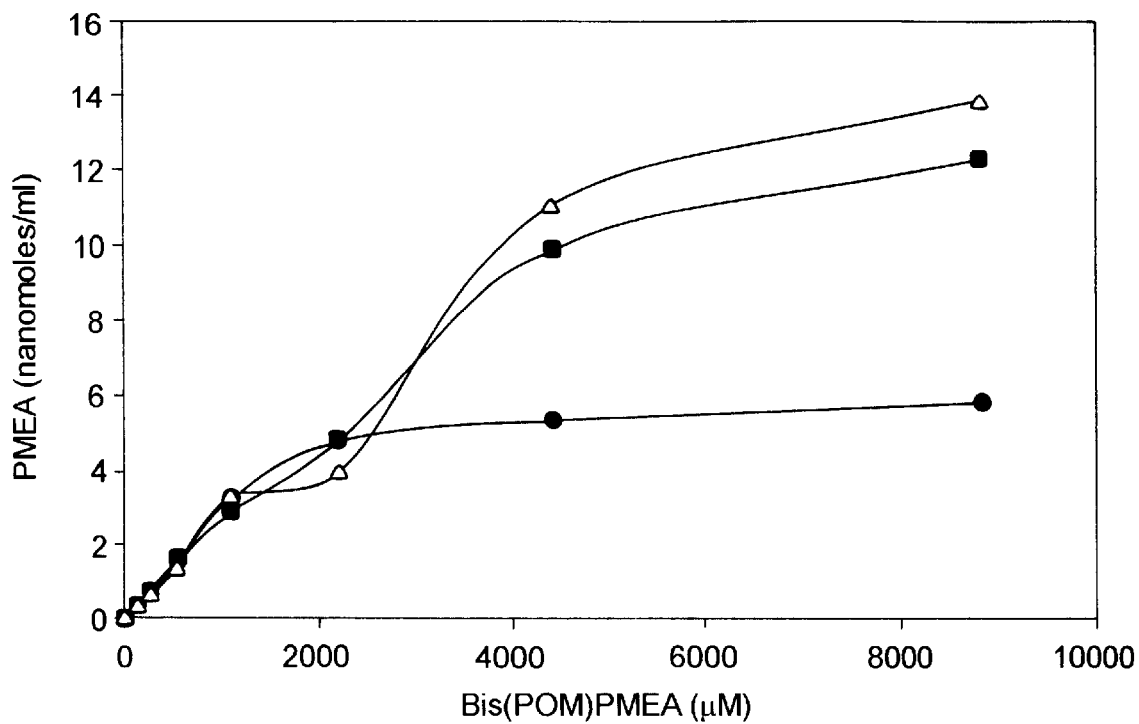
FIGS. 7A–7B. Effect of bis(POM)PMEA concentration on PMEA efflux. Both CEM-SS and CEM-r1 cells were incubated with increasing concentrations of the prodrug bis(POM)PMEA (range from 9.97 mM to 8.8 mM). After incubation, cells were pelleted and resuspended in drug-free medium and the amount of PMEA effluxing into the medium determined. Data are the mean from two separate experiments.
Figure 7B:
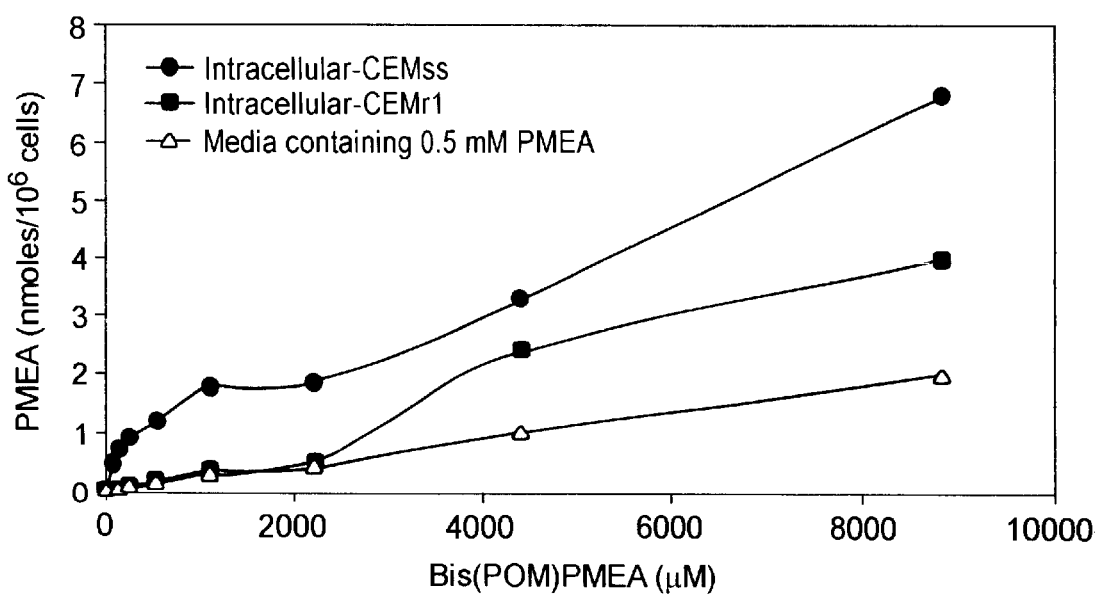

Both CEM-SS and CME-r1 cells were incubated for 3 minutes with increasing concentrations (range 0.07 mM to 8.80 mM) of the prodrug for the selecting agent, Bis(POM) PMEA. After incubation, the cells were pelleted and reconstituted in drug-free medium, and the amount of PMEA present in the medium and intracellularly was measured 15 minutes after resuspension. The amount of PMEA effluxing out into the medium at 15 minutes increased initially with increasing concentration (FIG. 7A). At concentrations higher than 2.2 mM and 4.4 mM Bis(POM)PMEA, respectively, in CEM-SS and CEM-r1 cells, the amount of PMEA effluxed out did not increase significantly indicating saturation of the protein-mediated efflux process at increasing concentrations of the drug. However, the amount of PMEA present intracellularly increased with increasing concentrations of the prodrug (see FIG. 7B).

Effect of PMEA Concentration Gradient on PMEA Efflux

CEM-r1 cells were incubated with 0.07–8.8 mM Bis (POM)PMEA for 3 minutes. The cells were pelleted and reconstituted in either drug-free medium or in medium containing 0.5 mM PMEA, and the amount of PMEA present in the medium and intracellularly was measured 15 minutes after resuspension. The results, displayed in FIG. 7A, show no significant difference in the amount of PMEA effluxed out in the presence or absence of PMEA in the medium, providing evidence for efflux of PMEA against a concentration gradient which is consistent with a protein-mediated efflux of the compound.

Inhibitors of Drug Efflux

To assess if the observed transport of AZTMP in CEM-r1 cells was energy-mediated efflux, ATP was depleted from both of the cell lines by the addition of sodium azide. Both CEM-SS and CEM-r1 cells were incubated in medium that contained 10 mM sodium azide and 10 mM 2-deoxy-D-glucose, and within 5 minutes the intracellular ATP levels (23) decreased by 90% but the viability of the cells was not altered.

Accordingly, in this example, the human T lymphoid cell line CEM-r1 was further examined as to its demonstration of efflux of acyclic nucleoside analogs such as PMEA and AZT. This cell line also displays cross resistance to other related acyclic nucleoside phosphonate analogs such as PMEG 9-(2-phosphonylmethoxyethyl)guanine) as well as the anti-retroviral nucleoside analog AZT). Transport studies were conducted as set forth in Table 6 below, and indicated that the CEM-r1 cells rapidly effluxed PMEA and AZTMP (azido-thymidine monophosphate) but not their di- and triphosphate derivatives (not shown). Also, depletion of intracellular ATP by azide and 2-deoxyglucose caused a marked decrease in the rate of efflux of both PMEA and AZTMP in CEM-r1, but not from CEMss sensitive cells.

The P-glycoprotein (Pgp) antagonist, verapamil had no effect on the rate of efflux, however, a non-traditional Pgp antagonist dipyridamole[63] significantly decreased the rate of PMEA and AZTMP efflux (not shown). These studies suggested PMEA and AZTMP efflux occurred by an ABC cassette transporter that was unlikely to be P-glycoprotein because; i) verapamil had no effect on drug efflux and ii) Pgp was undetectable in CEMss or CME-r1 cells by Western blot analysis (not shown). Thus, it was hypothesized that another ABC cassette transporter was involved in PMEA and AZTMP efflux.

TABLE 6

Functional Characterization of CEMss and CEMr-1

| | EFFLUX KINETICS | | | |
|---|---|---|---|---|
| | AZTMP (min) | | PMEA (min) | |
| Treatment | CEMss | CEMr-1 | CEMss | CEMr-1 |
| None | 17.5 | 4.3 | >26 | 4.4 |
| Azide + Deoxyglucose | 16.3 | 18.1 | >26 | >26 |

| DRUG SENSITIVITY ($\mu$M) | | | |
|---|---|---|---|
| PMEA | | AZT | |
| CEMss | CEMr-1 | CEMss | CEMr-1 |
| 80 | 2000 | 500 | 3000 |

Referring to Table 6 in greater detail, efflux kinetics were studied. Transport analysis of PMEA was conducted as previously described[48]. Both the CEM-SS and CEM-r1 cells were pre-labeled with [$^3$H]-AZT by incubation in its presence for 60 minutes. The cells were then washed free of radioactivity and then incubated in drug-free medium in the presence of sodium azide and 2-deoxy-D-glucose. At various time periods, the amount of intracellular AZTMP was measured. As reported in Table 6, depletion of ATP led to an inhibition of AZTMP efflux (i.e. a significant accumulation of AZTMP in the CEM-r1 cells but not in the CEM-SS cells). The $t_{1/2}$, for AZTMP in energy-deprived CEM-r1 cells ($t_{1/2}$=4 minutes) was almost totally restored to that observed in CEM-SS cells ($t_{1/2}$=17.1 min). Further, depletion of cellular energy had very little effect on AZTMP efflux in CEM-SS cells ($t_{1/2}$=16.3 minutes in the presence of sodium azide and 2-deoxy-D-glucose). These findings suggest the presence of an active efflux system for AZTMP in the CEM-r1 cells that does not appear to be expressed in the wild type cells, CEM-SS.

Drug Sensitivity

The cells were treated with varying concentrations of PMEA and AZT and the concentration to inhibit 50% growth after a 24 h exposure was determined as previously described[48].

RESULTS

Figure 26:
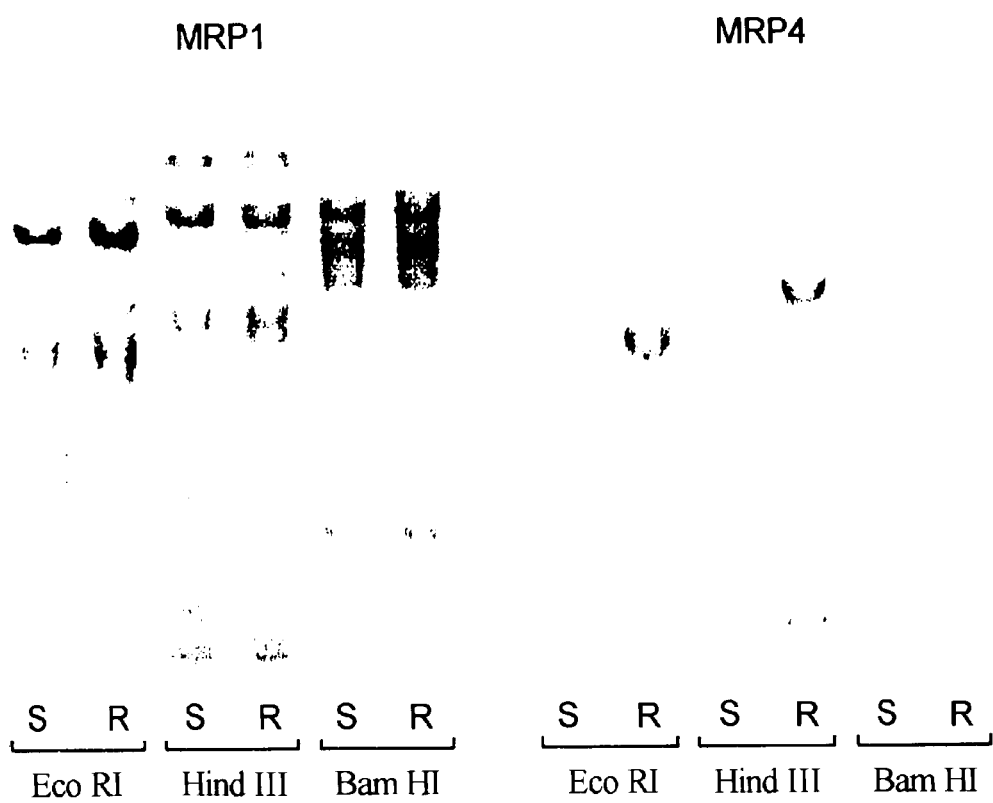
FIG. 26A. Southern Blot analysis demonstrates specific amplification of MRP4. (A) Genomic DNA (10 ug) isolated from CEMss (S) and CEM-r1 cells (R) was digested with the indicated restriction enzymes followed by Southern blotting and sequential hybridization with $^{32}$P-labeled cDNA probes MRP1, MRP2/cMOAT MRP3, and MRP4. Hybridized bands were visualized autoradiographically and quantified by densitometry.
FIG. 26B. Cytogenetic evidence for MRP4 amplification in CEM-r1 cells. The MRP4 cDNA was used to screen a human leukocyte genomic library (Clontech). One MRP4 genomic clone containing intron sequence and exonic sequences homologous to the MRP4 cDNA was purified, sequenced, and used for fluorescent in situ hybridization analysis. In normal lymphocytes (CEMss) MRP4 specifically hybridized to human chromosome 13q32. To confirm chromosomal localization a probe (Oncor) that recognizes the centromere from chromosome 21 and 13 was used. Of 50 independent CEM-r1 cells examined, 46 had the MRP4 homogeneous staining region with the same number of copies of MRP4 gene, and they were all observed at the distal arm of chromosome 13q.

The large magnitude and phenotypic stability of drug resistance for months in the absence of drug[48] of CEM-r1 cells suggested gene amplification might contribute to CEM-r1 drug resistance. Because of the recent expansion in the number of MRP related genes[49, 61], genomic DNA from the CEMss and CEM-r1 cells was isolated, and was screened by Southern blot for changes in gene copy of genes encoding MRP1-4. The MRP1 gene was not amplified in the CME-r1 cells (FIG. 8), nor was MRP2 or MRP3 (not shown) as their signal intensity was not different between CEMss and CEM-r1 cells. In contrast, compared with CEMss, the CEM-r1 cell line had increased MRP4 gene copy, a finding consistent with gene amplification[62], Densitometry revealed that the MRP4 gene was amplified from 8–10 fold. In addition, a longer exposure of the CEMss revealed that the MRP4 gene structure was no different in the CEM-r1 cells. To verify that the MRP4 gene was amplified, a MRP4 genomic clone was isolated and FISH analysis performed on metaphase chromosomes (FIG. 26B). In CEMss cells MRP4 hybridized to chromosome 13 at position 13q32 (not shown) a more refined localization than previously reported[49]. In the CEM-r1 cells a large homogeneous staining region (HSR) was observed only on the distal arm of chromosome 13 (FIG. 26B). This finding demonstrates that the increased MRP4 gene copy detected by Southern blot is due to gene amplification and not changes in CEM-r1 ploidy.

Figures 27A, 27B:
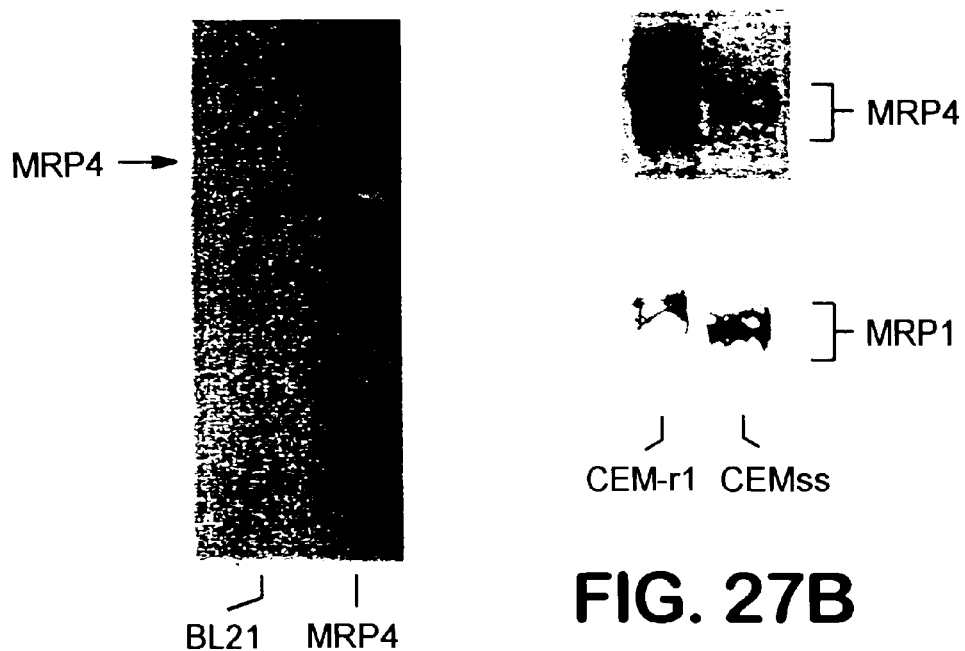
FIG. 27. MRP4 overexpression in CEM-r1 cells. (A) Lysates from BL21 bacteria or BL21 transformed with MRP4 in frame (MRP4) were analyzed on immunoblots. The fusion protein was localized with strepavidin alkaline phosphatase detection (not shown) or with affinity purified peptide antiserum against human MRP4. (B) CEMss and CEM-r1 cells were lysed in buffer containing a protease inhibitor cocktail (Boehinger Mannheim) and analyzed on immunoblots with either MRP4 or MRP1 antiserum (monoclonal PRL1 (Oncogene Science) reacted with peroxidase-conjugated antibodies and detected by enhanced chemiluminescence (Amersham).

The compelling association between MRP4 amplification and the increased rate of drug efflux is further substantiated by evidence that the MRP4 protein is overexpressed. Antiserum specific for MRP4 was developed and specificity was demonstrated by immunoblot detection of an in-frame MRP4 bacterial fusion (FIG. 27A), but not the out of frame MRP4 (not shown), and the absence of MRP4 antiserum immunoreactivity with either Pgp/MDR1, MRP1, or MRP2 in lysates from cells expressing these proteins (not shown). Immunoblot analysis with anti-MRP4 antiserum revealed a dramatic overexpression of MRP4 in the CME-r1 cells. The increase in MRP4 expression was specific because stripping and re-probing the blot demonstrated no change in the expression of MRP1 (FIG. 27B). Fractionation of the CEM-r1 lysate revealed that the majority of MRP4 was found in the membrane fraction (not shown).

To test the functional relationship between MRP4 gene copy and MRP4 expression, CEMss cells were grown stepwise to different levels of PMEA resistance and then samples of DNA, RNA and protein were isolated (FIG. 25). The Southern blot revealed negligible changes in MRP4 gene copy for cells grown in up to 2.0 mM PMEA, however, large increases in MRP4 were observed at 10 and 50 mM PMEA (7- and 15-fold, respectively). FISH hybridization analysis of the cells grown in 10 mM and 50 mM PMEA revealed HSRs on chromosome 13 in 92% and 90%, of cells. At 2 mM only one of 50 cells had amplification and this one cell had fewer copies than either the 10 mM or 50 mM cells (not shown). In accord with the increased MRP4 gene copy, MRP4 mRNA strongly increased in cells selected at 10 and 50 mM PMEA. Western blot analysis also indicated a corresponding strong overexpression of immunoreactive MRP4 at 10 mM PMEA and a further increase at 50 mM. It should be emphasized that increased PMEA efflux was observed only when cells overexpressed MRP4 protein and the rate of efflux increased in proportion to the level of MRP4 protein. These studies revealed strong concordance between MRP4 gene copy and expression of MRP4 mRNA and protein.

To confirm that MRP4 confers a dominant phenotype, somatic cell-fusion was used between CEM-r1 and cem.a-gi.oui.5[60]. The cem.agi.oui.5 cell line is very sensitive to azaserine induced death due to the absence of hypoxanthine-guanine phosphoribosyl-transferase[60]. The cem.agi.oui.5 cell line is also obtain-resistant[60], but as sensitive to PMEA as the CEMss cell line (not shown). While the CEM-r1 cells are very PMEA resistant their growth is inhibited by ouabain. Analysis of the fusion cells revealed that all hybrid cells are resistant to PMEA (determined as described in Table 7 legend) and that the range of resistance is from 33.3 to 170 fold, as compared to >250-fold resistance in the CEM-r1 cell line. Immunoblot analysis detected little immunoreactive MRP4 in the cem.agi.oui.5 cell line, but substantial levels of MRP4 in two fusion cell lines (not shown). Southern blot analysis of these cell lines demonstrated increased MRP4 gene copies and FISH analysis of these two fusion cell lines revealed a single copy of chromosome 13 containing a MRP4 HSR in each fusion cell line (not shown).

Because the active forms of these antiretroviral drugs resemble nucleotides the failure to identify a specific transporter linked to nucleotide efflux may be due to the dogma that nucleotides are retained within mammalian cells and not removed by an active transport process. The ABC cassette transporter genes MDR1/Pgp, MRP1, and MRP2 efflux therapeutically important drugs and endogenous substances[64–67], but have not been reported to transport nucleotides. The current studies demonstrate that high levels of the MRP4 gene product are strongly linked to decreased cellular retention and resistance to antiretroviral drugs such as PMEA and AZT. Resistance to PMEA and AZT was associated with MRP4 gene amplification. MRP4 protein overexpression and increased drug efflux, but no change in expression of other ABC transporters (e.g. MDR1/Pgp, or MRP1–MRP3). Moreover, without MRP4 overexpression drug efflux was unchanged. PMEA resistance in the absence of MRP4 overexpression is probably due to the previously described change in adenylate kinase[48] However, AZT is not a substrate for this kinase and there is no evidence for an alteration in thymidine kinase in these cells.

Figure 22:
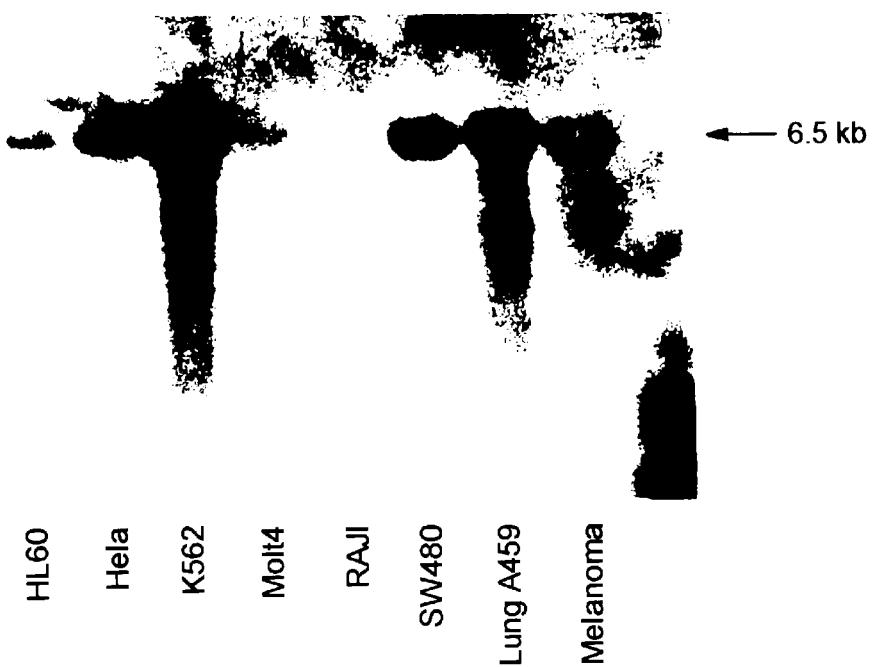
FIG. 22. MPR4 Is Abundantly Expressed In Many Tumor Cells.

Cells vary in their sensitivity to the cytotoxic effects of AZT[68] and this relates to an unusual feature of AZT, i.e., intracellular accumulation of AZTMP, a finding attributed to the poor substrate activity of AZTMP for thymidylate kinase[69–71]. High levels of cellular AZTMP inhibit the biosynthesis of endogenous deoxynucleoside triphosphates[72] and this activity, is reportedly, related to bone marrow toxicity in patients administered AZT[72]. AZTMP may also cause cytotoxicity by decreasing glycosphingolipid biosynthesis[73]. The results reported herein demonstrate that intracellular accumulation of AZTMP is diminished in cells that overexpress MRP4 and this facilitates their survival in high concentrations of AZT. Thus, cellular variation in MRP4 amount may cause differential cellular sensitivity to AZT. In support of this, cells previously reported to "excrete" AZTMP into the media (HL60 and K562[74,75]) have been observed to express high levels of MRP4 (FIG. 22).

Cells selected for doxorubicin or cisplatin resistance do not upregulate MRP4 and therefore increased MRP4 is not a general consequence in the development of drug resistance[49]. The present studies suggest that upregulation of MRP4 may specifically occur secondary to the cellular accumulation of cytotoxic monophosphate nucleosides. In support of this is the finding that cells selected for resistance to PMEG (an acyclic nucleoside guanine derivative with reported antineoplastic potential)[76] also express higher levels of MRP4. Clearly, future studies will evaluate the types of monophosphate substrates utilized by MRP4.

These studies demonstrate that increased MRP4 expression directly correlates with decreased intracellular levels of AZTMP and PMEA. An implication of the current findings is that the currently popular, "highly active antiretroviral therapy", (HAART)[77] that utilizes combinations of highly cytotoxic antiretroviral drugs for long time periods may facilitate selection of MRP4 overexpressing cells leading to a failure of antiretroviral drugs to eradicate HIV in these host cells. Furthermore, given the variation in expression of MRP4 in normal tissues[49] and HIVs ability to infect a variety of cell types [78], it is speculated that MRP4 expression forms a basis for sanctuary growth and evolution of drug resistant HIV[79,80] by decreasing the intracellular drug necessary to inhibit viral replication of HIV. While the present studies link MRP4 overexpression with increased efflux of antiretroviral drugs used for HIV, it is not inconceivable that MRP4 expression could impact chemotherapy of herpesvirus, hepatitis B virus and other retroviruses that use drugs of similar structure.

METHODS

Reagents

The following suppliers were used: AZT (Sigma): [3H]-AZT and metabolite standards. AZTMP, AZTDP and AZTTP (Moravek Biochemicals Brea. Calif.): 3TC (Glaxo Wellcome. Inc., Research Triangle Park. N.C.); PMEA, Bis(POM)PMEA (Dr. Norbert Bischofberger, Gilead Sciences, Foster City, Calif.); MRP1[64], MRP2/cMOAT (genBank accession number R02136), MRP3 (genbank accession number T39953), and MRP4 (genBank accession number R35797). All EST cDNAs were sequenced to confirm authenticity as previously reported cDNA clones.

Cell Lines

The human T-lymphoid cell line CEM-ss (National Institute of Health/National Institute of Allergy and Infectious Diseases: AIDS Research and Reference Program. Ogden BioServices, Rockville, Md.); CEM-r1, a PMEA-resistant variant of CEMss[48].

MRP4 Peptide Antiserum

MRP4 was compared with MRP1 (amino acids 1308–1531). MRP2 (cMOAT; amino acids 1315–1545); MRP3, (amino acids 262–485), MRP5 and MRP6 (amino acids, 1178–1401)[49]. Based upon the multisequence MRP alignment and the hydrophobicity/hydrophilicity, the peptide sequence (SGR LKE YDE PYV LLQ NKE SL) was identified, that would be predicted as specific for MRP4 based upon a query of the BLASTP database. This MRP4 peptide was coupled to KLH and used to produce antiserum in rabbits. The antiserum was affinity purified (Research Genetics) using the MRP4 peptide.

MRP4 Expression Plasmids

A c-terminal fragment of the MRP4 EST containing 171 amino acids was subcloned into the Pinpoint Xa-1 vector (Promega) to generate an in-frame MRP4 expression vector and into Pinpoint Xa-2 to generate an out-of-frame MRP4 expression vector, transformed into bacteria, induced with IPTG and bacterial lysates prepared.

RNase Protection Analysis

Total cellular RNA was isolated as previously described[49].

An MRP4 RNase protection probe (MRP4-239) was generated using the same primers described by Kool et. al.[49], and MRP4 EST as template, subcloning the 239 bp MRP4 fragment into pCR2.1 (InVitrogen) and verifying the sequence. $^{32}$P-labeled MRP4 RNA was transcribed from SpeI linearized MRP4-239. RNase protection assays were carried out according to manufacturers instructions (Ambion). Protected probes were visualized by electrophoresis through denaturing gel followed by autoradiography.

Cell Fusions

Following the procedure of Wolverton et. al.[86], cells were washed and resuspended in phosphate buffered saline. $2 \times 10^6$ cells of each cell line to be fused were mixed and pelleted in a 15 ml conical tube at 22° C. The supernatant was discarded such that no more than 50 ul of the supernatant covered the pellet. To the pellet, 0.5 ml of a 50% v/v solution of PEG in RPMI-1640 was added dropwise over a period of 1 min with gentle tapping. Cells were immediately pelleted, resuspended in OHA medium (ouabain (50 nM), hypoxanthine (100 uM), azaserine (600 uM)) plated in a 96-well dish at $2 \times 10^4$ cells per well and incubated at 37° C. in a humidified incubator with 5% $CO_2$. The cells were nourished with OHA medium at 7 and 14 days post-fusion. Confirmation of cell fusion was determined by both FACS and karyotype analysis.

Several other known inhibitors of ATP-coupled transporters, prostaglandin $A_1$ ($PGA_1$), dipyridamole and NBMPR were also examined for their effect on AZTMP efflux in the two cell lines, CEM-SS and CME-r1. The efflux of AZTMP in CEMr1 cells was markedly inhibited by $PGA_1$ (50 $\mu$M) and DPM (10 $\mu$M) while no effect was observed in the CEM-SS cells. Also, these compounds did not have any effect on the efflux of AZT itself in either the CEM-SS or the CEM-r1 cells.

MATERIALS AND METHODS

Chemicals

PMEA, PMEDAP, PMEG, PMEApp, Bis(POM)PMEA, and monopom-PMEA were kindly provided by Dr. Norbert Bischofberger, Gilead Sciences (Foster City, Calif.). [2,8-$^{3}$H]PMEA (17 Ci/mmol) and [$^{3}$H]bispom-PMEA (21 Ci/mol) were obtained from Moravek Biochemicals (Brea, Calif.). The radioactive compounds were repurified before each experiment. All other nucleoside/nucleotides were purchased from Sigma Chemical Co. (St. Louis, Mo.). AZT was purchased from Sigma Chemical Co. (St. Louis, Mo.). [$^{3}$H]-AZT and the standards for the metabolites, AZT-MP, AZT-DP and AZT-TP were obtained from Moravek Biochemicals (Brea, Calif.). 3TC was from Glaxo Wellcome, Inc. (Research Triangle Park, N.C.).

Cells and Virus

The human T lymphoid cell line CEM-SS and HIV-$1_{IIIB}$ were obtained from the National Institutes of Health/ National Institute of Allergy and Infectious Diseases AIDS Research and Reference Reagent Program (Ogden BioServices, Rockville, Md.). CEM-r1, a PMEA-resistant variant of CEM-SS, was selected as described (48). In a similar procedure, a PMEG-resistant variant of CEM-SS was also selected. Briefly, CEM-SS cells in culture were exposed to increasing concentrations of PMEG over several months. Of the various lines that grew in the presence of high concentration's of PMEG, one of the cell lines was designated as CEM-RPMEG (100-fold resistance to PMEG, $IC_{50}$ value=20 mM) and was cultured for at least 10 generations in PMEA-free medium before subsequent studies. CEM-SS, CEM-r1 and CEM-RPMEG cells were grown in culture in RPMI-1640 medium (BioWhittaker, Walkersville, Md.) supplemented with 10% v:v heat inactivated (56° C., 5 hours) fetal calf serum (HyClone, Logan, Utah) and 2 mM L-glutamine (BioWhittaker, Walkersville, Md.). The cells were incubated at 37° C. in a humidified $CO_2$ (5%) atmosphere.

All cells were maintained in modified Eagle's medium (BioWhittaker, Walkersville, Md.) containing 10% (v/v) heat-inactivated (56°, for 0.5 hr) newborn bovine serum (HyClone, Logan, Utah) and 2 mM L-glutamine. HIV-$1_{IIIB}$ was propagated in CEM-SS cells, and cell-free virus stocks were stored in the vapor phase of liquid $N_2$ cylinders until further use.

Cytotoxicity Assays

Determination of $ED_{50}$

The two cell lines, CEM-SS and CEM-r1 were infected with HIV-IMB at a multiplicity of 0.01, and cultured for 6 days in the presence and absence of different concentrations of test drugs. The extent of virus production was monitored by in in-house p24 antigen capture assay (50).

Determination of $IC_{50}$

All assays were performed in 24-well tissue culture plates (Costar, Cambridge, Ma.). CEM-SS, CEM-r1 or CEM-RPMEG cells were seeded at a density of $2-4 \times 10^5$ cells/well, in the presence or absence of the test compounds, and were allowed to grow for 48 hr (approximately two doublings) at 37° C. in a humidified $CO_2$-controlled atmosphere. At the end of the incubation, the cell concentrations, sizes, and volumes were counted in a Coulter counter (Coulter Electronics, Hialeah. Fla.). The data were used to calculate the 50% growth inhibitory concentrations ($IC_{50}$) of the various test compounds.

RT Assays

The antiviral effects of the different drugs were monitored by RT assays according to previously described procedures (20, 21). CEM-SS or CEM-r1 cells were infected with an inoculum of HIV-$1_{IIIB}$ standardized to contain 1 RT cpm/cell, and the virus-infected cells were seeded at a concentration of $0.2 \times 10^6$ cells/ml in medium containing varying concentrations of PMEA (or other test compounds). After 5 days of incubation, the RT activity of the culture supernates was determined by previously described procedures (22). Briefly, the reactions were carried out in a total volume of 50 ul, using 5 $\mu$g/ml poly(A)$^+$, 1.6 $\mu$g /ml oligo(dT)$_{12-18}$, and 1 $\mu$Ci of [$^{3}$H]TTP in 50 mM Tris, pH 7.8, 75 mM potassium chloride, 5 mM magnesium chloride, 2 mM dithiothreitol, 0.05% Nonidet P-40. The reaction was initiated by addition of 10 ul of virus-containing tissue culture supernatant. After 1 hr of incubation, 10 ul of the reaction mixture were spotted on a Whatman DE-81 tilter paper, air dried, and washed four times with 2×standard saline citrate (0.3 M NaCl, 0.03 M sodium citrate). The filter papers were dried, transferred to a plastic bag containing scintillation cocktail, sealed, and counted in an LKB Betaplate reader. The drug concentrations yielding half-maximal RT activity ($ED_{50}$) was calculated as a measure of the antiviral efficacy of the test compounds, using the nonlinear curve-fitting software Enzfitter (Elsevier Biosoft, Cambridge, UK).

Uptake and Metabolism of [$^3$H]PMEA and [$^3$H]bispom-PMEA

Exponentially growing CEM-SS and CEM-r1 cells were harvested by centrifugation, resuspended at 1×10$^6$ cells/ml in fresh medium in the presence of [$^3$H]PMEA or [$^3$H]bispom-PMEA, and incubated at 37° C. At the indicated time points, aliquots of the cells were removed and centrifuged through Nyosil 50 (W. F. Nye, Inc., New Bedford, Ma.) at 13,000×g for 60 seconds at 4° C. When bispom-PMEA was investigated, an aliquot of the cell-free medium was also removed and analyzed by HPLC for determination of extracellular metabolites. The cell pellet was extracted with 70% ice-cold methanol and the aqueous phase was collected and analyzed for intracellular tritiated PMEA or tritiated bispom-PMEA and their metabolites by using HPLC analysis, essentially as described previously (23, 24). Peaks were identified by chromatography of authentic standards. ps Efflux of [$^3$H]bispom-PMEA and Its Metabolites CEM-SS and CEM-r1 cells were pre-incubated at 1×10$^6$ cells/ml with [$^3$H]bispom-PMEA (2 μCi/ml) for 15 min, washed with ice-cold medium by centrifugation, resuspended at the same concentration in drug-free medium, and maintained at 37° C. At the indicated times, extracts were prepared from the cells and the medium, and the prodrug and its various nucleoside/nucleotide metabolites were analyzed by HPLC as described previously (24).

Quantitation of AZT and Its Metabolites

AZT and its phosphorylated biotransformation products were separated by solid phase extraction (SepPak QMA Cartridges) by using a gradient solvent system that was a slight modification from a previously reported method (51). The cartridges were conditioned with 10% MeOH Ammonium Phosphate Buffer (5 mM, pH 4.0). The sample was loaded onto the column. AZT was eluted with 10% MeOH/Ammonium Phosphate Buffer (5 mm, pH 4.0) and AZTMP was eluted with a 9:1 mixture of 10% MeOH/Ammonium Phosphate Buffer (5 mm, pH 4.0) and 10% MeOH Ammonium Phosphate Buffer (700 mm, pH 4.6). AZTDP and AZTTP were eluted with 10% MeOH Ammonium Phosphate Buffer (700 mm, pH 4.6). The results are set forth in Table 7 below.

TABLE 7

Phosphorylation Of AZT In CEM-SS And CEM-R1 Cells

| Time | Intracellular Concentration (μM) | | | | Extracellular Concentration (nM) | | | |
|---|---|---|---|---|---|---|---|---|
| (Hours) | AZT | AZTMP | AZTDP | AZTTP | AZT | AZTMP | AZTDP | AZTTP |
| CEM-SS | | | | | | | | |
| 4 | 10 | 89 | 0.8 | 1.3 | ND | 46 | ND | ND |
| 8 | 8 | 95 | 0.7 | 1.5 | ND | 151 | ND | ND |
| 24 | 10 | 50 | 0.7 | 1.3 | ND | 555 | ND | ND |
| CEM-r1 | | | | | | | | |
| 4 | 5/1 | 13.6 | 0.22 | 0.36 | ND | 132 | ND | ND |
| 8 | 5.2 | 15.9 | 0.17 | 0.34 | ND | 420 | ND | ND |
| 24 | 4.3 | 12.3 | 0.21 | 0.43 | ND | 1716 | ND | ND |

Both CEM-SS and CEM-r1 cells were incubated with 10 μM AZT and the phosphorylated biotransformation products of AZT present intracellularly were separated by HPLC and quantitated by liquid scintillation counting.

Uptake of [$^3$H]-AZT and Its Metabolites

Exponentially growing CEM-SS and CEM-r1 cells were harvested by centrifugation, resuspended at 1×10$^6$ cells/ml in fresh medium in the presence of [$^3$H]-AZT and incubated at 37° C. At various time periods (0, 10, 20, 30, 40, 60, 90, 120 seconds) from the start of the incubation, aliquots of the cell suspension were removed and centrifuged through Nyosil 50 (W. F. Nye, Inc.,New Bedford, Ma.) at 14,000×g for 60 seconds at 4° C. An aliquot of the top layer (cell free media) was analyzed for the quantitation of AZT and its metabolites. The cell pellet was extracted with 70% methanol/15 MM Tris Buffer, pH 7.0(ice-cold) and the aqueous phase was analyzed for AZT and its metabolites.

Efflux of [$^3$H]-AZT and Its Metabolites

CEM-SS and CEM-r1 cells were pre-incubated at 1×10$^6$ cells/ml with [$^3$H]-AZT (50 μM, 4 uCi/ml) for 60 minutes at 37° C. The suspension was centrifuged at 3,300 rpm for 7 minutes. All but 1 ml of the supernatant medium containing the free drug was aspirated. The cells were quickly resuspended in the remaining medium and were centrifuged through Nyosil 50 at 14,000×g for 60 seconds at 4° C. to remove any traces of the labeled drug. The cell pellet was then washed with ice-cold medium and resuspended at the same concentration in drug-free medium and maintained at 37° C. At the indicated time periods, aliquots of the cell suspension were removed and centrifuged through Nyosil 50 at 14,000×g for 60 seconds at 4° C. An aliquot of the top layer (cell free media) was analyzed for the quantitation of AZT and its metabolites. The cell pellet was extracted with 70% ice-cold methanol and the aqueous phase was analyzed for AZT and its metabolites.

Example 2

MRP4 Is a Mammlian Nucleoside Analog Efflux Pump Present in CEM-r1 Cells: Molecular and Protein Characterization of MRP4

To identify the efflux pump in the multi-drug resistant cells, described in Example 1, resistant and non-resistant (WT) cellular DNA was analyzed. The results described herein below suggested that MRP4 was associated with the cellular drug resistance. The analysis of genomic DNA from the WT and resistant cells indicated that the resistance phenotype is associated with MRP4 gene amplification.

Southern Hybridization

Figures 8A, 8B:
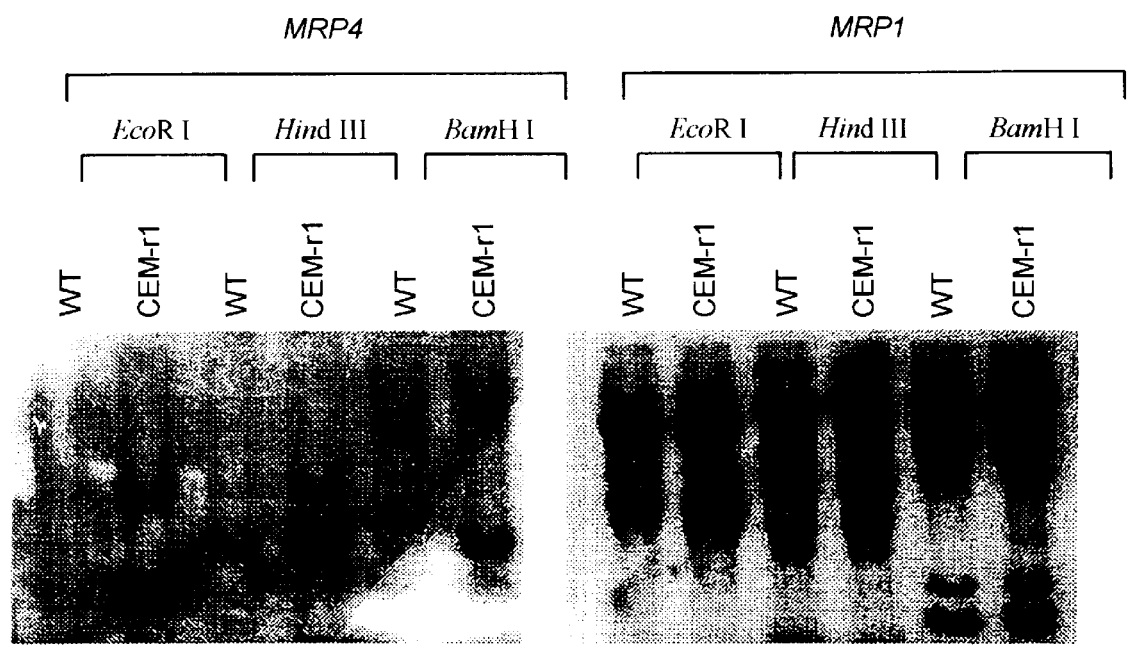
FIGS. 8A–8B. Southern Blot analysis. Genomic DNA was isolated from CEM-SS and CEM-r1 cells as described herein. EcoR I, Hind III, BamH I was used digest the DNA from each cell line, 10 μg of the restricted digest was size fractionated on a 0.8% agarose gel and transferred to a charge modified nylon membrane. Hybridization was performed using $^{32}$P-labeled probes specific for MRP1, MRP2, MRP3 and MRP4 as described herein.

Restriction digests of the genomic DNA from CEM-SS, CEM-r1 and CEM-RPMEG cell lines were probed with $^{32}$P-labeled insert from the human cDNA clones for MRP1, MRP2, MRP3 and MRP4. Results are shown in FIG. 8. MRP4 was selectively amplified (about 20-fold) in the cell variant selected for resistance to PMEA, while no gene amplification was observed in the cell variant selected for resistance to PMEG. The restriction fragments pattern did not reveal any change in gene structure. In addition, no change was observed in the expression of MRP1, MRP2 and MRP3 in the resistant and the wild type cells.

RNAse Protection Assay

Figure 9:
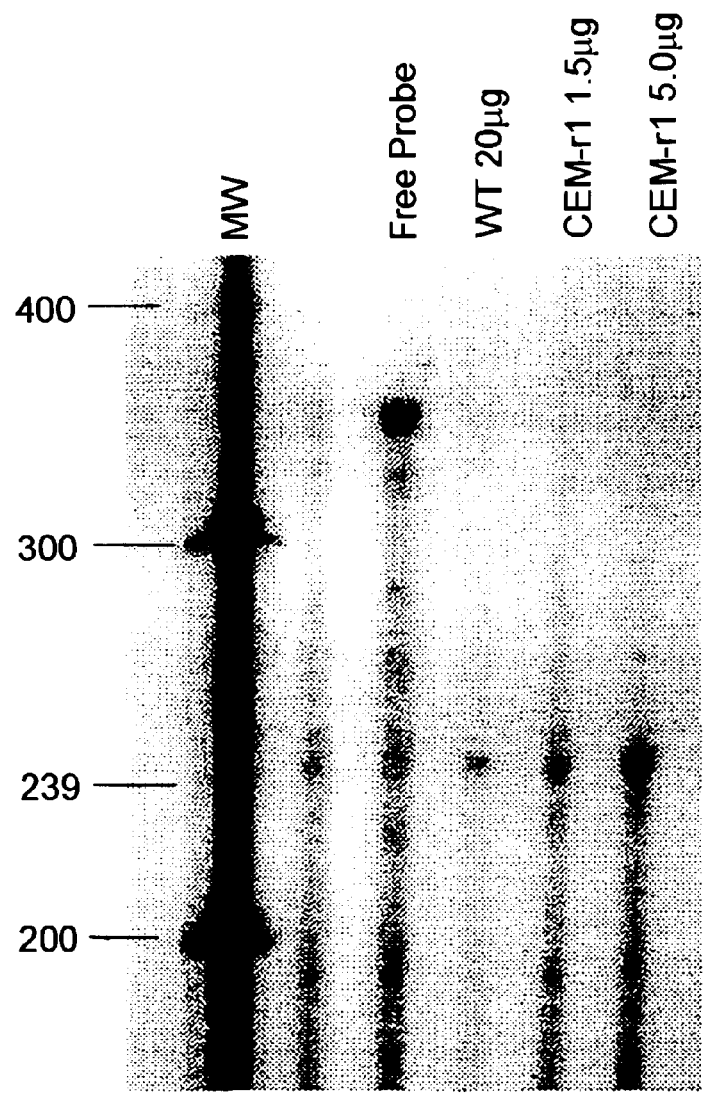
FIG. 9. RNAse protection assay. Total cellular RNA was isolated from CEM-SS and CEM-r1 cells. This RNA was then hybridized at 42° C. with $^{32}$P-labeled antisense RNA probe (359 bp) specific for MRP4 and processed as described herein. The resulting protected mRNA fragment was then resolved on a standard sequencing gel.

Total RNA from CEM-SS, CEM-r1 and CEM-rPMEG cells was probed with a $^{32}$P-labeled RNA probe in-vitro transcribed from MRP4-239 and MRP3-200. MRP4 was overexpressed in both the resistant cell variants selected for resistance with PMEA and PMEG. Results are shown in FIG. 9.

DNA Sequence Analysis

The human EST database was searched for cDNA clones of MRP homologs, EST clones specific for MRP1 and cMOAT were selected. In addition, two clones (clone #61401 and clone #38091 of unknown identity were selected. These clones had an ATP-binding cassette and had 74% and 65% homology, respectively, to the 3' end of CMOAT. Slot blot screening of RNA isolated from the cells using slot blot indicated that clone #38091 showed a 20-17 fold higher expression of a mRNA compared to the sensitive cell. Recently, Kool et al reported two related clones, clone #84966 and clone #38089, identified in the IMAGE Consortium which they designated MRP3 and MRP4 respectively, (49)

Figure 16:
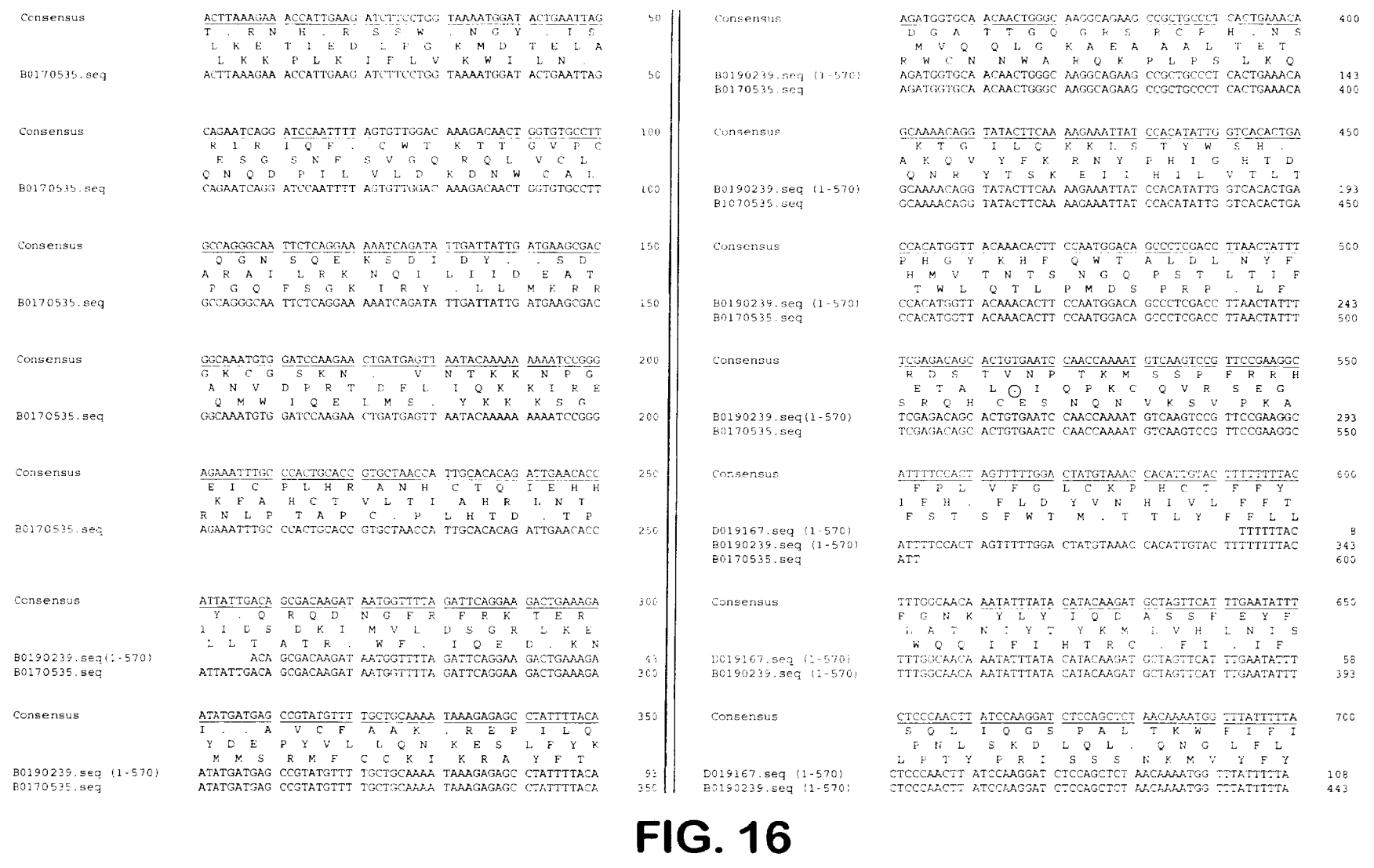

The MRP4 EST (GenBank Accession No.: R35798) was obtained from the IMAGE consortium. Sequencing revealed a 2.275 kb insert (see FIG. 15) which included an open reading frame representing about 171 amino acids (see FIG. 16). An alignment of the MRP4 open reading frame (38091.aa) with the MRP4 EST (labeled MRP4-GenBank) (49) reveals amino acid differences between the two open reading frames and a region of divergence between the two sequences (see FIG. 17). A consensus sequence is shown below the alignment of these two sequences.

PCR Assay to Detect Cellular MRP4

Figure 18:
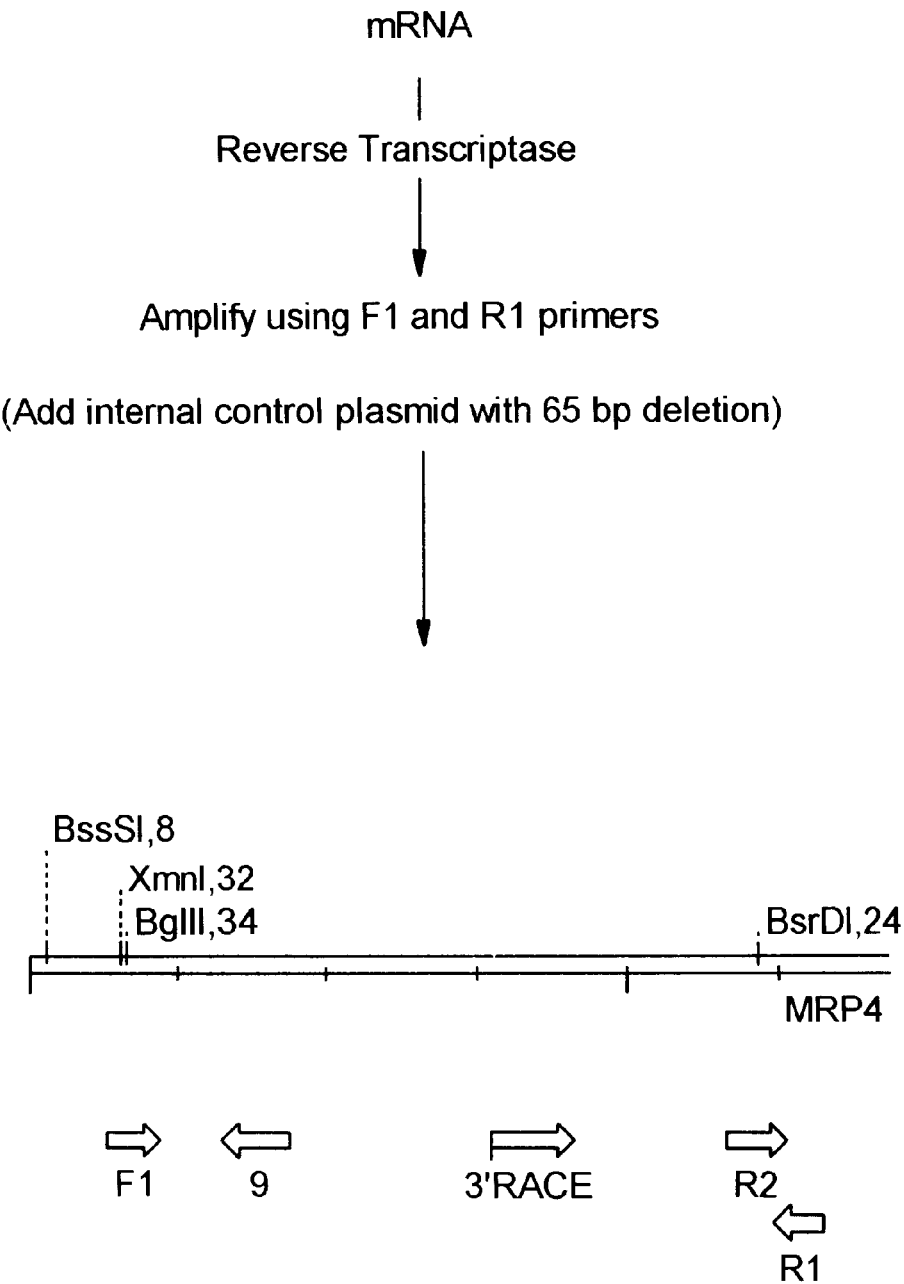
FIG. 18. Scheme for development of a MRP4 PCR assay utilizing an internal control MRP4 plasmid containing a 65bp deletion. Primer 9 and 3' RACE are used to delete 65 bp from MRP4 plasmid, resulting in a plasmid which is useful as an internal control.

Primers were synthesized and used to amplify a 239 bp MRP4 fragment from a first strand cDNA prepared from cellular RNA (See FIG. 18). An internal MRP4 PCR control plasmid was prepared from the MRP4 plasmid. This control plasmid has a 65 bp deletion and this reagent and technique is useful to detect small amounts of MRP4 RNA quantitatively in cells in situations when small numbers of cells are available, rendering detection of MRP4 by Western blot not feasible.

The Walker motif is conserved among the ABC cassette transporters and is found as amino acids VGRTGAGKSS (SEQ ID NO.: 16), represented as the following consensus: (G(X4)GKS) (SEQ ID NO.: 13) (FIG. 19A–19C). An alignment was performed between the MDR type ABC cassette transporters (FIG. 19A) and MRP type (FIG. 19B) (49). The motif was identified in both the N-terminal and C-terminal halves of these molecules. The MRP4-EST clone does not contain a Walker A motif (See FIG. 19B). Therefore, in order to generate a cDNA clone with additional MRP4 sequence, the Walker motif amino acid sequence was used to generate a degenerate oligonucleotide that in combination with a 3' MRP4-specific oligonucleotide amplify a larger MRP4 cDNA. Poly A mRNA was obtained from PMEA resistant cells and reverse transcribed by priming with oligo-dT. The resulting MRP4 products are of the size predicted by the homology with the other ABC cassette transporters.

Sequence Analysis of the 5' 2.7 kb MRP4 cDNA

The 2.7 kb MRP4 cDNA was subcloned into pCR2.1 and sequenced with M13 primers. The sequence analysis reveals that it contains the Walker A motif (FIG. 20).

Genomic Analysis

Genomic DNA was isolated from the wild type (CEM-SS) and resistant (CEM-r1) cells according to standard procedures. EcoR I, Hind III and BamH I were used to digest DNA from each cell line. 10 ug of each restriction digest was size fractionated on an 0.8% agarose gel and transferred to a charge modified nylon membrane. Hybridization was performed according to the standard procedures using $^{32}$P labeled probes specific for MRP1, MRP2, MRP3 and MRP4. The results indicated that MRP4 was amplified in the resistant cells. (See FIG. 8).

Generation of anti-MPR4 Antibodies

Figure 10:
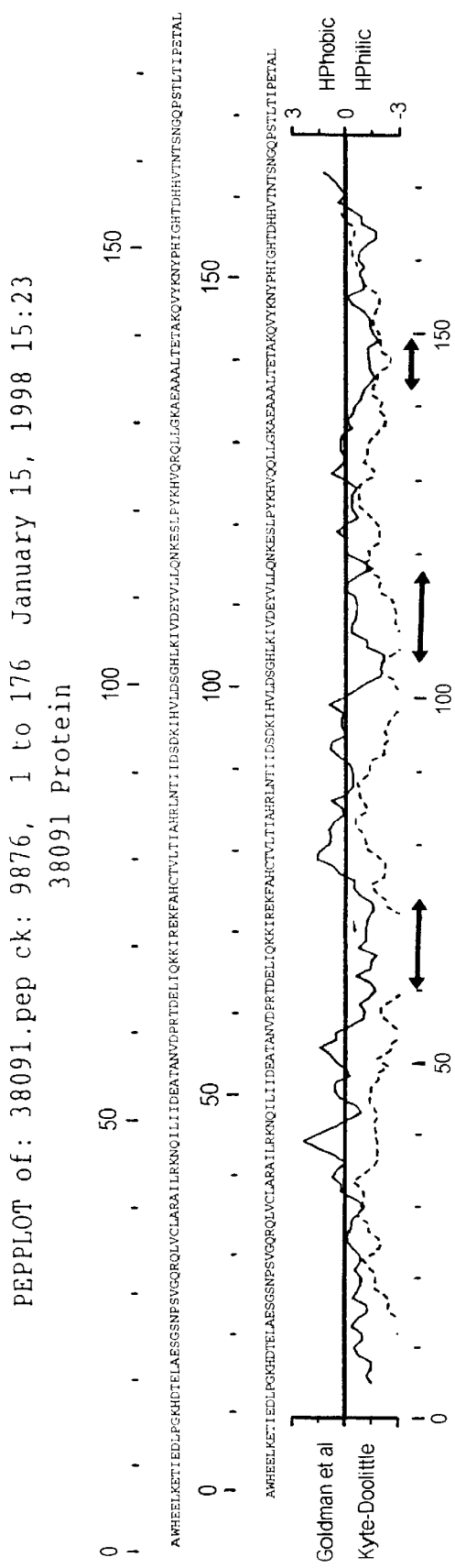
FIG. 10. Hydrophilic domains in the C-terminus of MRP4 (SEQ. ID. NO.:2) predict potential sites for MRP4 peptide synthesis.

The MRP4 sequence (38091.aa) was compared with MRP1 (amino acids 1308–1531), MRP2 (cMOAT: amino acids 1315–1545); MRP3 (amino acids 262–485), MRP5 and MRP6 (amino acids 1178–1401). Based upon the hydrophobicity and hydrophilicity profile analysis (see FIG. 10) and the multisequence MRP alignment (see FIG. 11) two potential peptide sequences were selected (SEQ ID NO.:3 and SEQ ID NO.:4) because they were predicted to be specific for MRP4 and antigenic. Based upon a query of the BLASTP database (see FIG. 12) the following peptide was searched: SGR LKE YDE PYV LLQ NKE SL (SEQ ID No.:4). The peptide was used to immunize rabbits and was predicted to generate MRP4 specific antibody. The peptide was coupled to KLH prior to inoculation into two rabbits.

Western Blot Analysis

Figure 13B:
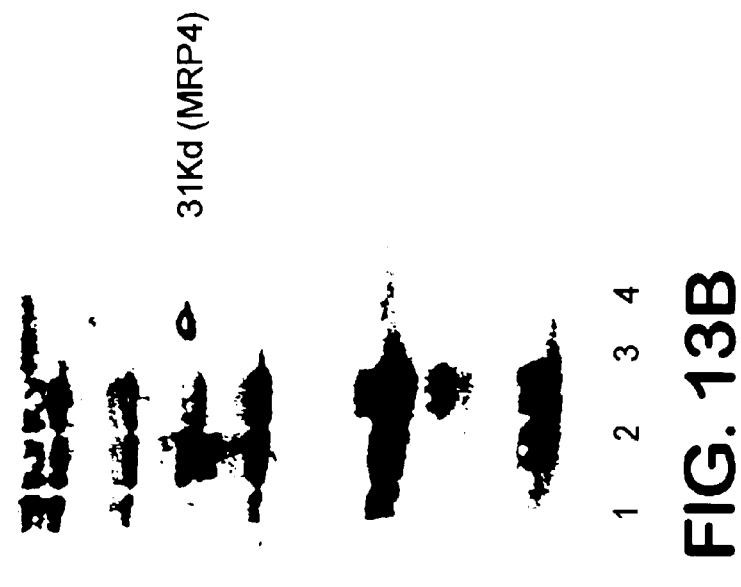
FIGS. 13A–13B. Verification that MRP4 anti-sera detects bacterially expressed MRP4 and that CEMr1 cells specifically overexpress MRP4. Lysates from bacteria containing either the MRP4 protein or not were lysed and fractionated on denaturing polyacrylamide gels. The fractionated protein was transferred to nitrocellulose membranes and (A) probed with streptavidin alkaline phosphatase or (b) MRP4 antisera FIG. 14. The CEM-r1 cells specifically overexpress MRP4 protein and not MRP1 as revealed by Western blot analysis of membrane proteins. R=50™ cells. S=CEM-SS cells.
Figure 13A:
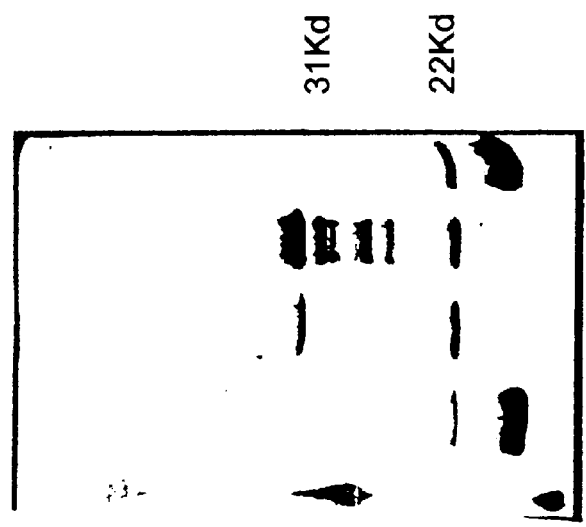
Figure 14:
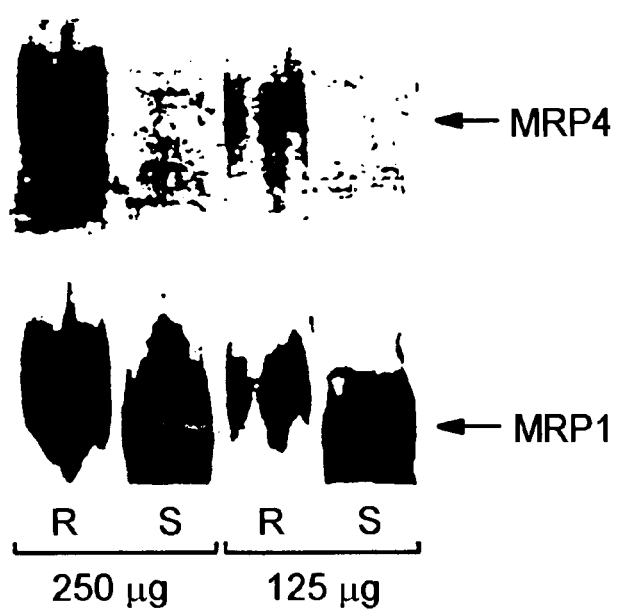

A C-terminal fragment of MRP4 (71 amino acids representing a Hind III/Not I fragment was subcloned into the Pinpoint Xa-1 vector to generate an in-frame MRP4 expression vector and Pinpoint Xa2 to generate an out-of frame MRP4 expression vector. These vectors generate a fusion protein containing MRP4 and a protein that has been tagged with biotin and can therefore be detected by commercial avidin conjugated detection systems using streptavidin alkaline phosphatase detection. These plasmids were transformed into bacteria (see FIG. 13). Bacteria containing either the empty vector, in-frame MRP4 or out-of frame MRP4 were subsequently grown overnight diluted and then induced with IPTG. Subsequently, bacterial lysates were prepared and Western blot analysis was performed and the fusion protein detected with streptavidin alkaline phosphatase detection. FIG. 13A. Bacterial lysates containing either empty vector, MRP in-frame or MRP4 out of frame were separated on PAGE, transferred to a charged modified membrane and probed with peptide antisera to the epitope in human MRP4 representing amino acids SGR LKE YDE PYV LLQ NKE SL (SEQ ID No.: 4). (FIG. 13B).

The bacterial biotinylated MRP4 fusion protein (approximately 31 kD) is recognized by both avidin conjugated alkaline phosphatase and the MRP4 antisera. This antisera was affinity purified and has been used to detect MRP4 overexpression in cells that are resistant to the antiretroviral drugs, AZT PMEA, and PMEG. This antisera is useful in detection of MRP4 in a variety of cell types. Furthermore, the MRP4 biotin fusion construct is valuable for development of a monoclonal antibody to MRP4 after purification of this polypeptide encoding this segment of MRP4.

Western blot analysis (FIG. 25C) illustrates specific overexpression of MRP4 compared with MRP1 on same blot after stripping MRP4. FIGS. 25A and 25B illustrate gene amplification and overexpression of MRP4 respectively.

MATERIALS AND METHODS cDNA Probes for Southern Hybridizations

Human cDNA clones were obtained from the I.M.A.G.E. consortium and were purchased from Genomic Systems (St. Louis, Mo.). For MRP4, the insert of a human cDNA clone (no. 38091, Soares Infant Brain INIB-cDNA library), which contained the 3' terminal end of the gene, was sequenced and isolated for use as a probe.

Isolation of Genomic DNA and Southern Blot Analysis

The genomic DNA was isolated from exponentially growing CEM-SS. CEM-r1 and CEM-RPMEG cells ($1 \times 10^8$ cells for each cell line) according to the standard procedure [20]. Ten ug of DNA from each cell line was separately digested with EcoRI. Hind III and Bam HI. The restriction digests were electrophoresed on a 0.8% agarose gel. The DNA fragments were then transferred to a Nylon membrane and UV-cross-linked using a Stratagene UV cross-linker. Blots were pre-hybridized at 42° C. for 2 hour in 50% formamide, 5×SSPE buffer (1×=150 mM NaCl; 10 mM NaH4PO, pH 7.0; 1 mM EDTA), 5×Denhardt's, 1% SDS and 100 ug/ml of sheared and sonnicated salmon sperm DNA. The blots were hybridized under the same conditions for 16–20 hours with [$\alpha$-$^{32}$P]dCTP-labeled cDNA probe ($2.5 \times 10^6$ cpm/ml; $1 \times 10^9$ cpm/ug of probe). The blot was then washed twice in 2×SSC/0.1% SDS for 30 minutes, at 42° C. This was then followed by two consecutive washes in 0.1×SSC/0.1% SDS for 30 minutes, the first one at 42° C. and the subsequent wash at 55° C.

RNA Isolation

Total RNA was isolated from exponentially growing cells and extracted according to Chomynski and Sacchi.

RNAse Protection Assay

For MRP4, a 239-bp fragment was generated using the primers 5'-CCATTGAAGATCTTCCTGG-3' (forward primer) (SEQ ID NO.:5) and 5'-GGTGTTCAATCTGTGTGC-3' (reverse primer). (SEQ ID NO.:6). The PCR product was subcloned into PCR2.1 cloning vector (Invitrogen Inc.) resulting in plasmid MRP4-239. The sequences of the inserts were confirmed and inserted in the antisense orientation to the T7 promoter. MRP4-239 was linearized with Spe-I (Promega Corp., Madison, Wis.) and in-vitro transcription was carried out using T7 RNA Polymerase (Ambion, Inc.) and $\alpha^{32}$P-CTP to generate an MRP4 riboprobe. RNAse Protection Assay was carried out using the procedure recommended by the manufacturer of the kit (Ambion Inc.). The protected fragments were visualized by electrophoresis through a denaturing 6% acrylamide gel, followed by autoradiography. The amount of MRP4 RNA was calculated using a phosphorimager.

Cell Fusion

Cell fusions were carried out according to the procedure of Wolverton et. al. (60). All steps were carried out at room temperature unless mentioned otherwise. Cells were washed and resuspended in phosphate buffered saline. For the fusion of any two cell variants, $2 \times 10^6$ cells of each cell line were mixed and pelleted in a 15-ml conical tube. The supernatant was discarded such that no more than 50 ul of the supernatant covered the pellet. To the pellet, 0.5 ml of a 50% v/v solution of PEG in RPMI-1640 was added dropwise over a period of 1 minute with gentle tapping of the tube. Cells were immediately pelleted, carefully resuspended in OHA medium and plated in 96-well dishes at $2 \times 10^4$ cells per well. The plates were incubated at 37° C. in a humidified incubator jacket with 5% $CO_2$. The cells were nourished with OHA medium at 7 and 14 days post-fusion.

Example 3

Regulation of MRP4 Expression in Tumor Cells

Figure 23:
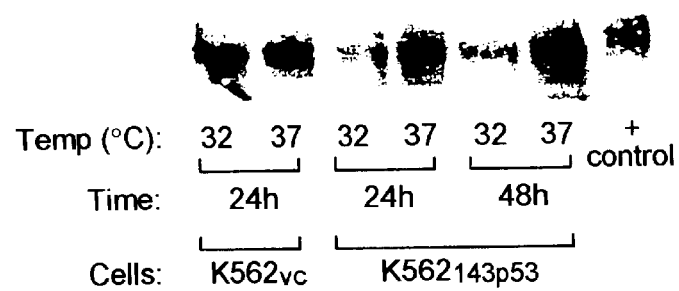
FIG. 23. MRP4 Expression Is Down-Regulated By p53 In K562 Erytholeukemia Cells.

Although MRP4 appears to be expressed in a limited number of normal tissues (49) studies suggest that it is widely expressed in a variety of tumor cells (see FIG. 22) from a variety of lineages representing reproductive epithelia (Hela), hematopoietic cells (HL60, molt4), lung (A459) and colon carcinoma (SW480, also CaCo-2) (see FIG. 22). Because of the high MRP4 expression in K562 and SW480, both of which are p53 null, it was determined whether p53 might play a role in the regulation of MRP4. To accomplish this a K562 cell line was developed that expressed a temperature sensitive p53 allele, such that at 32° C. p53 was in the wildtype conformation and at 37° C. p53 was in the mutant, non-functional conformation (see FIG. 23). These studies revealed that after either 24 or 48 h at 32° C. the level of MRP4 protein was substantially reduced. In contrast, the temperature shift only had a minimal effect on MRP4 expression in the control cells (labeled vc). These studies reveal that the MRP4 gene is repressed by the wildtype p53 and imply that p53 mutation will lead to an upregulation in MRP4 expression thus facilitating resistance to MRP4 substrates.

Example 4

PMEA Transport in a Intestinal Cell Line

Western blot analysis revealed that MRP4 is expressed in LLCPK1 cells (a kidney epithelial cell line) and the CaCo2 cells (an intestinal cell line). Both of these cells polarize in culture to reveal whether a transporter segregates to either the basal or apical membrane.

Figure 24:
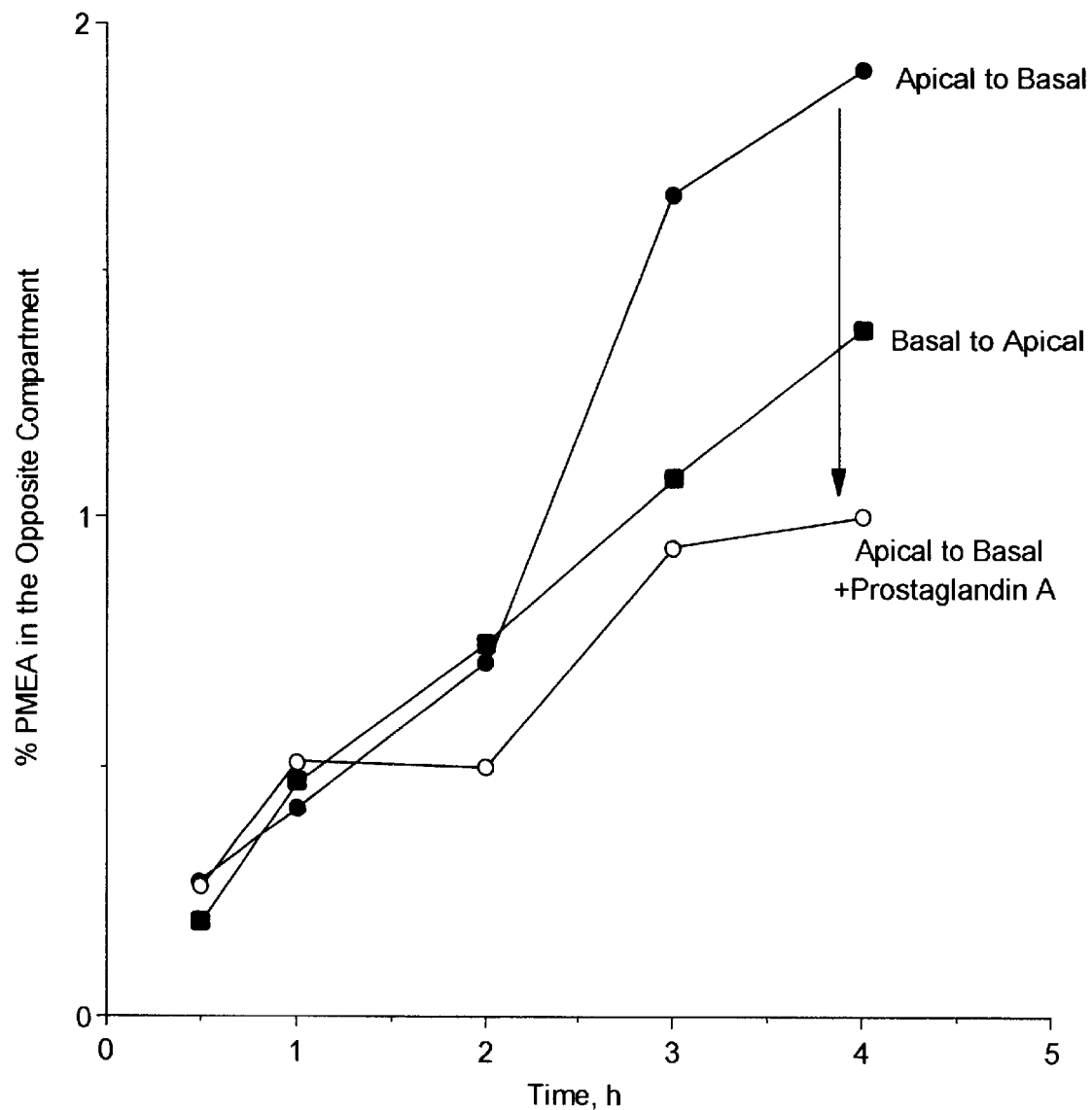
FIG. 24. [³H]-PMEA is Preferentially Sorted to the Basal Compartment in Caco-02 Cells; Basal Flux is Inhibited by Prostaglandin A.

A transwell culture which is permissive for cellular polarization may be used to measure the compartment to compartment flux of putative substrates. Evidence obtained by confocal microscopy revealed that the CaCo-2 cells express MRP4 on the basal lateral membrane and not the apical membrane. Furthermore it has been shown in transwell culture of CaCo-2 that PMEA is more rapidly transported from the apical to the basal side, thus indicating basolateral expressed MRP4 is functional too (see FIG. 24). In addition, it has been determined that prostaglandin A specifically inhibits the apical to basal transport, but has no effect on basal to apical flux. This analysis reveals that specific inhibitors of PMEA mediated transport can be identified in this transwell culture system. In addition, it is possible that expression of MPR4 depending if it is basal or apical (and this may vary by organ cultured) may determine if PMEA or PMEA-like drugs are absorbed.

Example 5

Diagnostic Assay for MRP4 Levels

To determine the amount of MRP4 contained in a sample several diagnostic techniques are used. The sample is prepared in a buffer that stabilizes protein and RNA. Determination of the amount of the protein is performed by immunochemical analysis using either Western blot or immunohistochemistry. A positive control sample from a cell expressing immunoreactive MRP4 may be included for analysis. MRP4 is detected using standard immunochemical methods.

In order to evaluate the amount of MRP4 in an unknown sample the amount of the positive control may be varied and its immunochemical signal be determined. The signal strength can vary as a function of the amount of the immunoreactive MRP4 and is used to construct a standard curve. From the standard curve an estimate of the amount of MRP4 in the unknown sample is performed.

For RNA quantification of MRP4 a cDNA amplification procedure is used based upon reverse-transcriptase generation of a MRP4 cDNA. The kit provides the oligonucleotide primers spanning the region of MRP4 to be amplified and a MRP4 internal control plasmid. In addition, a complementary MRP4 cRNA is included. The MRP4 internal control plasmid contains a small deletion that upon amplification generates a product smaller than that generated from the reverse-transcribed MRP4 cDNA. Thus, based on size, the product of the internal control is readily distinguished from the authentic MRP4 obtained from the patient sample. The ratio of the signal obtained from the patient to the internal control allows estimation of the amount of MRP4 mRNA contained in a sample.

REFERENCES

1. De Clercq, E., A. Holy, I. Rosenberg, T. Sakuma, J. Balzarini, and P. C. Maudgal. 1986. A novel selective broad-spectrum anti-DNA virus agent. *Nature* (Lond.) 323:464–467.
2. Pauwels. R., J. Balzarini, D. Schols, M. Baba, J. Desmyter, I. Rosenberg, A. Holy, and E. De Clercq. 1988. Phosphonylmethoxyethyl purine derivatives, a new class of anti-human immunodeficiency virus agents. *Antimicrob. Agents Chemother.* 32:1025–1030.
3. De Clercq, E., A. Holy, and I. Rosenberg. 1989. Efficacy of phosphonylmethoxyallyl derivatives of adenine in experimental herpes simplex virus and vaccinia virus infections in vivo. *Antimicrob, Agents Chemother.* 33:185–191.
4. Balzarini. I., L. Naesens, P. Herdewijn, I. Rosenberg, A. Holy, R. Pauwels, Baba, D. G. Johns, and E. De Clercq. 1989. Marked in vivo antiretrovirus activity of 9-(2-phosphonylmethoxyethyl)adenine, a selective anti-human immunodeficiency virus agent. *Proc. Natl Acad. Sci. USA* 86:332–336.
5. Balzarini, J., L. Naesens, and E. De Clercq. 1990. Antiretrovirus activity of 9(2-phosphonylmethoxyethyl) adenine (PMEA) in vivo increases when it is less frequently administered. *Int. J. Cancer* 46:337–340.
6. Kim, C. V-, B. Y. Luh, P. F. Misco, J. J. Bronson, M. J. M. Hitchcock, I. Ghazzouti, and J. C. Martin. 1990. Acyclic purine phosphonate analogs as antiviral agents: synthesis and structure-activity relationships. *J. Med. Chem.* 33:1207–1213.
7. Egberink, H., M. Borst, H. Niphuis, J. Balzarini, H. Neu, H. Schellekens, E. De Clercq, M. Horzinek, and M. Koolen. 1990. Suppression of feline immunodefciency virus infection in vivo by 9-(2-phosphonylmethoxyethyl) adenine. *Proc. Natl., Acad. Sci. USA* 87:3087–3091.
8. De Clercq. E. 1991. Broad-spectrum anti-DNA virus and anti-retrovirus activity of phosphonylmethoxyalkylpurines and -pyrimidines. *Biochem. Pharmacol.* 42:963–972.
9. Balzarini. J., A. Holy, J. Jindrich, H. Dvorakova, Z. Hao, R. Snoeck, P. Herdewijn, D. G. Johns, and E. De Clercq. 1991. 9-[(2RS)-3-Fluoro-2-phosphonylmethoxypropyl] derivatives of purines: a class of highly selective antiretroviral agents in vitro and in vivo. *Proc. Natl. Acad. Sci. USA* 88:4961–4965.
10. Balzarini. J., L. Naesens. J. Slachmuylders, H. Niphuis, I. Rosenberg, A. Holy, H. Scheliekens, and E. De Clercq. 1991. 9-(2-Phosphonylmethoxyethyl)adenine effectively inhibits retrovirus replication in vitro and simian immunodeficiency virus infection in rhesus monkeys. *AIDS* 5:21–28.
11. Balzarini. J., Z. Hao, P. Herdewijn. D. G. Johns, and E. De Clercq. 1991. Intracellular metabolism and mechanism of anti-retrovirus action of 9-(2-phosphonylmethoxyethyl)adenine, a potent anti-human immunodeficiency virus compound. *Proc. Natl. Acad. Sci. USA* 88:1499–1503.
12. Thormar. H., J. Balzarini, A. Holy, J. Jindrich. I. Rosenberg, Z. Debyser, J. Desmyter, and E. De Clercq. 1993. Inhibition of Visna virus replication by 2',3'dideoxynucleosides and acyclic nucleoside phosphonate analogs. *Antimicrob. Agents Chemother.* 37:2540–2544.
13. Hartman, K., J. Balzarini, J. Higgins, E. De Clercq, and N. C. Pedersen. 1991. In vitro activity of acyclic nucleoside phosphonate derivatives against feline immunodeficiency virus in Crandell feline kidney cells and feline peripheral blood lymphocytes. *Antiviral Chem. Chemother.* 5:13–19.
14. Tsai. C.-C., K. E. Follis, A. Sabo, R. F. Grant, C. Bartz, R. E. Nolte, R. E. Benveniste, and N. Bischotberger. 1994. Preexposure prophylaxis with 9-(2-phosphonylmethoxyethyl)adenine against simian immunodeficiency virus infection in macaques. *J. Infect. Dis.* 169:260–266.
15. Starrett, J. E., Jr., D. R. Tortolani, M. J. M. Hitchcock, J. C. Martin, and M. Mansuri. 1992. Synthesis and in vitro evaluation of a phosphonate prodrug: bis (pivaloyloxymethyl)-9-(2-phosphonylmethoxyethyl) adenine. *Antiviral Res.* 19:267–273.
16. Collier, A. C., R. W. Coombs, J. Nienow, M. Paradise, H. H. Yang, S. Troxel, Boggs, D. Ebeling, H. S. Jaffe, and L. Corey. 1993. A Phase 1/11 study of 9(2-phosphonylmethoxyethyl)adenine (PMEA) in advanced HIV infection, in *Proceedings of the First National Conference on Human Retroviruses and Related Infections Abstr.* 563:158.
17. Hitchcock. M. J. M., and S. A. Lacy. 1993. Bispivaloytoxymethyl PMEA as an oral prodrug of PMEA: pilot toxicity evaluation in rats, in *Proceedings of the First National Conference on Human Retroviruses and Related infections* Abstr. 567–159.
18. Cerny, J., S. A. Foster, and Y. C. Cheng. 1992. Cell-protecting effect against herpes simplex virus-I and cellular metabolism of 9-(2-phosphonylmethoxyethyl) adenine in HeLa S3 cells. *Mol. Pharmacol.* 42:537–544.
19. Patu, G., S. Stefanelli, M. Rassu, C. Parolin, J. Balzarini, and E. De Clercq. 1991. Cellular uptake of phosphonylmethoxyalkyl derivatives. *Antiviral Res.* 6:115–119.
20. Gong, Y.-F., R. V. Srinivas, and A. Fridland. 1993. 5-Amino-4-imidazolecarboxamide riboside potentiates the metabolism and anti-human immnunodeficiency virus activity of 2',3'-dideoxyinosine. *Mol Pharmacol.* 44:30–36.
21. Gong, Y.-F., D. R. Marshall, R. V. Srinivas, and A. Fridland. 1994. Susceptibilities of zidovudine-resistant variants of human immunodeficiency virus type I to inhibition by acyclic nucleoside phosphonates. *Antimicro. Agents Chemother.* 38:1683–1687.
22. Potts, B. J. "Mini" reverse transcriptase assay, in *Techniques in HIV Research* Aldovini and B. D. Walker, eds.). M. Stockton Press, New York, 103–106 (1990).

23. Connelly, M. C., B. L. Robbins, and A. Fridland. 1993. Mechanism of uptake of the phosphonate analog (S)-1-(3-hydroxy-2-phosphonylmethoxypropyl)cytosine (HPMPC) in Vero cells. *Biochem. Pharmacol,* 46:1053–1057.
24. Srinivas, R. V., B. L. Robbins, M. Connelly, Y.-F. Gong, N. Bischofberger, and A. Fridland. 1993. Metabolism and in vitro antiretroviral activities of bis(pivaloyloxymethyl) prodrugs of acyclic nucleoside phosphonates. *Antimicrob. Agents Chemother.* 37:2247–2250.
25. Tew, K. D., P. J. Houghton, and J. A. Houghton. 1993. Modulation of P-glycoprotein-mediated multidrug resistance, in *Preclinical and Clinical Modulation of Anticancer Drugs* (K. D. Tew, P. J. Houghton, and J. A. Houghton, eds.). CRC Press, Boca Raton, Fla., 125–196.
26. Danks, M. K., J. C. Yalowich, and W. T. Beck. 1987. Atypical multiple drug resistance in human leukemic cell line selected for resistance to tenoposide (VM-26). *Cancer Res.* 47:1297–1301.
27. Cooney, D. A., M. Dalal, H. Mitsuya, J. B. McMahon, M. Nadkarni, J Balzarini, S. Broder, and D. G. Johns. 1986. Initial studies on the cellular pharmacology of 2',3'-dideoxycytidine, an inhibitor of HTLV-III infectivity. *Biochem. Pharmacol.* 35:2065–2068.
28. Johnson, M. A., G. Ahluwalia, M. C. Connelly, D. A. Cooney, S. Broder, D. Johns, and A. Fridland. 1988. Metabolic pathways for the activation of the antiretroviral agent 2',3'-dideoxyadenosine in human lymphoid cells, *J. Biol. Chem.* 263:15354–15357.
29. Johnson, M. A., and A. Fridland. 1989. Phosphorylation of 2',3'-dideoxyinosin, by cytosolic 5'-nucleotidase of human lymphoid cells. *Mol. Pharmacol.* 36:291–295.
30. Bondoc. L. L., Jr., W. M. Shannon, J. A. Secrist III, R. Vince. and A. Fridland 1990. Metabolism of the carbocyclic nucleoside analogue Carbovir, an inhibitor of human immunodeficiency virus, in human lymphoid cells. *Biochemistry* 29:9839–9843.
31. Plagemann, P. G. W., and J. Erbe. 1977. Exit transport of a cyclic nucleotide from mouse L-cells. *J. Biol. Chem.* 252:2010–2016.
32. Rindler, M. J., M. M. Bashor, N. Spitzer, and M. H. Saier, Jr. 1978. Regulation of adenosine 3':5'-monophosphate efflux from animal cells. *J. Biol. Chem.* 253:5431–5436.
33. Meerta, A., I. Votruba, J. Jindrich, A. Holy, T. Cihiar, I. Rosenberg, M. Otmar, and T. Y. Herve. 1992. Phosphorylation of 9-(2-phosphonylmethoxyethyl)adenine and 9-(S)-(3-hydroxy-2-phosphonoylmethoxypropyl)adenine by AMP(dAMP) kinase from L1210 cells. *Biochem. Pharmacol.* 44:2067–2077.
34. Lauder B. A., S. D. Kemp, P. R. Harrigan. 1995. Potential mechanisms for sustained antiretroviral efficacy for AZT-3TC combination therapy. *Science* 269:696–699.
35. Merrill, D. P., M. Moonis, T. C. Chou, M. S. Harris. 1996. Lamivudine or stavudine in two- and three-drug combinations against human immunodeficiency virus type I replication in vitro. *J. Infect. Dis.* 173:355–364.
36. Balzarini, J. & De Clercq. E. 1995. Acyclic purine nucleoside phosphonates as retrovirus inhibitors. pp 41–45. In D J Jeffries and E. De Clercq (ed). Antiviral chemotherapy. John Wiley & Sons. New York, N.Y.
37. Robbins B. L., Fridland A. 1996. Metabolism and therapeutic activity of acyclic adenine phosphonate analogs. *Int. Antiviral News* 4:57–59.
38. Tsai C. C., Follis K. E., Sabo A., Beck T. W., Grant R. F., Bischofberger N., Benveniste R. E., Black R. 1995. Prevention of SIB infection in macaques by (R)-9-(2-phosphonylmethoxypropyl)adenine. *Science* 270:1197–1199.
39. Lavie A., Vetter I. R., Konrad M., Goody R. S., Reinstein J., Schlichting I. 1997. Structure of Thymidylate kinase reveals the cause behind the limiting step in ACT activation. *Nature Structural Biol.* 4:601–604.
40. Lenyon G. L. 1997. AZT monophosphate knocks thymidylate kinase for a loop. *Nature Structural Biol.* 4:5595–5597.
41. Robbins B. L., Greenhaw J., Connelly M. C., Fridland A. 1995. Metabolic pathways for the activation of the antiviral agent 9-(2-phosphonylmethoxyuethyl) adenine in human lymphoid cells. *Antimicrob. Agents Chemother.* 39:2304–2308.
42. Fletcher C. V., Kawle S. P., Pave L. M., Reymel R. P., Acost E. P., Henry K., Erice A, Balfour H. H. 1997. Intracellular triphosphate concentrations of antiretroviral nucleosides as a determinant of clinical response in HIV-infected patients. In: Program and Abstracts of the Fourth Conference on Retroviruses and Opportunistic Infections (Washington, D.C.), p 64:13A.
43. Deeks S. G., Collier A., Lalerzceri J., Pavia A., Rodriguez D., Drew W. L., Toole J., Jagge H. S., Mulato A. S., Lamy P. D., Li W., Cherrington D. M., Hallman N., Kahn J. 1997. Safety and efficacy of adefovir dipivoxil, a novel anti-human immunodeficiency virus therapy in HIV infected adults. *J. Infect. Dis.* 176:1517–1523.
44. Schuurman R., Nijhuis M., Van Leenwen R., Schipper P., DeJong D., Collis P., Danner S. A., Mulder J., Boucher C. A. B. 1885. Rapid change in human immunodeficiency virus type 1 RNA load and appearance of drug-resistant virus populations in persons treated with lamivudine (3TC). *J. Infect. Dis.* 171:1411–1419.
45. Hammer S. M. 1996. Advances in antiretroviral therapy and viral load monitoring. *AIDS* 10 (Suppl 3) S1–S3.
46. Sommadosi J. P., Valantin M. A., Zhou X. J., Xie M. Y., Moore J., Calvez D., Katlama M. 1998. Intracellular phosphorylations of stavudine correlates with their anti-retroviral activity in naive and zidovudine experienced HIV-infected patients. In: Program and Abstracts of the Fifth Conference on Retroviruses and Opportunistic Infections (Chicago, Ill.). Abstract 362.
47. Gottesman M. M., Pastan I. 1993. Biochemistry of multidrug resistance mediated by the multidrug resistance transporter. *Annu. Rev. Biochem.* 62:385–427.
48. Robbins B. L., Connelly M. C., Marshall D., Srinivas R. V., Fridland A. 1995. A human T lymphoid cell variant resistant to the inhibitory effects of the acyclic nucleoside phosphonate, 9-(2-phosphorylmethoxyethyl) adenine (PMEA) shows increased efflux of the agent. *Molecul. Pharmacol.* 47:391–397.
49. Kool M., Detlaas M., Schefter G. L., Scheper R. J., Michiel J. T., Eick V., Juijn J. A., Baas F., Borst P. 1997. Analysis of Expression of cMOAT, MRP3, MRP4, MRP5 Homologues of the multidrug resistance associated protein gene MRP1 in human cancer cell lines. *Cancer Res* 57:3537–3547.
50. Weislow O. S., Kiser R., Fine L., Bader J., Shoemaker H., Boyd M. R. 1989. New soluble formazan assay for HIV-1 cytopathic effects: Application to high-flux screening of synthetic and natural products for AID antiviral activity. *J. Natl Cancer Inst* 81:577–586.
51. Robbins B. L., Waibel B. H., Fridland A. 1996. Quantitation of intracellular zidovudine phosphates by use of combined cartridge-radioimmunoassay methodology. *Antimicrob. Agents Chemother.* 40:2651–2654.
52. Barrand M. A., Bagrij T., Neo S. Y. 1997. Multidrug resistance-associated protein: a protein distinct from P-glycoprotein involved in cytotoxic drug expulsion *Gen. Pharmacol.* 28: 639–645.
53. Van Veen H. W., Konings W. N. 1998. The ABC family of multidrug transporters in microorganisms. *Biochim. Biophys. Acta* 1365:31–36.
54. Keppler D., Leier I., Jedlitschky G., König J. 1998. ATP-dependent transport of glutathione S-conjugates by the multidrug resistance protein MRP1 and its apical isoform MRP2. *Chem. Biol. Interact.* 111–112: 153–161.
55. Pitlik E., HollóZ. 1996. Significance of multidrug resistance in the therapy of malignant tumors *Orv. Hetil.* 137: 2783–90.
56. Lee K., Belinsky M. G., Bell D. W., Testa J. R., Kruh G. D. 1998. Isolation of MOAT-B, a widely expressed multidrug resistance-associated protein/canalicular multispecific organic anion transporter-related transporter. *Cancer Res.* 58: 2741–7.
57. Hoedemaeker F. J., Davidson A. R., Rose D. R. 1998. A model for the nucleotide-binding domains of ABC transporters based on the large domain of aspartate aminotransferase. *Proteins* 30: 275–86.
58. Broeks A., Gerrard B., Allikmets R., Dean M., Plasterk R. H., 1996. Homologues of the human multidrug resistance genes MRP and MDR contribute to heavy metal resistance in the soil nematode Caenorhabditis elegans. *EMBO J.* 15: 6132–6143.
59. Cole S. P., Bhardwaj G., Gerlach J. H., Mackie J. E., Grant C. E., Almquist K. C., Stewart A. J., Kurz E. U., Duncan A. M., Deeley R. G. 1992. Overexpression of a transporter gene in a multidrug-resistant human lung cancer cell line *Science* 258: 1650–1654.
60. Wolverton J. S., Danks M. K., Schmidt C. A., Beck W. T. 1989. Genetic characterization of the multidrug-resistant phenotype of VM-26-resistant human leukemic cells. *Cancer Res.* 49: 2422–6.
61. Allikmets, R., Gerrard, B., Hutchinson, A. & Dean, M. 1996. Characterization of the human ABC superfamily: Isolation and mapping of 21 new genes using the expressed sequence tags database. *Hum. Mol. Genet.* 5: 1649–1655.
62. *Gene amplification in mammalian cells* (Marcel Dekker, Inc., New York, 1993).
63. Boer, R., Haas. S. & Schodl, A. 1994. Influence of dexniguldipine-HCl on rhodamine-123 accumulation in a multidrug-resistant leukaemia cell line: comparison with other chemosensitisers. *Euro. Jnl. Cancer* 30A: 1117–11123.
64. Loe, D. W., Deeley, R. G. & Cole, S. P. C. 1996. Biology of the multidrug resistance-associated protein, MRP. *Euro. Jnl. Cancer* 32A:945–957.
65. Leier, I., Jedlitschky, G., Buchholz. U., Cole, S. P. C., Deeley, R. G., et al. 1994. The MRP gene encodes an ATP-dependent export pump for leukotriene C4 and structurally related compounds. *J. Biol. Chem.* 269:27807–27810.
66. Borst. P. & Schinkel, A. H. 1996. What Have We Learnt Thus Far From Mice With Disrupted P-glycoprotein Genes? *Euro. Jnl. Cancer* 32A:985–990.
67. Evers, R., Kool. M., van Deemter, L., Janssen, H., Calafat, J., et al. 1998. Drug export activity of the human canalicular multispecific organic anion transporter in polarized kidney MDCK cells expressing cMOAT (MRP2) cDNA. *J. Clin. Invest.* 101:1310–1319.
68. Balzarini. J., Pauwels, R., Baba, M., Herdewijn, P., de Clercq, E., et al. 1988. The in vitro and in vivo anti-retrovirus activity, and intracellular metabolism of 3'-azido-2',3'-dideoxythymidine and 2',3'-dideoxycytidine are highly dependent on the cell species. *Biochem. Pharm.* 37:897–903.
69. Furman, P. A., Fyfe, J. A., St.Clair, M. H., Weinhold, K., Rideout, J. L., et al. 1986. Phosphorylation of 3'-azido-3'-deoxythymidine and selective interaction of the 5'-triphosphate with human immunodeficiency virus reverse transcriptase. *Proc. Natl. Acad. Sci. U. S. A.* 83:8333–8337.
70. Lavie, A., Schlichting, I., Vetter. I. R., Konrad, M., Reinstein, J., et al. 1997. The bottleneck in AZT activation. *Nature Med.* 3:922–924.
71. Balzarini, J., Degreve, B. & DeClercq, E. 1998. Improving AZT efficacy. *Nature Med* 4:132.
72. Sommadossi, J. P. 1993. Nucleoside analogs: similarities and differences. *Clin. Inf. Dis.* 16 Suppl 1, S7–15.
73. Yan, J-P., Ilsley. D. D., Frohlick. C., Steet. R., Hall, E. T., et al. 1995. 3'-Azidothymidine (Zidovudine) inhibits glycosylation and dramatically alters glycosphingolipid synthesis in whole cells at clinically relevant concentrations. *J. Biol. Chem.* 270:22836–22841.
74. Frick, L. W., Nelson, D. J., St.Clair, M. H., Furman, P. A. & Krenitsky, T. A. 1988. Effects of 3'-azido-3'-deoxythymidine on the deoxynucleotide triphosphate pools of cultured human cells. *Biochem. Biophys. Res. Commun.* 154:124–129.
75. Fridland., A., Connelly. M. C. & Ashmun, R. 1990. Relationship of deoxynucleotide changes to inhibition of DNA synthesis induced by the antiretroviral agent 3'-azido-3'-deoxythymidine and release of its monophosphate by human lymphoid cells (CCRF-CEM). *Mol. Pharmacol.* 37:665–670.
76. Karmata, P., Compton, M. L. & Paborsky, L. R. 1998. Mechanism of anti-proliferative activity of PMEG, a novel acyclic nucleotide analog. *Proc. Amer. Assoc. Cancer Res.* 39:3198. (Abstract)
77. Berger. E. A., Mioss. B. & Pastan. I. 1998. Reconsidering targeted toxins to eliminate HIV infection: You gotta have HAART. *Proc. Natl. Acad. Sci. USA* 95:11511–11513.
78. Levy, J. A. Pathogenesis of human immunodeficiency virus infection, in *Viral Oncogenesis and Cell Differentiation* (eds Diamond, L. & Wolman. S. R.) 58–68 (The New York Academy of Sciences, New York, 1989).
79. Kepler, T. B. & Perelson, A. S. 1998. Drug concentration heterogeneity facilitates the evolution of drug resistance. *Proc. Natl. Acad. Sci. USA* 95:11514–11519.
80. Medina. D. J., Tung, P. P., Serner-Tung, M. B., Nelson, C. J., Mellors, J. W., et al. 1995. Sanctuary growth of human immunodeficiency virus in the presence of 3'-azido-3'-deoxythymidine. *J. Virol.* 69:1606–1611.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A method for identifying a compound that affects nucleotide transport in cells or tissues comprising:
   (a) contacting cells or tissues which express MRP4 with a test compound;
   (b) determining a first level of expression of MRP4 protein in said cells or tissues; and
   (c) comparing the first level of MRP4 protein expression with a second level of expression of MRP4 protein in said cells or tissues which is determined in the absence of the compound, wherein a difference in the first and second levels of expression of MRP4 protein is indicative of the ability of the compound to affect nucleotide transport in said cells or tissues.

2. The method of claim 1, wherein said cells or tissues are selected from the group consisting of cell lysate, a cell-free translation expression system, an isolated cell and a cultured host cell.

3. A compound, previously unknown, identified by the method of claim 1.

4. A method for identifying a compound that affects nucleotide transport in cells or tissues comprising:
   (a) contacting cells or tissues which express MRP4 protein with a test compound;
   (b) determining a first level of MRP4 protein activity in said cells or tissues; and
   (c) comparing the first level of MRP4 protein activity with a second level of MRP4 protein activity in said cells or tissues which is determined in the absence of the compound, wherein a difference in the first and second levels of MRP4 protein activity is indicative of the ability of the compound to affect nucleotide transport in said cells or tissues.

5. The method of claim 4, step (a) comprising first introducing the nucleic acid encoding a MRP4 protein into an expression system and causing the expression system to express the nucleic acid under conditions whereby a MRP4 protein is produced.

6. The method of claim 4, wherein step (b) comprises measuring the efflux of an antimicrobial agent from a cell in the presence of the compound.

7. The method of claim 6, wherein the agent is selected from the group consisting of nucleoside inhibitors and protease inhibitors.

8. The method of claim 6, wherein the agent is AZT.

9. The method of claim 4, wherein said cells or tissues are selected from the group consisting of cell lysate, a cell-free translation expression system, an isolated cell and a cultured host cell.

10. A compound, previously unknown, identified by the method of claim 4.

11. The method of claim 2 or 4, wherein the compound is a peptide, a peptidomimetic, a nucleic acid, a polymer, or a small molecule.

12. The method of claim 2 or 4, wherein the compound is bound to a solid support.

13. A method of modulating nucleotide transport in cells or tissues, comprising contacting said cells or tissues with the compound of claim 10.

14. A pharmaceutical composition which comprises the compound of claim 10 and a pharmaceutically acceptable carrier.

15. The pharmaceutical composition of claim 14, wherein the carrier is a diluent, an aerosol, a topical carrier, an aqueous solution, a nonaqueous solution or a solid carrier.

16. A method for treating a condition in a subject which comprises administering to the subject an amount of the pharmaceutical composition of claim 14, effective to treat the condition in the subject.

17. The method of claim 16, wherein the condition is selected from the group consisting of an infectious, immunodeficiency, neurological, renal, pulmonary, hepatic, cardiovascular, neoplastic and malignant condition.

18. The method of claim 17, wherein the condition is a result of virus, bacterial, or yeast infection.

19. A method for identifying subjects at risk for resistance to anti-microbial agents that are associated with nucleotide transport-related drug resistance comprising:
   (a) identifying by the method of claim 2 or 4, the expression or activity of MRP4 protein in a sample from the subject;
   (b) measuring a level of MRP4 protein expression or activity present in the sample from the subject;
   (c) measuring a level of MRP4 protein expression or activity present in a control sample wherein said control sample is known to have a level of MRP4 protein expression or activity that is not indicative of nucleotide transport-related drug resistance; and (d) comparing the level of MRP4 protein expression or activity present in said control sample with the level of MRP4 protein expression or activity in said sample from said subject, wherein an elevated amount of MRP4 protein expression or activity present in the sample from the subject indicates increased risk for resistance to anti-microbial agents associated with nucleotide transport-related drug resistance.

20. A method of identifying an anti-microbial agent which is associated with nucleotide transport-related drug resistance and which is refractive to MRP4 protein efflux activity comprising:

(a) contacting a cell expressing MRP4 protein with an anti-microbial agent;

(b) measuring the amount of said agent in the cell;

(c) incubating the cell with the agent;

(d) comparing the amount of agent in the cell before and after the incubation of step (c), wherein no substantial decrease in the amount of the agent in the cell after the incubation of step (c) indicating that said agent is refractive to MRP4 protein efflux activity.

21. The method of claim 20, step (a) further comprising labeling the agent with a detectable marker.

22. The method of claim 21, wherein the detectable marker is a radiolabeled molecule, a fluorescent molecule, an enzyme, a ligand, or a magnetic bead.

23. The agent identified by the method of claim 20.

24. A pharmaceutical composition comprising the agent of claim 20 and a pharmaceutically acceptable carrier.

* * * * *

SEQUENCE LISTING

<160> NUMBER OF SEQ ID NOS: 27

<210> SEQ ID NO 1
<211> LENGTH: 6
<212> TYPE: DNA
<213> ORGANISM: homo sapien

<400> SEQUENCE: 1 atatat                                                                      6

<210> SEQ ID NO 2
<211> LENGTH: 7
<212> TYPE: PRT
<213> ORGANISM: homo sapien

<400> SEQUENCE: 2

Ala Asx Cys Asp Glu Phe Gly
 1               5

<210> SEQ ID NO 3
<211> LENGTH: 176
<212> TYPE: PRT
<213> ORGANISM: homo sapien

<400> SEQUENCE: 3

Ala Trp His Glu Glu Leu Lys Glu Thr Ile Glu Asp Leu Pro Gly Lys
 1               5                  10                  15

Met Asp Thr Glu Leu Ala Glu Ser Gly Ser Asn Arg Ser Val Gly Gln
                20                  25                  30

Arg Gln Leu Val Cys Leu Ala Arg Ala Ile Leu Arg Lys Asn Gln Ile
            35                  40                  45

Leu Ile Ile Asp Glu Ala Thr Ala Asn Val Asp Pro Arg Thr Asp Glu
        50                  55                  60

Leu Ile Gln Lys Lys Ile Arg Glu Lys Phe Ala His Cys Thr Val Leu
65                  70                  75                  80

Thr Ile Ala His Arg Leu Asn Thr Ile Ile Asp Ser Asp Lys Ile Met
                85                  90                  95

Val Leu Asp Ser Gly Arg Leu Lys Glu Tyr Asp Glu Pro Tyr Val Leu
            100                 105                 110

Leu Gln Asn Lys Glu Ser Leu Phe Tyr Lys Met Val Gln Gln Leu Gly
        115                 120                 125

Lys Ala Glu Ala Ala Leu Thr Glu Thr Ala His Gln Val Tyr Phe
    130                 135                 140

Lys Arg Asn Tyr Pro His Ile Gly His Thr Asp His Met Val Thr Met
145                 150                 155                 160

Thr Ser Asn Gly Gln Pro Ser Thr Leu Thr Ile Phe Glu Thr Ala Leu
                165                 170                 175

<210> SEQ ID NO 4
<211> LENGTH: 20
<212> TYPE: PRT
<213> ORGANISM: homo sapien

<400> SEQUENCE: 4

Ser Gly Arg Leu Lys Glu Tyr Asp Glu Pro Tyr Val Leu Leu Gln Asn
 1               5                  10                  15

Lys Glu Ser Leu
            20

<210> SEQ ID NO 5
<211> LENGTH: 18
<212> TYPE: DNA
<213> ORGANISM: homo sapien

<400> SEQUENCE: 5
acagtacgat aaacttgc                                                   18

<210> SEQ ID NO 6
<211> LENGTH: 2275
<212> TYPE: DNA
<213> ORGANISM: homo sapien
<220> FEATURE:
<221> NAME/KEY: misc_feature
<222> LOCATION: (1)...(2275)
<223> OTHER INFORMATION: n = A,T,C or G

<400> SEQUENCE: 6

| | | | | | |
|---|---|---|---|---|---|
| acttaaagaa | accattgaag | atcttcctgg | taaaatccat | actgaattag | cagaatcagg | 60 |
| atccaatttt | agtgttggac | aaagacaact | ggtgtgcctt | gccagggcaa | ttctcaggaa | 120 |
| aaatcagata | ttgattattg | atgaagcgac | ggcaaatgtg | gatccaagaa | ctgatgagtt | 180 |
| aatacaaaaa | aaaatccggg | agaaatttgc | ccactgcacc | gtgctaacca | ttgcacacag | 240 |
| attgaacacc | attattgaca | gcgacaagat | aatggtttta | gattcaggaa | gactgaaaga | 300 |
| atatgatgag | ccgtatgttt | tgctgcaaaa | taaagagagc | ctattttaca | agatggtgca | 360 |
| acaactgggc | aaggcagaag | ccgctgccct | cactgaaaca | gcaaaacagg | tatacttcaa | 420 |
| aagaaattat | ccacatattg | gtcacactga | ccacatggtt | acaaacactt | ccaatggaca | 480 |
| gccctcgacc | ttaactattt | tcgagacagc | actgtgaatc | caaccaaaat | gtcaagtccg | 540 |
| ttccgaaggc | attttccact | agttttggga | ctatgtaaac | cacattgtac | ttttttttac | 600 |
| tttggcaaca | aatatttata | catacaagat | gctagttcat | ttgaatattt | ctcccaactt | 660 |
| atccaaggat | ctccagctct | aacaaaatgg | tttattttta | tttaaatgtc | aatagttgtt | 720 |
| ttttaaaatc | caaatcagag | gtgcaggcca | ccagttaaat | gccgtctatc | aggttttgtg | 780 |
| ccttaagaga | ctacagagtc | aaagctcatt | tttaaaggag | taggacaaag | ttgtcacagg | 840 |
| ttttttgttgt | tgtttttatt | gcccccaaaa | ttacatgtta | atttccattt | atatcaggga | 900 |
| ttctatttac | ttgaagactg | tgaagttgcc | attttgtctc | attcttttct | ttgacataac | 960 |
| taggatccat | tatttcccct | gaaggcttct | tgttagaaaa | tagtacagtt | acaaccaata | 1020 |
| ggaacaacaa | aaaggaaaaa | gtttgtgaca | ttgtagtagg | gagtgtgtac | cccttactcc | 1080 |
| ccatcaaaaa | aaaaatccat | acatggttaa | aggatagaag | ggcaatattt | tatcatatgt | 1140 |
| tctaaaagag | aaggaagaga | aaatactact | ttctcaaaat | ggaagccctt | aaaggtgctt | 1200 |
| tgatactgaa | agacacaaat | gtgaccgtcc | atcctccttt | agagttgcat | gacttggaca | 1260 |
| cggtaactgt | tgcagtttta | gactcagcat | tgtgacactt | cccaagaagg | ccaaacctct | 1320 |
| aaccgacatt | cctgaaatac | gtggcattat | tcttttttgg | atttctcatt | tatggaaggc | 1380 |
| taaccctctg | ttgaccgtaa | gccttttggt | ttgggctgta | ttgaaatcct | ttctaaattg | 1440 |
| catgaatagg | ctctgctaac | gtgatgagac | aaactgaaaa | ttattgcaag | cattgactat | 1500 |
| aattatgcag | tacgttctca | ggatgcatcc | aggggttcat | tttcatgagc | ctgtccaggt | 1560 |
| tagtttactc | ctgaccacta | atagcattgt | catttgggct | ttctgttgaa | tgaatcaaca | 1620 |
| aaccacaata | cttcctggga | cctttgtac | tttatttgaa | ntatgagtct | ttaattttc | 1680 |

-continued

```
cctgatgatg gtggctgtaa tatgttgagt tcagttttact aaaggtttta ctattatggt    1740
ttgaagtgga gtctcatgac ctctcagaat aaggtgtcac ctccctgaaa ttgcttatat    1800
gtatatagac atgcacacgt gtgcatttgt ttgtatacat atatttgtcc ttcgtatagc    1860
aagttttttg ctcatcagca gagagcaaca gatgttttat tgagtgaagc cttaaaaagc    1920
acacaccaca cacagctaac tgccaaaata cattgaccgt agtagctgtt caactcctag    1980
tacttagaaa tacacgtatg gttaatgttc agtccaacaa accacacaca gtaaatgttt    2040
attaatagtc atggttcgta ttttaggtga ctgaaattgc aacagtgatc ataatgcggt    2100
ttgttaaaac gatagctata ttcaaaatgt ctatatgttt atttggactt ttgaggttaa    2160
agacagtcat ataaacgtcc tgtttctgtt ttaatgttat catagaattt tttaatgaaa    2220
ctaaattcaa ttgaaataaa tgatagtttt natttccaaa aaaaaaaaaa aaaaa        2275
```

<210> SEQ ID NO 7
<211> LENGTH: 23
<212> TYPE: DNA
<213> ORGANISM: homo sapien

<400> SEQUENCE: 7
ttgcaacgaa atccaagaga tat                                              23

<210> SEQ ID NO 8
<211> LENGTH: 162
<212> TYPE: PRT
<213> ORGANISM: homo sapien
<220> FEATURE:
<221> NAME/KEY: VARIANT
<222> LOCATION: (1)...(162)
<223> OTHER INFORMATION: Xaa = Any Amino Acid

<400> SEQUENCE: 8

```
Leu Lys Glu Thr Ile Glu Asp Leu Pro Gly Lys Met Asp Thr Glu Leu
  1               5                  10                  15

Ala Glu Ser Gly Ser Asn Phe Ser Val Gly Gln Arg Gln Leu Val Cys
             20                  25                  30

Leu Ala Arg Ala Ile Leu Arg Lys Asn Gln Ile Leu Ile Ile Asp Glu
         35                  40                  45

Ala Thr Ala Asn Val Asp Pro Pro Thr Asp Glu Leu Ile Gln Lys Lys
     50                  55                  60

Ile Arg Glu Lys Phe Ala His Cys Thr Val Leu Thr Ile Ala His Arg
 65                  70                  75                  80

Leu Asn Thr Ile Ile Asp Ser Asp Lys Ile Met Val Leu Asp Ser Gly
                 85                  90                  95

Arg Leu Lys Glu Tyr Asp Glu Pro Tyr Val Leu Leu Gln Asn Lys Glu
            100                 105                 110

Ser Leu Phe Tyr Lys Met Val Gln Gln Leu Gly Lys Ala Glu Xaa Xaa
        115                 120                 125

Xaa Leu Thr Glu Thr Ala Lys Xaa Val Tyr Phe Lys Arg Asn Xaa Xaa
    130                 135                 140

His Ile Gly Asp Xaa His Met Val Thr Asn Xaa Xaa Asn Gly Xaa
145                 150                 155                 160

Xaa Ser
```

<210> SEQ ID NO 9
<211> LENGTH: 350
<212> TYPE: PRT
<213> ORGANISM: homo sapien

-continued

```
<400> SEQUENCE: 9

Val Gln Ile Leu Lys Gly Leu Asn Leu Lys Val Gln Ser Gly Gln Thr
1               5                   10                  15

Val Ala Leu Val Gly Asn Ser Gly Cys Gly Lys Ser Thr Thr Val Gln
            20                  25                  30

Leu Leu Gln Arg Leu Tyr Asp Pro Thr Glu Gly Val Val Ser Ile Asp
        35                  40                  45

Gly Gln Ile Lys Ile Leu Lys Gly Leu Asn Leu Lys Val Gln Ser Gly
    50                  55                  60

Gln Thr Val Ala Leu Val Gly Lys Ser Gly Cys Gly Lys Ser Thr Thr
65                  70                  75                  80

Val Gln Leu Leu Gln Arg Leu Tyr Asp Pro Thr Glu Gly Val Val Ser
                85                  90                  95

Ile Asp Gly Gln Val Lys Ile Leu Lys Gly Leu Asn Leu Lys Val Gln
            100                 105                 110

Ser Gly Gln Thr Val Ala Leu Val Gly Asn Ser Gly Cys Glu Lys Ser
        115                 120                 125

Thr Thr Val Gln Leu Met Gln Arg Leu Tyr Asp Pro Thr Glu Gly Met
130                 135                 140

Val Ser Val Asp Gly Gln Val Lys Ile Leu Lys Gly Leu Asn Leu Lys
145                 150                 155                 160

Val Lys Ser Gly Gln Thr Val Ala Leu Val Gly Asn Ser Gly Cys Gly
                165                 170                 175

Lys Ser Thr Thr Val Gln Leu Leu Gln Arg Leu Tyr Asp Pro Leu Glu
            180                 185                 190

Gly Glu Val Ser Ile Asp Gly Gln Val Gln Ile Leu Lys Gly Leu Asn
        195                 200                 205

Leu Lys Val Lys Ser Gly Gln Thr Val Ala Leu Val Gly Asn Ser Gly
    210                 215                 220

Cys Gly Lys Ser Thr Thr Val Gln Leu Met Gln Pro Leu Tyr Asp Pro
225                 230                 235                 240

Leu Glu Gly Val Val Ser Ile Asp Gly Gln Ile Lys Ile Leu Lys Gly
                245                 250                 255

Leu Asn Leu Lys Val Gln Ser Gly Gln Thr Val Ala Leu Val Gly Asn
            260                 265                 270

Ser Gly Cys Gly Lys Thr Thr Thr Leu Gln Leu Leu Gln Arg Leu Tyr
        275                 280                 285

Asp Pro Thr Glu Gly Thr Ile Ser Ile Asp Gly Gln Val Lys Ile Leu
    290                 295                 300

Lys Gly Leu Asn Leu Lys Val Gln Ser Gly Gln Thr Val Ala Leu Val
305                 310                 315                 320

Gly Ser Ser Gly Cys Thr Lys Ser Thr Thr Val Gln Leu Ile Gln Arg
                325                 330                 335

Leu Tyr Asp Pro Asp Glu Gly Thr Ile Asn Ile Asp Gly Gln
            340                 345                 350

<210> SEQ ID NO 10
<211> LENGTH: 586
<212> TYPE: DNA
<213> ORGANISM: homo sapien
<220> FEATURE:
<221> NAME/KEY: misc_feature
<222> LOCATION: (1)...(586)
<223> OTHER INFORMATION: n = A,T,C or G
```

```
<400> SEQUENCE: 10
gtggggcgga cggaggcggg gaagtcatca ctggtaagtg ccgtgctcgg ngaattggcc      60
ccaagtcacg ggctggttag cgtgcatgga anaattgcct atgtgtctca gcagccctgg    120
gtgttctcgg gaactctgag gagtaatatt ttatttggga gaaatacga aaaggaacga    180 tatgaaaaag tcataaaggc ttgtgctctg aaaaaggatt tacagctgtt ggaggatggn    240
gatctgactg tgataggaga tcggngaacc acgctgagtg gagggcnnaa agcacgggta    300
aaccttgcaa gagcagtgta tcaagatgct gacatctatc tcctggacga tcctctcant    360
gcaagtanat gcggaagtta gcanacactt gttcgaactg tgtaatttgn canntttgc      420 atgagaagat cacaatttta atcgactcat naagtntgca agtacctcaa agctgcaagt    480
cnnattcttg atantgaaag atggtaaaat ggngccaaaa nggnacttac acttgacgtt    540
cctaaaatct ggnatacaat ttngcttcct tttaaanaaa cgataa                    586

<210> SEQ ID NO 11
<211> LENGTH: 338
<212> TYPE: DNA
<213> ORGANISM: homo sapien

<400> SEQUENCE: 11
ctgggaaatc ctctttggta tcagccatgc tgggagaaat ggaaaacgtt cacgggcaca      60
tcaccatcca gggatccaca gcctatgtcc ctcagcagtc ctggattcag aatggaacca    120
tcaaagacaa catcctgttt gggtccgaat acaatgaaaa gaagtaccag caagttctca    180 agcatgcgc tctcctccca gacttggaaa tattgcctgg aggagacatg gctgagatcg    240
gagagaaggg gataaatctc agtggtggtc agaagcagcg agtcagcctg gccagagctg    300
cctatcaaga tgctgatcta tattctggac gatcccct                              338

<210> SEQ ID NO 12
<211> LENGTH: 10
<212> TYPE: PRT
<213> ORGANISM: homo sapien

<400> SEQUENCE: 12

Val Gly Arg Thr Gly Ala Gly Lys Ser Ser
1               5                   10

<210> SEQ ID NO 13
<211> LENGTH: 5
<212> TYPE: PRT
<213> ORGANISM: homo sapien

<400> SEQUENCE: 13

Ala Asx Cys Asp Glu
1               5

<210> SEQ ID NO 14
<211> LENGTH: 19
<212> TYPE: DNA
<213> ORGANISM: Artificial Sequence
<220> FEATURE:
<223> OTHER INFORMATION: primer

<400> SEQUENCE: 14
ccattgaaga tcttcctgg                                                   19

<210> SEQ ID NO 15
<211> LENGTH: 18
```

-continued

```
<212> TYPE: DNA
<213> ORGANISM: Artificial Sequence
<220> FEATURE:
<223> OTHER INFORMATION: primer

<400> SEQUENCE: 15
ggtgttcaat ctgtgtgc                                                     18

<210> SEQ ID NO 16
<211> LENGTH: 224
<212> TYPE: PRT
<213> ORGANISM: homo sapien

<400> SEQUENCE: 16
```

Phe Val Leu Arg His Ile Asn Val Thr Ile Asn Gly Gly Glu Lys Val
 1               5                  10                  15

Gly Ile Val Gly Arg Thr Gly Ala Gly Lys Ser Ser Leu Thr Leu Gly
             20                  25                  30

Leu Phe Arg Ile Asn Glu Ser Ala Glu Gly Ile Ile Ile Asp Gly
         35                  40                  45

Ile Asn Leu Ala Lys Ile Gly Leu His Asp Leu Arg Phe Lys Ile Thr
 50                  55                  60

Ile Ile Pro Gln Asp Pro Val Leu Phe Ser Gly Ser Leu Arg Met Asn
 65                  70                  75                  80

Leu Asp Pro Phe Ser Gln Tyr Ser Asp Glu Glu Val Trp Thr Ser Leu
                 85                  90                  95

Glu Leu Ala His Leu Lys Asp Phe Val Ser Ala Leu Pro Asp Lys Leu
            100                 105                 110

Asp His Glu Cys Ala Glu Gln Gly Glu Asn Leu Ser Val Gly Gln Arg
        115                 120                 125

Gln Leu Val Cys Leu Ala Arg Ala Leu Leu Arg Lys Thr Lys Ile Leu
    130                 135                 140

Val Leu Asp Glu Ala Thr Ala Ala Val Asp Leu Glu Thr Asp Asp Leu
145                 150                 155                 160

Ile Gln Ser Thr Ile Arg Thr Gln Phe Glu Asp Cys Thr Val Leu Thr
                165                 170                 175

Ile Ala His Arg Leu Asn Thr Ile Met Asp Tyr Thr Arg Val Ile Val
            180                 185                 190

Leu Asp Lys Gly Glu Ile Gln Glu Tyr Gly Ala Pro Ser Lys Leu Leu
        195                 200                 205

Gln Gln Arg Gly Leu Phe Tyr Ser Met Ala Lys Asp Ala Gly Leu Val
    210                 215                 220

```
<210> SEQ ID NO 17
<211> LENGTH: 231
<212> TYPE: PRT
<213> ORGANISM: homo sapien

<400> SEQUENCE: 17
```

Leu Val Leu Arg Gly Ile Thr Cys Asp Ile Gly Ser Met Glu Lys Ile
 1               5                  10                  15

Gly Val Val Gly Arg Thr Gly Ala Gly Lys Ser Ser Leu Thr Asn Cys
             20                  25                  30

Leu Phe Arg Ile Leu Glu Ala Ala Gly Gly Gln Ile Ile Ile Asp Gly
         35                  40                  45

Val Asp Leu Ala Ser Ile Gly Leu His Asp Leu Arg Glu Lys Leu Thr
 50                  55                  60

-continued

Ile Ile Pro Gln Asp Pro Ile Leu Phe Ser Gly Ser Leu Arg Met Asn
65                  70                  75                  80

Leu Asp Pro Phe Asn Asn Tyr Ser Asp Glu Glu Ile Trp Lys Ala Leu
                85                  90                  95

Glu Leu Ala His Leu Lys Ser Phe Val Ala Ser Leu Gln Leu Gly Leu
            100                 105                 110

Ser His Glu Val Thr Glu Ala Gly Gly Asn Leu Ser Ile Gly Gln Arg
        115                 120                 125

Gln Leu Leu Cys Leu Gly Arg Ala Leu Leu Arg Lys Ser Lys Ile Leu
    130                 135                 140

Val Leu Asp Glu Ala Thr Ala Ala Val Lys Leu Glu Thr Asp Asn Leu
145                 150                 155                 160

Ile Gln Thr Thr Ile Gln Asn Glu Phe Ala His Cys Thr Val Ile Thr
                165                 170                 175

Ile Ala His Arg Leu His Thr Ile Met Asp Ser Asp Lys Val Met Val
            180                 185                 190

Leu Asp Asn Gly Lys Ile Ile Glu Tyr Gly Ser Pro Glu Glu Leu Leu
        195                 200                 205

Gln Ile Pro Gly Leu Phe Tyr Ser Met Ala Lys Glu Ala Gly Ile Glu
    210                 215                 220

Asn Val Asn Ser Thr Lys Phe
225                 230

<210> SEQ ID NO 18
<211> LENGTH: 224
<212> TYPE: PRT
<213> ORGANISM: homo sapien

<400> SEQUENCE: 18

Leu Val Leu Arg Asp Leu Ser Leu His Val His Gly Gly Glu Lys Val
1               5                   10                  15

Gly Ile Val Gly Arg Thr Gly Ala Gly Lys Ser Ser Met Thr Leu Ala
                20                  25                  30

Cys Ser Arg Ile Leu Glu Ala Ala Lys Gly Glu Ile Arg Ile Asp Gly
            35                  40                  45

Leu Asn Val Ala Asp Ile Gly Phe His Asp Val Arg Cys Gln Met Thr
        50                  55                  60

Ile Ile Pro Arg Asp Pro Ile Leu Phe Ser Gly Thr Leu Arg Met Asn
65                  70                  75                  80

Leu Asp Pro Phe Gly Ser Tyr Ser Glu Glu Asp Ile Trp Trp Ala Leu
                85                  90                  95

Glu Leu Ser His Leu His Thr Phe Val Ser Ser Gln Pro Ala Gly Leu
            100                 105                 110

Asp Phe Gln Cys Ser Glu Gly Gly Glu Asn Leu Ser Val Gly Gln Arg
        115                 120                 125

Gln Leu Val Cys Leu Ala Arg Ala Leu Leu Arg Lys Ser Arg Ile Leu
    130                 135                 140

Val Leu Asp Glu Ala Thr Ala Ala Ile Asp Leu Glu Thr Asp Asn Leu
145                 150                 155                 160

Ile Gln Ala Thr Ile Arg Thr Gln Phe Asp Thr Cys Thr Val Leu Thr
                165                 170                 175

Ile Ala His Arg Leu Asn Thr Ile Met Asp Tyr Thr Arg Val Leu Val
            180                 185                 190

Leu Asp Lys Gly Val Val Ala Glu Phe Asp Ser Pro Ala Asn Leu Leu
        195                 200                 205

```
Ala Ala Arg Gly Ile Phe Tyr Gly Met Ala Arg Asp Ala Gly Leu Ala
    210                 215                 220
```

<210> SEQ ID NO 19
<211> LENGTH: 222
<212> TYPE: PRT
<213> ORGANISM: homo sapien

<400> SEQUENCE: 19

```
Thr Ile Lys Pro Lys Glu Lys Ile Gly Ile Val Gly Arg Thr Gly Ser
 1               5                  10                  15

Gly Lys Ser Ser Leu Gly Met Ala Leu Phe Arg Leu Val Glu Leu Ser
                20                  25                  30

Gly Gly Cys Ile Lys Ile Asp Gly Val Arg Ile Ser Asp Ile Gly Leu
            35                  40                  45

Ala Gly Leu Arg Ser Lys Leu Ser Ile Ile Pro Gln Glu Pro Val Leu
        50                  55                  60

Phe Ser Gly Thr Val Arg Ser Asn Leu Asp Pro Phe Asn Gln Tyr Thr
 65                  70                  75                  80

Glu Asp Gln Ile Trp Asp Ala Leu Glu Arg Thr His Met Lys Glu Cys
                85                  90                  95

Ile Ala Gln Leu Pro Leu Lys Leu Glu Ser Glu Val Met Glu Asn Gly
                100                 105                 110

Asp Asn Arg Ser Val Gly Glu Arg Gln Leu Leu Cys Leu Ala Arg Ala
            115                 120                 125

Leu Leu Arg His Cys Lys Ile Leu Ile Leu Asp Glu Ala Thr Ala Ala
        130                 135                 140

Met Asp Thr Glu Thr Asp Leu Leu Ile Gln Glu Thr Ile Arg Glu Ala
145                 150                 155                 160

Phe Ala Asp Cys Thr Met Leu Thr Ile Ala His Arg Leu His Thr Val
                165                 170                 175

Leu Gly Ser Asp Arg Ile Met Val Leu Ala Gln Gly Gln Val Val Glu
                180                 185                 190

Phe Asp Thr Pro Ser Val Leu Leu Ser Asn Asp Ser Ser Arg Phe Tyr
            195                 200                 205

Ala Met Phe Ala Ala Ala Glu Asn Lys Val Ala Val Lys Gly
        210                 215                 220
```

<210> SEQ ID NO 20
<211> LENGTH: 222
<212> TYPE: PRT
<213> ORGANISM: homo sapien

<400> SEQUENCE: 20

```
Leu Ala Val Gln Gly Val Ser Phe Lys Ile His Ala Gly Glu Lys Val
 1               5                  10                  15

Gly Ile Val Gly Arg Thr Gly Ala Gly Lys Asp Asp Leu Ala Ser Gly
                20                  25                  30

Leu Leu Arg Leu Gln Glu Ala Ala Glu Gly Gly Ile Trp Ile Asp Gly
            35                  40                  45

Val Pro Leu Ala Gly Val Gly Leu Gly Thr Leu Arg Ser Arg Ile Ser
        50                  55                  60

Ile Ile Pro Gln Asp Pro Ile Leu Phe Pro Gly Ser Leu Arg Met Asn
 65                  70                  75                  80

Leu Asp Leu Leu Gln Glu His Ser Asp Glu Ala Ile Trp Ala Ala Leu
                85                  90                  95
```

```
Glu Thr Val Leu Lys Ala Leu Val Ala Ser Leu Pro Gly Gln Leu Tyr
            100                 105                 110

Lys Cys Ala Asp Arg Gly Glu Asp Leu Ser Val Gly Lys Gln Leu
        115                 120                 125

Leu Cys Leu Ala Arg Ala Leu Leu Arg Lys Thr Gln Ile Leu Ile Leu
        130                 135                 140

Asp Glu Ala Thr Ala Ala Val Lys Pro Gly Thr Glu Leu Gln Met Gln
145                 150                 155                 160

Ala Met Leu Gly Ser Trp Phe Ala Gln Cys Thr Val Leu Leu Ile Ala
                165                 170                 175

His Arg Leu Arg Ser Val Met Asp Cys Ala Arg Val Leu Val Met Asp
                180                 185                 190

Lys Gly Gln Val Ala Glu Ser Gly Ser Pro Ala Gln Leu Leu Ala Gln
                195                 200                 205

Lys Gly Leu Phe Tyr Arg Leu Ala Gln Glu Ser Gly Leu Val
        210                 215                 220

<210> SEQ ID NO 21
<211> LENGTH: 271
<212> TYPE: PRT
<213> ORGANISM: homo sapien
<220> FEATURE:
<221> NAME/KEY: VARIANT
<222> LOCATION: (1)...(271)
<223> OTHER INFORMATION: Xaa = Any Amino Acid

<400> SEQUENCE: 21

Xaa Xaa Xaa Xaa Xaa Xaa Xaa Xaa Xaa Ile Xaa Xaa Xaa Glu Lys Xaa
1               5                   10                  15

Gly Ile Val Gly Arg Thr Gly Ala Gly Lys Ser Ser Leu Xaa Xaa Xaa
                20                  25                  30

Leu Xaa Arg Xaa Xaa Glu Xaa Ala Xaa Gly Xaa Ile Xaa Ile Asp Gly
        35                  40                  45

Xaa Xaa Ile Ala Xaa Ile Gly Leu His Asp Leu Arg Xaa Xaa Xaa Xaa
50                  55                  60

Ile Ile Pro Gln Asp Pro Xaa Leu Phe Ser Gly Xaa Leu Arg Met Asn
65                  70                  75                  80

Leu Asp Pro Phe Xaa Xaa Tyr Ser Xaa Glu Xaa Ile Trp Xaa Ala Leu
                85                  90                  95

Glu Xaa Xaa His Leu Lys Xaa Xaa Val Xaa Xaa Leu Pro Xaa Xaa Leu
                100                 105                 110

Xaa Xaa Glu Xaa Xaa Glu Xaa Gly Xaa Asn Leu Ser Val Gly Gln Arg
        115                 120                 125

Gln Leu Xaa Cys Leu Ala Arg Ala Leu Leu Arg Lys Xaa Xaa Ile Leu
        130                 135                 140

Xaa Ile Asp Glu Ala Thr Ala Ala Val Asp Xaa Asx Thr Asp Xaa Leu
145                 150                 155                 160

Ile Gln Xaa Thr Ile Arg Xaa Xaa Glu Ala Xaa Cys Thr Val Leu Thr
                165                 170                 175

Ile Ala His Arg Leu Xaa Thr Ile Met Asp Xaa Xaa Arg Val Xaa Val
                180                 185                 190

Leu Asp Xaa Gly Xaa Xaa Xaa Glu Xaa Xaa Xaa Pro Xaa Xaa Leu Leu
        195                 200                 205

Xaa Xaa Xaa Xaa Gly Xaa Phe Tyr Xaa Met Ala Xaa Xaa Ala Gly Xaa
210                 215                 220
```

```
Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
            245                 250                 255

Xaa Xaa Xaa Xaa Xaa Xaa Xaa Xaa Xaa Xaa Xaa Xaa Xaa Xaa
            260                 265                 270

<210> SEQ ID NO 22
<211> LENGTH: 500
<212> TYPE: DNA
<213> ORGANISM: homo sapien

<400> SEQUENCE: 22
acttaaagaa accattgaag atcttcctgg taaaatggat actgaattag cagaatcagg      60 atccaattt  agtgttggac aaagacaact ggtgtgcctt gccagggcaa ttctcaggaa     120
aaatcagata ttgattattg atgaagcgac ggcaaatgtg gatccaagaa ctgatgagtt     180
aatacaaaaa aaaatccggg agaaatttgc ccactgcacc gtgctaacca ttgcacacag     240
attgaacacc attattgaca gcgacaagat aatggtttta gattcaggaa gactgaaaga     300
atatgatgag ccgtatgttt tgctgcaaaa taaagagagc ctattttaca agatggtgca     360
acaactgggc aaggcagaag ccgctgccct cactgaaaca gcaaaacagg tatacttcaa     420
aagaaattat ccacatattg gtcacactga ccacatggtt acaaacactt ccaatggaca     480
gccctcgacc ttaactattt                                                  500

<210> SEQ ID NO 23
<211> LENGTH: 250
<212> TYPE: DNA
<213> ORGANISM: homo sapien

<400> SEQUENCE: 23
acttaaagaa accattgaag atcttcctgg taaaatggat actgaattag cagaatcagg      60 atccaattt  agtgttggac aaagacaact ggtgtgcctt gccagggcaa ttctcaggaa     120
aaatcagata ttgattattg atgaagcgac ggcaaatgtg gatccaagaa ctgatgagtt     180
aatacaaaaa aaaatccggg agaaatttgc ccactgcacc gtgctaacca ttgcacacag     240
attgaacacc                                                             250

<210> SEQ ID NO 24
<211> LENGTH: 33
<212> TYPE: DNA
<213> ORGANISM: homo sapien

<400> SEQUENCE: 24
acagcgacaa gataatggtt taagagtttg aca                                    33

<210> SEQ ID NO 25
<211> LENGTH: 17
<212> TYPE: PRT
<213> ORGANISM: homo sapien
<220> FEATURE:
<221> NAME/KEY: VARIANT
<222> LOCATION: (1)...(17)
<223> OTHER INFORMATION: Xaa = Any Amino Acid

<400> SEQUENCE: 25

Thr Xaa Arg Asn His Xaa Arg Ser Ser Trp Xaa Asn Gly Tyr Xaa Ile
 1               5                  10                  15

Ser
```

-continued

```
<210> SEQ ID NO 26
<211> LENGTH: 11
<212> TYPE: PRT
<213> ORGANISM: homo sapien

<400> SEQUENCE: 26

Leu Lys Glu Thr Ile Glu Lys Leu Pro Gly Lys
1               5                   10

<210> SEQ ID NO 27
<211> LENGTH: 15
<212> TYPE: PRT
<213> ORGANISM: homo sapien

<400> SEQUENCE: 27

Leu Lys Lys Pro Leu Lys Ile Phe Leu Val Lys Trp Ile Ile Asn
1               5                   10                  15
```